(12) United States Patent
Yager et al.

(10) Patent No.: US 10,939,923 B2
(45) Date of Patent: Mar. 9, 2021

(54) INSTRUMENTS AND METHODS IN PERFORMING KINEMATICALLY-ALIGNED TOTAL KNEE ARTHROPLASTY

(71) Applicant: Zimmer, Inc., Warsaw, IN (US)

(72) Inventors: Edward R. Yager, Fort Wayne, IN (US); Shaun R. Cronin, Warsaw, IN (US); Stephen M. Howell, Sacramento, CA (US); David B. Willard, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 323 days.

(21) Appl. No.: 16/162,520

(22) Filed: Oct. 17, 2018

(65) Prior Publication Data

US 2019/0046215 A1 Feb. 14, 2019

Related U.S. Application Data

(63) Continuation of application No. 14/809,810, filed on Jul. 27, 2015, now Pat. No. 10,130,375.

(Continued)

(51) Int. Cl.
*A61B 17/58* (2006.01)
*A61B 17/60* (2006.01)
(Continued)

(52) U.S. Cl.
CPC ........ *A61B 17/155* (2013.01); *A61B 17/1764* (2013.01); *A61B 2017/564* (2013.01); *A61B 2017/90* (2013.01)

(58) Field of Classification Search
CPC combination set(s) only.
See application file for complete search history.

(56) References Cited

U.S. PATENT DOCUMENTS

| 2,246,066 A | 6/1941 | Frank |
| 4,081,866 A | 4/1978 | Upshaw et al. |

(Continued)

FOREIGN PATENT DOCUMENTS

| AU | 2006325787 B2 | 10/2013 |
| CA | 2641966 C | 11/2016 |

(Continued)

OTHER PUBLICATIONS

"U.S. Appl. No. 11/611,021, Notice of Allowance dated Nov. 4, 2016", 10 pgs.

(Continued)

*Primary Examiner* — Sameh R Boles
(74) *Attorney, Agent, or Firm* — Schwegman Lundberg & Woessner, P.A.

(57) ABSTRACT

Methods and instruments for performing a kinematically-aligned total knee arthroplasty (TKA) are disclosed. Goals of the kinematically-aligned TKA can include restoration of (1) the femoral and tibial joint lines to the patient's natural joint line, (2) the patient's Hip-Knee-Ankle alignment to their constitutional alignment prior to developing osteoarthritis and (3) restoration of the patient's natural soft tissue laxity and envelope. A shim block assembly can be used in resecting the distal medial and lateral condyles to account for cartilage wear on the distal condyles from osteoarthritis. The shim block assembly can include a plurality of shims, and each shim can be attachable to or integral with a reference block. At least one of the plurality of shims can have a medial portion with a thickness different from a thickness of a lateral portion of the shim. The shims need not be joined together as a single medial/lateral component but may be independent of one another. A particular shim can be selected for use based on matching the medial and lateral (Continued)

thicknesses with a determined wear of cartilage on the distal medial and lateral condyles.

21 Claims, 29 Drawing Sheets

Related U.S. Application Data

(60) Provisional application No. 62/031,572, filed on Jul. 31, 2014.

(51) Int. Cl.
*A61F 2/00* (2006.01)
*A61B 17/15* (2006.01)
*A61B 17/17* (2006.01)
*A61B 17/56* (2006.01)
*A61B 17/90* (2006.01)

(56) References Cited

U.S. PATENT DOCUMENTS

| | | |
|---|---|---|
| 4,340,978 A | 7/1982 | Buechel et al. |
| 4,662,889 A | 5/1987 | Zichner et al. |
| 4,769,040 A | 9/1988 | Wevers |
| 4,888,020 A | 12/1989 | Horber |
| 4,944,756 A | 7/1990 | Kenna |
| 4,950,298 A | 8/1990 | Gustilo et al. |
| 4,959,071 A | 9/1990 | Brown et al. |
| 5,007,933 A | 4/1991 | Sidebotham et al. |
| 5,061,271 A | 10/1991 | Van Zile |
| 5,084,982 A | 2/1992 | Feng |
| 5,133,758 A | 7/1992 | Hollister |
| 5,133,760 A | 7/1992 | Petersen et al. |
| 5,137,536 A | 8/1992 | Koshino |
| 5,226,915 A | 7/1993 | Bertin |
| 5,282,861 A | 2/1994 | Kaplan |
| 5,282,869 A | 2/1994 | Miyajima et al. |
| 5,326,361 A | 7/1994 | Hollister |
| 5,330,532 A | 7/1994 | Ranawat |
| 5,445,642 A | 8/1995 | McNulty et al. |
| 5,519,942 A | 5/1996 | Webb |
| 5,549,686 A | 8/1996 | Johnson et al. |
| 5,549,688 A | 8/1996 | Ries et al. |
| 5,609,643 A | 3/1997 | Colleran et al. |
| 5,681,354 A | 10/1997 | Eckhoff |
| 5,688,279 A | 11/1997 | McNulty et al. |
| 5,702,460 A | 12/1997 | Carls et al. |
| 5,722,179 A | 3/1998 | Zanier |
| 5,728,162 A | 3/1998 | Eckhoff |
| 5,776,201 A | 7/1998 | Colleran et al. |
| 5,824,105 A | 10/1998 | Ries et al. |
| 5,871,546 A | 2/1999 | Colleran et al. |
| 5,879,354 A | 3/1999 | Haines et al. |
| 5,879,393 A | 3/1999 | Whiteside et al. |
| 5,935,173 A | 8/1999 | Roger et al. |
| 6,013,103 A | 1/2000 | Kaufman et al. |
| 6,039,764 A | 3/2000 | Pottenger et al. |
| 6,074,424 A | 6/2000 | Perrone, Jr. et al. |
| 6,096,082 A | 8/2000 | Stegmuller et al. |
| 6,106,529 A | 8/2000 | Techiera |
| 6,152,960 A | 11/2000 | Pappas |
| 6,197,064 B1 | 3/2001 | Haines et al. |
| 6,217,619 B1 | 4/2001 | Keller |
| 6,235,060 B1 | 5/2001 | Kubein-Meesenburg et al. |
| 6,264,697 B1 | 7/2001 | Walker |
| 6,325,828 B1 | 12/2001 | Dennis et al. |
| 6,364,911 B1 | 4/2002 | Schmotzer et al. |
| 6,421,927 B1 | 7/2002 | Bach et al. |
| 6,540,786 B2 | 4/2003 | Chibrac et al. |
| 6,540,787 B2 | 4/2003 | Biegun et al. |
| 6,589,283 B1 | 7/2003 | Metzger et al. |
| 6,616,696 B1 | 9/2003 | Merchant |
| 6,699,291 B1 | 3/2004 | Augoyard et al. |
| 6,712,856 B1 | 3/2004 | Carignan et al. |
| 6,770,099 B2 | 8/2004 | Andriacchi et al. |
| 6,802,865 B2 | 10/2004 | Biegun et al. |
| 6,846,329 B2 | 1/2005 | Mcminn |
| 6,893,467 B1 | 5/2005 | Bercovy |
| 7,081,137 B1 | 7/2006 | Servidio |
| 7,297,164 B2 | 11/2007 | Johnson et al. |
| 7,306,609 B2 | 12/2007 | Schmotzer et al. |
| 7,364,590 B2 | 4/2008 | Siebel |
| 7,413,577 B1 | 8/2008 | Servidio |
| 7,442,196 B2 | 10/2008 | Fisher et al. |
| 7,465,320 B1 | 12/2008 | Kito et al. |
| 7,678,152 B2 | 3/2010 | Suguro et al. |
| 7,691,150 B2 | 4/2010 | Cronin et al. |
| 7,695,520 B2 | 4/2010 | Metzger et al. |
| 7,806,897 B1 | 10/2010 | Bonutti |
| 8,062,377 B2 | 11/2011 | Haines |
| 8,075,626 B2 | 12/2011 | Dun |
| 8,088,167 B2 | 1/2012 | Haines |
| 8,211,181 B2 | 7/2012 | Walker |
| 8,292,964 B2 | 10/2012 | Walker |
| 8,298,288 B2 | 10/2012 | Walker |
| 8,357,202 B2 | 1/2013 | Heggendorn et al. |
| 8,377,141 B2 | 2/2013 | Mcminn |
| 8,394,147 B2 | 3/2013 | Otto et al. |
| 8,409,293 B1 | 4/2013 | Howard et al. |
| 8,480,753 B2 | 7/2013 | Collazo et al. |
| 8,480,754 B2 | 7/2013 | Bojarski et al. |
| 8,500,816 B2 | 8/2013 | Dees, Jr. et al. |
| 8,551,179 B2 | 10/2013 | Jones et al. |
| 8,603,101 B2 | 12/2013 | Claypool et al. |
| 8,721,732 B2 | 5/2014 | Samuelson et al. |
| 8,911,502 B2 | 12/2014 | Li et al. |
| 8,932,365 B2 | 1/2015 | Parisi et al. |
| 9,003,672 B2 | 4/2015 | Lozano, IV |
| 9,060,868 B2 | 6/2015 | Parisi et al. |
| 9,173,744 B2 | 11/2015 | Donno et al. |
| 9,308,095 B2 | 4/2016 | Parisi et al. |
| 9,592,127 B2 | 3/2017 | Earl et al. |
| 9,839,521 B2 | 12/2017 | Todd et al. |
| 9,867,708 B2 | 1/2018 | Donno et al. |
| 9,956,048 B2 | 5/2018 | Bojarski et al. |
| 10,045,850 B2 | 8/2018 | Parisi et al. |
| 10,130,375 B2 | 11/2018 | Yager et al. |
| 10,136,997 B2 | 11/2018 | Yager |
| 10,582,982 B2 | 3/2020 | Fisher et al. |
| 10,631,991 B2 | 4/2020 | Yager |
| 2003/0153924 A1 | 8/2003 | Kana et al. |
| 2003/0158606 A1 | 8/2003 | Coon et al. |
| 2003/0225458 A1 | 12/2003 | Donkers et al. |
| 2004/0039450 A1 | 2/2004 | Griner et al. |
| 2004/0172137 A1 | 9/2004 | Blaylock et al. |
| 2004/0204766 A1 | 10/2004 | Siebel |
| 2004/0243245 A1 | 12/2004 | Plumet et al. |
| 2004/0249467 A1 | 12/2004 | Meyers et al. |
| 2005/0055102 A1 | 3/2005 | Tornier et al. |
| 2005/0102032 A1 | 5/2005 | Beynnon et al. |
| 2005/0107884 A1 | 5/2005 | Johnson et al. |
| 2005/0143832 A1 | 6/2005 | Carson |
| 2005/0177169 A1 | 8/2005 | Fisher et al. |
| 2005/0283249 A1 | 12/2005 | Carson |
| 2005/0283250 A1 | 12/2005 | Coon et al. |
| 2005/0283251 A1 | 12/2005 | Coon et al. |
| 2005/0283252 A1 | 12/2005 | Coon et al. |
| 2005/0283253 A1 | 12/2005 | Coon et al. |
| 2006/0028773 A1 | 2/2006 | Shimazawa et al. |
| 2006/0129246 A1 | 6/2006 | Steffensmeier |
| 2006/0142774 A1 | 6/2006 | Metzger |
| 2006/0200163 A1* | 9/2006 | Roger ............... A61B 17/155 606/89 |
| 2006/0224244 A1 | 10/2006 | Thomas et al. |
| 2006/0235541 A1 | 10/2006 | Hodorek |
| 2006/0235542 A1 | 10/2006 | Hodorek et al. |
| 2006/0241634 A1 | 10/2006 | Tuttle et al. |
| 2006/0265078 A1 | 11/2006 | Mcminn |
| 2006/0265080 A1 | 11/2006 | Mcminn |
| 2006/0287733 A1 | 12/2006 | Bonutti |
| 2007/0088444 A1 | 4/2007 | Hodorek et al. |
| 2007/0123984 A1 | 5/2007 | Hodorek |
| 2007/0135925 A1 | 6/2007 | Walker |

(56) References Cited

U.S. PATENT DOCUMENTS

| | | |
|---|---|---|
| 2007/0135926 A1 | 6/2007 | Walker |
| 2007/0150066 A1 | 6/2007 | McMinn et al. |
| 2007/0179607 A1 | 8/2007 | Hodorek et al. |
| 2007/0233269 A1 | 10/2007 | Steines et al. |
| 2007/0260323 A1 | 11/2007 | Earl et al. |
| 2008/0058947 A1 | 3/2008 | Earl et al. |
| 2008/0058948 A1 | 3/2008 | Biegun et al. |
| 2008/0097615 A1 | 4/2008 | Lipman et al. |
| 2008/0097616 A1 | 4/2008 | Meyers et al. |
| 2008/0114463 A1 | 5/2008 | Auger et al. |
| 2008/0119940 A1 | 5/2008 | Otto et al. |
| 2008/0140212 A1 | 6/2008 | Metzger et al. |
| 2008/0184582 A1 | 8/2008 | Kim |
| 2008/0188937 A1 | 8/2008 | Ribic |
| 2008/0188942 A1 | 8/2008 | Brown et al. |
| 2008/0243258 A1 | 10/2008 | Sancheti |
| 2008/0281428 A1 | 11/2008 | Meyers et al. |
| 2008/0288080 A1 | 11/2008 | Sancheti |
| 2009/0036992 A1 | 2/2009 | Tsakonas |
| 2009/0043395 A1 | 2/2009 | Hotokebuchi et al. |
| 2009/0062924 A1 | 3/2009 | Kito et al. |
| 2009/0105772 A1 | 4/2009 | Seebeck et al. |
| 2009/0132055 A1 | 5/2009 | Ferro |
| 2009/0149963 A1 | 6/2009 | Sekel |
| 2009/0222103 A1 | 9/2009 | Fitz et al. |
| 2009/0265011 A1 | 10/2009 | Mandell |
| 2009/0265013 A1 | 10/2009 | Mandell |
| 2009/0306786 A1 | 12/2009 | Samuelson |
| 2009/0306787 A1 | 12/2009 | Crabtree et al. |
| 2009/0319047 A1 | 12/2009 | Walker |
| 2009/0319048 A1 | 12/2009 | Shah et al. |
| 2009/0319049 A1 | 12/2009 | Shah et al. |
| 2009/0326663 A1 | 12/2009 | Dun |
| 2009/0326665 A1 | 12/2009 | Wyss et al. |
| 2009/0326666 A1 | 12/2009 | Wyss et al. |
| 2009/0326667 A1 | 12/2009 | Williams et al. |
| 2010/0036499 A1 | 2/2010 | Pinskerova |
| 2010/0036500 A1 | 2/2010 | Heldreth et al. |
| 2010/0042224 A1 | 2/2010 | Otto et al. |
| 2010/0161067 A1 | 6/2010 | Saleh et al. |
| 2010/0191298 A1 | 7/2010 | Earl et al. |
| 2010/0211179 A1 | 8/2010 | Angibaud et al. |
| 2010/0249657 A1 | 9/2010 | Nycz et al. |
| 2010/0293802 A1 | 11/2010 | Stockman |
| 2010/0305708 A1 | 12/2010 | Lang |
| 2010/0329530 A1 | 12/2010 | Lang et al. |
| 2011/0022179 A1 | 1/2011 | Andriacchi et al. |
| 2011/0029091 A1 | 2/2011 | Bojarski et al. |
| 2011/0093083 A1 | 4/2011 | Earl et al. |
| 2011/0099829 A1 | 5/2011 | Prior et al. |
| 2011/0144760 A1 | 6/2011 | Wong et al. |
| 2011/0218541 A1 | 9/2011 | Bailey et al. |
| 2011/0307067 A1 | 12/2011 | Dees |
| 2012/0089234 A1 | 4/2012 | Mouillet et al. |
| 2012/0203350 A1 | 8/2012 | Hagen et al. |
| 2012/0310362 A1 | 12/2012 | Li et al. |
| 2012/0323334 A1 | 12/2012 | Jones et al. |
| 2012/0323335 A1 | 12/2012 | Parisi et al. |
| 2012/0323336 A1 | 12/2012 | Parisi et al. |
| 2012/0323337 A1 | 12/2012 | Parisi et al. |
| 2012/0330319 A1 | 12/2012 | Birkbeck et al. |
| 2013/0006370 A1 | 1/2013 | Wogoman et al. |
| 2013/0006371 A1 | 1/2013 | Wogoman et al. |
| 2013/0006376 A1 | 1/2013 | Wogoman et al. |
| 2013/0006378 A1 | 1/2013 | Wogoman |
| 2013/0024001 A1 | 1/2013 | Wentorf et al. |
| 2013/0035765 A1 | 2/2013 | Dacus |
| 2013/0197653 A1 | 8/2013 | Hawkins et al. |
| 2013/0204380 A1 | 8/2013 | Mouillet et al. |
| 2013/0211532 A1 | 8/2013 | Samuelson et al. |
| 2013/0218284 A1 | 8/2013 | Eickmann et al. |
| 2013/0226305 A1 | 8/2013 | Donno et al. |
| 2013/0227854 A1 | 9/2013 | Zhang et al. |
| 2013/0345821 A1 | 12/2013 | Jones et al. |
| 2014/0025081 A1 | 1/2014 | Lorio et al. |
| 2014/0128973 A1 | 5/2014 | Howard et al. |
| 2014/0142713 A1 | 5/2014 | Wright et al. |
| 2014/0228851 A1 | 8/2014 | Guloy, Jr. et al. |
| 2015/0045801 A1 | 2/2015 | Axelson, Jr. et al. |
| 2015/0081031 A1 | 3/2015 | Parisi et al. |
| 2015/0196366 A1 | 7/2015 | Kim et al. |
| 2015/0265410 A1 | 9/2015 | Parisi et al. |
| 2015/0374500 A1 | 12/2015 | Donno et al. |
| 2016/0030053 A1 | 2/2016 | Yager et al. |
| 2016/0220379 A1 | 8/2016 | Parisi et al. |
| 2016/0270856 A1 | 9/2016 | Park et al. |
| 2016/0278873 A1 | 9/2016 | Fisher et al. |
| 2017/0086982 A1 | 3/2017 | Yager |
| 2017/0156872 A1 | 6/2017 | Earl et al. |
| 2018/0064543 A1 | 3/2018 | Wright et al. |
| 2018/0092746 A1 | 4/2018 | Donno et al. |
| 2018/0125584 A1 | 5/2018 | Lang |
| 2018/0140440 A1 | 5/2018 | Jackson et al. |
| 2019/0046323 A1 | 2/2019 | Yager |

FOREIGN PATENT DOCUMENTS

| | | |
|---|---|---|
| CN | 101330883 A | 12/2008 |
| CN | 101522137 A | 9/2009 |
| CN | 101642394 A | 2/2010 |
| CN | 101658446 A | 3/2010 |
| CN | 101664347 A | 3/2010 |
| CN | 101669844 A | 3/2010 |
| CN | 101627930 A | 10/2010 |
| CN | 101879099 A | 11/2010 |
| CN | 101959475 A | 1/2011 |
| CN | 102006839 A | 4/2011 |
| CN | 102006840 A | 4/2011 |
| CN | 102076283 A | 5/2011 |
| CN | 101330883 B | 3/2013 |
| CN | 103118633 A | 5/2013 |
| CN | 103732186 A | 4/2014 |
| CN | 103732187 A | 4/2014 |
| CN | 103732188 A | 4/2014 |
| CN | 103747762 A | 4/2014 |
| CN | 203657640 U | 6/2014 |
| CN | 103732188 B | 5/2016 |
| CN | 103732186 B | 9/2016 |
| CN | 106214293 A | 12/2016 |
| DE | 202007014128 U1 | 1/2008 |
| EP | 0303467 A2 | 2/1989 |
| EP | 0546726 A1 | 6/1993 |
| EP | 0376658 B1 | 6/1994 |
| EP | 0381352 B1 | 6/1994 |
| EP | 0722721 A1 | 7/1996 |
| EP | 0567705 B1 | 7/1997 |
| EP | 0993812 A2 | 4/2000 |
| EP | 1013232 A2 | 6/2000 |
| EP | 1285638 B1 | 2/2003 |
| EP | 1033117 B1 | 6/2004 |
| EP | 0975286 B1 | 8/2004 |
| EP | 1477142 A2 | 11/2004 |
| EP | 1477143 A1 | 11/2004 |
| EP | 1013232 B1 | 10/2005 |
| EP | 1285638 B1 | 11/2005 |
| EP | 1719478 A2 | 11/2006 |
| EP | 1722721 A1 | 11/2006 |
| EP | 1354571 B1 | 6/2007 |
| EP | 1862150 A1 | 12/2007 |
| EP | 2004099 A2 | 12/2008 |
| EP | 1867302 B1 | 9/2009 |
| EP | 2147660 A1 | 1/2010 |
| EP | 2158878 A1 | 3/2010 |
| EP | 1555962 B1 | 2/2011 |
| EP | 2324799 A2 | 5/2011 |
| EP | 2335654 A1 | 6/2011 |
| EP | 2720646 A1 | 4/2014 |
| FR | 2901996 A1 | 12/2007 |
| FR | 3008605 A1 | 1/2015 |
| JP | 64068255 A | 3/1989 |
| JP | 341694 Y2 | 9/1991 |
| JP | 3267055 A | 11/1991 |
| JP | 0553501 A | 3/1993 |
| JP | 0568987 A | 3/1993 |

(56) References Cited

FOREIGN PATENT DOCUMENTS

| | | | |
|---|---|---|---|
| JP | 9149908 A | 6/1997 | |
| JP | 11504226 A | 4/1999 | |
| JP | 11511347 A | 10/1999 | |
| JP | 2003513706 A | 4/2003 | |
| JP | 3469972 B2 | 11/2003 | |
| JP | 3495161 B2 | 2/2004 | |
| JP | 2004166802 A | 6/2004 | |
| JP | 2005532089 A | 10/2005 | |
| JP | 2008502393 A | 1/2008 | |
| JP | 2008503327 A | 2/2008 | |
| JP | 4077041 B2 | 4/2008 | |
| JP | 2008523962 A | 7/2008 | |
| JP | 2009519781 A | 5/2009 | |
| JP | 4820547 B2 | 11/2011 | |
| JP | 5571863 B1 | 7/2014 | |
| JP | 2014522290 A | 9/2014 | |
| JP | 2014522291 A | 9/2014 | |
| JP | 2014522292 A | 9/2014 | |
| JP | 2014522671 A | 9/2014 | |
| JP | 2015164599 A | 9/2015 | |
| JP | 5792898 B2 | 10/2015 | |
| WO | WO-9014806 A1 | 12/1990 | |
| WO | WO-9535074 A1 | 12/1995 | |
| WO | WO-9603939 A1 | 2/1996 | |
| WO | WO-0023010 A1 | 4/2000 | |
| WO | WO-03094782 A2 | 11/2003 | |
| WO | WO-2004016204 A1 | 2/2004 | |
| WO | WO-2004084740 A1 | 10/2004 | |
| WO | WO-2005037147 A1 | 4/2005 | |
| WO | WO-2005051240 A1 | 6/2005 | |
| WO | WO-2005122967 A1 | 12/2005 | |
| WO | WO-2006058057 A2 | 6/2006 | |
| WO | WO-2007007841 A1 | 1/2007 | |
| WO | WO-2007053905 A1 | 5/2007 | |
| WO | WO-2007054553 A1 | 5/2007 | |
| WO | WO-2007070859 A2 | 6/2007 | |
| WO | WO-2007109641 A2 | 9/2007 | |
| WO | WO-2008054389 A1 | 5/2008 | |
| WO | WO-2009088234 A2 | 7/2009 | |
| WO | WO-2009088236 A2 | 7/2009 | |
| WO | WO-2009088238 A2 | 7/2009 | |
| WO | WO-2009105495 A1 | 8/2009 | |
| WO | WO-2010008803 A2 | 1/2010 | |
| WO | WO-2010075365 A2 | 7/2010 | |
| WO | WO-2010108550 A1 | 9/2010 | |
| WO | WO-2011072235 A2 | 6/2011 | |
| WO | WO-2012031774 A1 | 3/2012 | |
| WO | WO-2012112698 A2 | 8/2012 | |
| WO | WO-2012173704 A1 | 12/2012 | |
| WO | WO-2012173706 A1 | 12/2012 | |
| WO | WO-2012173740 A1 | 12/2012 | |
| WO | WO-2016153927 A1 | 9/2016 | |
| WO | WO-2017058535 A1 | 4/2017 | |

OTHER PUBLICATIONS

"U.S. Appl. No. 12/974,018, Appeal Decision dated Aug. 1, 2017", 8 pgs.

"U.S. Appl. No. 14/845,522, Final Office Action dated Jun. 13, 2017", 6 pgs.

"U.S. Appl. No. 14/845,522, Final Office Action dated Oct. 18, 2016", 10 pgs.

"U.S. Appl. No. 14/845,522, Non Final Office Action dated Feb. 8, 2017", 11 pgs.

"U.S. Appl. No. 14/845,522, Notice of Allowance dated Sep. 14, 2017", 7 pgs.

"U.S. Appl. No. 14/845,522, Response filed Apr. 12, 2017 to Non Final Office Action dated Feb. 8, 2017", 16 pgs.

"U.S. Appl. No. 14/845,522, Response filed Aug. 14, 2017 to Final Office Action dated Jun. 13, 2017", 14 pgs.

"U.S. Appl. No. 14/845,622, Response filed Jan. 11, 2017 to Final Office Action dated Oct. 18, 2016", 12 pgs.

"U.S. Appl. No. 15/073,167, Response Filed Oct. 26, 2018 to Restriction Requirement dated Aug. 28, 2018", 8 pgs.

"U.S. Appl. No. 15/073,167, Restriction Requirement dated Aug. 28, 2018", 6 pgs.

"U.S. Appl. No. 15/092,107, Notice of Allowability dated May 10, 2018", 2 pgs.

"U.S. Appl. No. 15/092,107, Notice of Allowance dated Apr. 18, 2018", 8 pgs.

"U.S. Appl. No. 15/092,107, Response filed Jan. 9, 2018 to Restriction Requirement dated Nov. 17, 2017", 16 pgs.

"U.S. Appl. No. 15/092,107, Restriction Requirement dated Nov. 17, 2017", 7 pgs.

"U.S. Appl. No. 15/267,826, Notice of Allowability dated Aug. 31, 2018", 2 pgs.

"U.S. Appl. No. 15/267,826, Notice of Allowance dated Aug. 15, 2018", 7 pgs.

"U.S. Appl. No. 15/424,382, Preliminary Amendment filed Feb. 23, 2017", 9 pgs.

"U.S. Appl. No. 15/835,144, Non Final Office Action dated Jul. 11, 2018", 9 pgs.

"U.S. Appl. No. 15/835,144, Preliminary Amendment filed Dec. 27, 2017", 7 pgs.

"Australian Application Serial No. 2016202865, First Examination Report dated Jun. 26, 2017", 2 pgs.

"Australian Application Serial No. 2016202865, Response filed Aug. 16, 2017 to First Examination Report dated Jun. 26, 2017", 22pgs.

"Canadian Application Serial No. 2,839,433, Office Action dated Feb. 26, 2018", 4 pgs.

"Chinese Application Serial No. 201610697089.0, Office Action dated Feb. 7, 2018", (W/ English Translation), 27 pgs.

"Chinese Application Serial No. 201610697089.0, Office Action dated Jul. 16, 2018", w/ English translation, 10 pgs.

"Chinese Application Serial No. 201610697089.0, Office Action dated Jul. 25, 2017", With English Translation, 30 pgs.

"Chinese Application Serial No. 201610697089.0, Response filed Apr. 10, 2018 to Office Action dated Feb. 7, 2018", w/ Concise Statement of Relevance, 4 pgs.

"Chinese Application Serial No. 201610697089.0, Response filed Aug. 2, 2018 to Office Action dated Jul. 16, 2018", w/ Concise Statement of Relevance, 11 pgs.

"Chinese Application Serial No. 201610697089.0, Response filed Nov. 1, 2017 to Office Action dated Jul. 25, 2017", w/English Claims, 11 pgs.

"European Application Serial No. 14200265.8, Response Filed on Mar. 21, 2017 to Extended European Search Report dated Aug. 22, 2016", 18 pgs.

"International Application Serial No. PCT/US2016/022907, International Preliminary Report on Patentability dated Oct. 5, 2017", 9 pgs.

"U.S. Appl. No. 15/073,167, Non Final Office Action dated Nov. 23, 2018", 16 pgs.

"U.S. Appl. No. 15/073,167, Response filed Feb. 1, 2019 to Non Final Office Action dated Nov. 23, 2018", 16 pgs.

"U.S. Appl. No. 16/162,530, Preliminary Amendment filed Nov. 14, 2018", 5 pgs.

"European Application Serial No. 16781218.9, Response Filed Dec. 13, 2018 to Communication pursuant to Rules 161(2) and 162 EPC dated Jun. 7, 2018", 15 pgs.

"Answer filed Dec. 1, 2010 of Zimmer, Inc and Zimmer Technology, Inc", *W. Norman Scott and Giles R Scuderi* vs. *Zimmer, Inc and Zimmer Technology, Inc* in the US District Court of Delaware in Case No. 10-772-GMS, (Dec. 1, 2010), 36 pgs.

"U.S. Appl. No. 11/611,021, Advisory Action dated Jan. 22, 2016", 3 pgs.

"U.S. Appl. No. 11/611,021, Examiner Interview Summary dated Jun. 30, 2016", 3 pgs.

"U.S. Appl. No. 11/611,021, Final Office Action dated Mar. 10, 2011", 7 pgs.

"U.S. Appl. No. 11/611,021, Final Office Action dated Sep. 25, 2014", 9 pgs.

"U.S. Appl. No. 11/611,021, Final Office Action dated Nov. 6, 2015", 11 pgs.

(56) References Cited

OTHER PUBLICATIONS

"U.S. Appl. No. 11/611,021, Non Final Office Action dated Jan. 17, 2014", 11 pgs.
"U.S. Appl. No. 11/611,021, Non Final Office Action dated Apr. 8, 2016", 11 pgs.
"U.S. Appl. No. 11/611,021, Non Final Office Action dated Jun. 17, 2015", 12 pgs.
"U.S. Appl. No. 11/611,021, Non Final Office Action dated Jul. 21, 2010", 8 pgs.
"U.S. Appl. No. 11/611,021, Non-Final Office Action dated Dec. 7, 2009", 4 pgs.
"U.S. Appl. No. 11/611,021, Preliminary Amendment filed Oct. 26, 2007", 7 pgs.
"U.S. Appl. No. 11/611,021, Response filed Jan. 4, 2016 to Final Office Action dated Nov. 6, 2015", 12 pgs.
"U.S. Appl. No. 11/611,021, Response filed Feb. 24, 2015 to Final Office Action dated Sep. 25, 2014", 16 pgs.
"U.S. Appl. No. 11/611,021, Response filed May 3, 2010 to Non Final Office Action dated Dec. 7, 2009", 14 pgs.
"U.S. Appl. No. 11/611,021, Response filed Jun. 6, 2011 Final Office Action dated Mar. 10, 2011", 8 pgs.
"U.S. Appl. No. 11/611,021, Response filed Jul. 15, 2014 to Non-Final Office Action dated Jan. 17, 2014", 19 pgs.
"U.S. Appl. No. 11/611,021, Response filed Aug. 5, 2016 to Non Final Office Action dated Apr. 8, 2016", 18 pgs.
"U.S. Appl. No. 11/611,021, Response filed Aug. 25, 2015 to Non Final Office Action dated Jun. 17, 2015", 14 pgs.
"U.S. Appl. No. 11/611,021, Response filed Dec. 21, 2010 to Non Final Office Action dated Jul. 21, 2010", 14 pgs.
"U.S. Appl. No. 11/780,248, Non Final Office Action dated Feb. 4, 2010", 4 pgs.
"U.S. Appl. No. 11/780,248, Non Final Office Action dated Jul. 21, 2010", 11 pgs.
"U.S. Appl. No. 11/780,248, Response filed May 3, 2010 to Non Final Office Action dated Feb. 4, 2010", 13 pgs.
"U.S. Appl. No. 12/974,018, Appeal Brief filed Feb. 20, 2015", 24 pgs.
"U.S. Appl. No. 12/974,018, Final Office Action dated Apr. 13, 2012", 11 pgs.
"U.S. Appl. No. 12/974,018, Final Office Action dated Oct. 10, 2014", 12 pgs.
"U.S. Appl. No. 12/974,018, Non Final Office Action dated Apr. 4, 2014", 11 pgs.
"U.S. Appl. No. 12/974,018, Non Final Office Action dated Nov. 10, 2011", 5 pgs.
"U.S. Appl. No. 12/974,018, Preliminary Amendment filed Dec. 21, 2010", 4 pgs.
"U.S. Appl. No. 12/974,018, Response filed Mar. 8, 2012 to Non Final Office Action dated Nov. 10, 2011", 12 pgs.
"U.S. Appl. No. 12/974,018, Response filed Jul. 30, 2014 to Non-Final Office Action dated Apr. 4, 2014", 15 pgs.
"U.S. Appl. No. 12/974,018, Response filed Oct. 12, 2012 to Final Office Action dated Apr. 13, 2012", 16 pgs.
"U.S. Appl. No. 13/161,624, Notice of Allowance dated Mar. 12, 2013", 11 pgs.
"U.S. Appl. No. 13/161,624, Response filed Feb. 26, 2013 to Restriction Requirement dated Sep. 26, 2012", 9 pgs.
"U.S. Appl. No. 13/161,624, Restriction Requirement dated Sep. 26, 2012", 8 pgs.
"U.S. Appl. No. 13/459,060, Advisory Action dated Jun. 8, 2015", 3 pgs.
"U.S. Appl. No. 13/459,060, Final Office Action dated Apr. 1, 2015", 11 pgs.
"U.S. Appl. No. 13/459,060, Non Final Office Action dated Mar. 14, 2014", 8 pgs.
"U.S. Appl. No. 13/459,060, Non Final Office Action dated Oct. 9, 2014", 11 pgs.
"U.S. Appl. No. 13/459,060, Notice of Allowance dated Dec. 7, 2015", 7 pgs.
"U.S. Appl. No. 13/459,060, Preliminary Amendment filed Apr. 27, 2012", 6 pgs.
"U.S. Appl. No. 13/459,060, PTO Response to Rule 312 Communication dated Mar. 3, 2016", 2 pgs.
"U.S. Appl. No. 13/459,060, Response filed Jan. 3, 2014 to Restriction Requirement dated Nov. 4, 2013", 25 pgs.
"U.S. Appl. No. 13/459,060, Response filed Feb. 18, 2015 to Non-Final Office Action dated Oct. 9, 2014", 23 pgs.
"U.S. Appl. No. 13/459,060, Response filed May 28, 2015 to Final Office Action dated Apr. 1, 2015", 21 pgs.
"U.S. Appl. No. 13/459,060, Response filed Jul. 14, 2014 to Non-Final Office Action dated Mar. 14, 2014", 30 pgs.
"U.S. Appl. No. 13/459,060, Restriction Requirement dated Nov. 4, 2013", 6 pgs.
"U.S. Appl. No. 13/459,061, Advisory Action dated Sep. 30, 2014", 3 pgs.
"U.S. Appl. No. 13/459,061, Final Office Action dated Jul. 23, 2014", 10 pgs.
"U.S. Appl. No. 13/459,061, Non Final Office Action dated Mar. 26, 2014", 8 pgs.
"U.S. Appl. No. 13/459,061, Non Final Office Action dated Nov. 10, 2014", 9 pgs.
"U.S. Appl. No. 13/459,061, Notice of Allowance dated Feb. 27, 2015", 8 pgs.
"U.S. Appl. No. 13/459,061, Preliminary Amendment filed Apr. 27, 2012", 6 pgs.
"U.S. Appl. No. 13/459,061, Response filed Jan. 10, 2014 to Restriction Requirement dated Nov. 12, 2013", 8 pgs.
"U.S. Appl. No. 13/459,061, Response filed Feb. 10, 2015 to Non Final Office Action dated Nov. 10, 2014", 12 pgs.
"U.S. Appl. No. 13/459,061, Response filed Jun. 25, 2014 to Non Final Office Action dated Mar. 26, 2014", 11 pgs.
"U.S. Appl. No. 13/459,061, Response filed Sep. 19, 2014 to Final Office Action dated Jul. 23, 2014", 9 pgs.
"U.S. Appl. No. 13/459,061, Restriction Requirement dated Nov. 12, 2013", 5 pgs.
"U.S. Appl. No. 13/459,064, Final Office Action dated Jun. 13, 2014", 10 pgs.
"U.S. Appl. No. 13/459,064, Non Final Office Action dated Mar. 6, 2014", 8 pgs.
"U.S. Appl. No. 13/459,064, Notice of Allowance dated Aug. 28, 2014", 8 pgs.
"U.S. Appl. No. 13/459,064, Preliminary Amendment filed Apr. 27, 2012", 6 pgs.
"U.S. Appl. No. 13/459,064, PTO Response to Rule 312 Communication dated Dec. 15, 2014", 2 pgs.
"U.S. Appl. No. 13/459,064, Response filed Jan. 27, 2014 to Restriction Requirement dated Nov. 25, 2013", 13 pgs.
"U.S. Appl. No. 13/459,064, Response filed Jun. 3, 2014 to Non-Final Office action dated Mar. 6, 2014", 13 pgs.
"U.S. Appl. No. 13/459,064, Response filed Aug. 13, 2014 to Final Office Action dated Jun. 13, 2014", 13 pgs.
"U.S. Appl. No. 13/459,064, Restriction Requirement dated Nov. 25, 2013", 5 pgs.
"U.S. Appl. No. 13/819,528, Advisory Action dated Apr. 14, 2015", 3 pgs.
"U.S. Appl. No. 13/819,528, Final Office Action dated Feb. 5, 2015", 15 pgs.
"U.S. Appl. No. 13/819,528, Non Final Office Action dated Aug. 12, 2014", 10 pgs.
"U.S. Appl. No. 13/819,528, Non Final Office Action dated Dec. 6, 2013", 15 pgs.
"U.S. Appl. No. 13/819,528, Notice of Allowance dated Jun. 22, 2015", 7 pgs.
"U.S. Appl. No. 13/819,528, Preliminary Amendment filed Feb. 27, 2013", 9 pgs.
"U.S. Appl. No. 13/819,528, Response filed Jan. 12, 2015 to Non Final Office Action dated Aug. 12, 2014", 13 pgs.
"U.S. Appl. No. 13/819,528, Response filed Apr. 2, 2015 to Final Office Action dated Feb. 5, 2015", 12 pgs.
"U.S. Appl. No. 13/819,528, Response filed Apr. 29, 2015 to Advisory Action dated Apr. 14, 2015", 13 pgs.

(56) References Cited

OTHER PUBLICATIONS

"U.S. Appl. No. 13/819,528, Response filed May 22, 2014 to Non Final Office Action dated Dec. 6, 2013", 15 pgs.
"U.S. Appl. No. 13/819,528, Supplemental Preliminary Amendment filed Jul. 11, 2013", 6 pgs.
"U.S. Appl. No. 14/014,737, Advisory Action dated Oct. 23, 2014", 3 pgs.
"U.S. Appl. No. 14/014,737, Appeal Brief filed Feb. 12, 2015", 12 pgs.
"U.S. Appl. No. 14/014,737, Final Office Action dated Aug. 15, 2014", 5 pgs.
"U.S. Appl. No. 14/014,737, Non Final Office Action dated May 6, 2014", 6 pgs.
"U.S. Appl. No. 14/014,737, Pre-Appeal Brief Request filed Nov. 14, 2014", 4 pgs.
"U.S. Appl. No. 14/014,737, Preliminary Amendment filed Nov. 6, 2013", 7 pgs.
"U.S. Appl. No. 14/014,737, Response filed Aug. 6, 2014 to Non-Final Office Action dated May 6, 2014", 8 pgs.
"U.S. Appl. No. 14/014,737, Response filed Oct. 15, 2014 to Final Office Action dated Aug. 15, 2014", 8 pgs.
"U.S. Appl. No. 14/525,595, Application filed Oct. 28, 2014", 40 pgs.
"U.S. Appl. No. 14/553,034, Non Final Office Action dated Apr. 20, 2016", 15 pgs.
"U.S. Appl. No. 14/553,034, Preliminary Amendment filed Mar. 13, 2015", 10 pgs.
"U.S. Appl. No. 14/553,034, Response filed Aug. 22, 2016 to Non Final Office Action dated Apr. 20, 2016", 10 pgs.
"U.S. Appl. No. 14/731,013, Supplemental Preliminary Amendment filed Jun. 18, 2015", 5 pgs.
"U.S. Appl. No. 14/809,810, Advisory Action dated Jun. 27, 2018", 3 pgs.
"U.S. Appl. No. 14/809,810, Corrected Notice of Allowability dated Aug. 30, 2018", 2 pgs.
"U.S. Appl. No. 14/809,810, Final Office Action dated May 2, 2018", 10 pgs.
"U.S. Appl. No. 14/809,810, Non Final Office Action dated Sep. 29, 2017", 9 pgs.
"U.S. Appl. No. 14/809,810, Notice of Allowance dated Aug. 15, 2018", 7 pgs.
"U.S. Appl. No. 14/809,810, Response Filed Jun. 15, 2018 to Final Office Action dated May 2, 2018", 14 pgs.
"U.S. Appl. No. 14/809,810, Response filed Dec. 27, 2017 to Non Final Office Action dated Sep. 29, 2017", 14 pgs.
"U.S. Appl. No. 14/845,522, Non Final Office Action dated Jun. 1, 2016", 11 pgs.
"U.S. Appl. No. 14/845,522, Preliminary Amendment filed Sep. 24, 2015", 7 pgs.
"U.S. Appl. No. 14/845,522, Response filed Sep. 1, 2016 to Non Final Office Action dated Jun. 1, 2016", 14 pgs.
"U.S. Appl. No. 15/092,107, Preliminary Amendment filed Apr. 7, 2016", 11 pgs.
"U.S. Appl. No. 15/267,826, Non Final Office Action dated Apr. 5, 2018", 8 pgs.
"U.S. Appl. No. 15/267,826, Response filed Feb. 22, 2018 to Restriction Requirement dated Dec. 27, 2017", 6 pgs.
"U.S. Appl. No. 15/267,826, Response filed Jun. 26, 2018 to Non Final Office Action dated Apr. 5, 2018", 9 pgs.
"U.S. Appl. No. 15/267,826, Restriction Requirement dated Dec. 27, 2017", 6 pgs.
"U.S. Appl. No. 61/381,803, filed Sep. 10, 2010", 23 pgs.
"Australian Application Serial No. 2006325787, Office Action dated Mar. 14, 2012", 2 pgs.
"Australian Application Serial No. 2006325787, Office Action dated Nov. 14, 2011", 2 pgs.
"Australian Application Serial No. 2006325787, Response filed May 3, 2013 to Office Action dated Mar. 14, 2012", 10 pgs.
"Australian Application Serial No. 2006325787, Response filed Feb. 21, 2012 to Office Action dated Nov. 14, 2011", 34 pgs.
"Australian Application Serial No. 2012271153, Amendment filed Jan. 16, 2014", 13 pgs.
"Australian Application Serial No. 2012271186, First Examiner Report dated Dec. 15, 2015", 3 pgs.
"Australian Application Serial No. 2012271186, Response filed Jun. 24, 2016 to First Examiner Report dated Dec. 15, 2015", 14 pgs.
"Australian Application Serial No. 2012271186, Subsequent Examiners Report dated Aug. 2, 2016", 3 pgs.
"Australian Application Serial No. 2012271243, Subsequent Examiners Report dated Apr. 13, 2015", 2 pgs.
"Australian Application Serial No. 2012271244, First Examiner Report dated Dec. 15, 2015", 3 pgs.
"Australian Application Serial No. 2012271244, Response filed Jun. 24, 2016 to First Examiner Report dated Dec. 15, 2015", 13 pgs.
"Australian Application Serial No. 2013245552, First Examiner Report dated Mar. 30, 2016", 4 pgs.
"Canadian Application Serial No. 2,641,966, Office Action dated Feb. 6, 2014", 2 pgs.
"Canadian Application Serial No. 2,641,966, Office Action dated Jul. 16, 2013", 2 pgs.
"Canadian Application Serial No. 2,641,966, Office Action dated Aug. 25, 2014", 2 pgs.
"Canadian Application Serial No. 2,641,966, Office Action dated Sep. 4, 2015", 4 pgs.
"Canadian Application Serial No. 2,641,966, Response filed Jan. 15, 2014 to Office Action dated Jul. 16, 2013", 6 pgs.
"Canadian Application Serial No. 2,641,966, Response filed Feb. 25, 2015 to Office Action dated Aug. 25, 2014", 4 pgs.
"Canadian Application Serial No. 2,641,966, Response filed Aug. 6, 2014 to Office Action dated Feb. 6, 2014", 3 pgs.
"Chinese Application Serial No. 200680046893, Office Action dated Aug. 3, 2012", (W/ English Translation), 8 pgs.
"Chinese Application Serial No. 200680046893, Office Action dated Aug. 10, 2010", (W/ English Translation), 22 pgs.
"Chinese Application Serial No. 200680046893, Office Action dated Dec. 6, 2011", (W/ English Translation), 5 pgs.
"Chinese Application Serial No. 200680046893, Response filed Jan. 23, 2012 to Office Action dated Dec. 6, 2011", (W/ English Translation), 11 pgs.
"Chinese Application Serial No. 200680046893.7, Response filed Oct. 17, 2012 to Office Action dated Aug. 3, 2012", (W/ English Translation), 8 pgs.
"Chinese Application Serial No. 201280039703.4, Office Action dated Mar. 30, 2015", (W/ English Translation), 2 pgs.
"Chinese Application Serial No. 201280039703.4, Office Action dated May 10, 2016", w/English Translation, 8 pgs.
"Chinese Application Serial No. 201280039703.4, Office Action dated May 28, 2015", (W/ English Translation), 12 pgs.
"Chinese Application Serial No. 201280039703.4, Office Action dated Dec. 3, 2015", w/English Translation, 8 pgs.
"Chinese Application Serial No. 201280039703.4, Response filed Feb. 1, 2016 to Office Action dated Dec. 3, 2015", w/English Claims, 24 pgs.
"Chinese Application Serial No. 201280039703.4, Response filed May 31, 2016 to Office Action dated May 10, 2016", (W/ English Translation), 34 pgs.
"Chinese Application Serial No. 201280039703.4, Response filed Sep. 7, 2015 to Office Action dated May 28, 2015", (W/ English Translation), 72 pgs.
"Chinese Application Serial No. 201280039705.3, Office Action dated Mar. 20, 2015", (W/ English Translation), 15 pgs.
"Chinese Application Serial No. 201280039705.3, Response filed Aug. 6, 2015 to Office Action dated Mar. 20, 2015", (W/ English translation of claims), 11 pgs.
"Chinese Application Serial No. 201280039705.3, Voluntary Amendment filed Jul. 22, 2014", w/English Claims, 9 pgs.
"Chinese Application Serial No. 201280039706.8, Office Action dated Feb. 26, 2016", W/ English Translation, 4 pgs.
"Chinese Application Serial No. 201280039706.8, Office Action dated May 19, 2015", (W/ English Translation), 14 pgs.
"Chinese Application Serial No. 201280039706.8, Response filed May 11, 2016 to Office Action dated Feb. 26, 2016", W/ English Translation of Claims, 9 pgs.

(56) References Cited

OTHER PUBLICATIONS

"Chinese Application Serial No. 201280039706.8, Response filed Nov. 16, 2015 to Office Action dated May 19, 2015", W/ English Translation of Claims, 16 pgs.

"Chinese Application Serial No. 201280039714.2, Office Action dated May 4, 2015", (W/ English Translation), 19 pgs.

"Chinese Application Serial No. 201280039714.2, Office Action dated Dec. 3, 2015", (W/ English Translation), 7 pgs.

"Chinese Application Serial No. 201280039714.2, Response filed Feb. 1, 2016 to Office Action dated Dec. 3, 2015", w/English Claims, 8 pgs.

"Chinese Application Serial No. 201280039714.2, Response filed Sep. 18, 2015 to Office Action dated May 4, 2015", (W/ English Translation of Claims), 9 pgs.

"Complaint of W. Norman Scot and Giles R. Scuderi filed Sep. 9, 2010", *W. Norman Scott and Giles R Scuderi* vs. *Zimmer, Inc and Zimmer Technology, Inc* in the US District Court of Delaware in Case No. 10-772-GMS, (Sep. 9, 2010), 24 pgs.

"European Application Serial No. 06840269.2, Decision to Grant dated Feb. 18, 2016", 3 pgs.

"European Application Serial No. 06840269.2, Examination Notification Art. 94(3) dated Jan. 24, 2014", 6 pgs.

"European Application Serial No. 06840269.2, Examination Notification Art. 94(3) dated Nov. 12, 2014", 4 pgs.

"European Application Serial No. 06840269.2, Office Action dated Sep. 8, 2015", 67 pgs.

"European Application Serial No. 06840269.2, Response filed Mar. 23, 2015 to Examination Notification Art. 94(3) dated Nov. 12, 2014", 10 pgs.

"European Application Serial No. 06840269.2, Response filed Aug. 4, 2014 to Examination Notification Art. 94(3) dated Jan. 24, 2014", 10 pgs.

"European Application Serial No. 12720354.5, Decision of Grant dated Dec. 3, 2015", 3 pgs.

"European Application Serial No. 12720354.5, Examination Notification Art. 94(3) dated Oct. 22, 2014", 4 pgs.

"European Application Serial No. 12720354.5, Office Action dated Jun. 17, 2015", 96 pgs.

"European Application Serial No. 12720354.5, Response filed Aug. 21, 2014 to Communication pursuant to Rules 161(2) and 162 EPC dated Feb. 14, 2014", 17 pgs.

"European Application Serial No. 12720354.5, Response filed Dec. 24, 2014 to Examination Notification Art. 94(3) dated Oct. 22, 2014", 13 pgs.

"European Application Serial No. 12722967.2, Examination Notification Art. 94(3) dated Oct. 22, 2014", 4 pgs.

"European Application Serial No. 12724484.6, Communication Pursuant to Article 94(3) EPC dated May 2, 2016", 5 pgs.

"European Application Serial No. 12724484.6, Examination Notification Art. 94(3) dated Dec. 3, 2014", 5 pgs.

"European Application Serial No. 12724484.6, Response filed Apr. 13, 2015 to Examination Notification Art. 94(3) dated Dec. 3, 2014", 16 pgs.

"European Application Serial No. 12724484.6, Response filed Aug. 20, 2014 to Communication pursuant to Rules 161(1) and 162 EPC dated Feb. 14, 2014", 10 pgs.

"European Application Serial No. 14200265.8, Extended European Search Report dated Aug. 22, 2016", 23 pgs.

"European Application Serial No. 15180629.6, Extended European Search Report dated Aug. 24, 2016", 8 pgs.

"Gender Solutions Natural-Knee Flex System", Zimmer, Inc., (2007, 2009), 6 pgs.

"Gender Solutions Natural-Knee Flex System: Surgical Technique", Zimmer, Inc., (2007, 2008, 2009), 36 pgs.

"Gender Solutions Patello-Femoral Joint (PFJ) System: Surgical Technique", Zimmer Inc., (2008, 2009), 38 pgs.

"International Application Serial No. PCT/EP2011/004556, International Preliminary Report on Patentability dated Mar. 12, 2013", 9 pgs.

"International Application Serial No. PCT/EP2011/004556, International Search Report dated Feb. 9, 2012", 6 pgs.

"International Application Serial No. PCT/EP2011/004556, Written Opinion dated Mar. 12, 2013", 9 pgs.

"International Application Serial No. PCT/US2006/062117, International Preliminary Report on Patentability dated Jun. 18, 2008", 5 pgs.

"International Application Serial No. PCT/US2006/062117, Written Opinion dated Apr. 5, 2007", 4 pgs.

"International Application Serial No. PCT/US2012/035688, International Preliminary Report on Patentability dated Jan. 3, 2014", 13 pgs.

"International Application Serial No. PCT/US2012/035688, Partial Search Report dated Jul. 3, 2012", 8 pgs.

"International Application Serial No. PCT/US2012/035688, Search Report dated Sep. 17, 2012", 7 pgs.

"International Application Serial No. PCT/US2012/035688, Written Opinion dated Sep. 17, 2012", 11 pgs.

"International Application Serial No. PCT/US2012/035691, International Preliminary Report on Patentability dated Jan. 3, 2014", 13 pgs.

"International Application Serial No. PCT/US2012/035691, Partial Search Report dated Jul. 10, 2012", 8 pgs.

"International Application Serial No. PCT/US2012/035691, Search Report dated Sep. 17, 2012", 7 pgs.

"International Application Serial No. PCT/US2012/035691, Written Opinion dated Sep. 17, 2012", 11 pgs.

"International Application Serial No. PCT/US2012/035693, International Preliminary Report on Patentability dated Jan. 3, 2014", 13 pgs.

"International Application Serial No. PCT/US2012/035693, Partial Search Report dated Jun. 27, 2012", 8 pgs.

"International Application Serial No. PCT/US2012/035693, Search Report dated Oct. 9, 2012", 7 pgs.

"International Application Serial No. PCT/US2012/035693, Written Opinion dated Oct. 9, 2012", 11 pgs.

"International Application Serial No. PCT/US2012/038531, International Preliminary Report on Patentability dated Jan. 3, 2014", 12 pgs.

"International Application Serial No. PCT/US2012/038531, International Search Report dated Oct. 8, 2012", 14 pgs.

"International Application Serial No. PCT/US2012/038531, Written Opinion dated Oct. 8, 2012", 10 pgs.

"International Application Serial No. PCT/US2016/022907, International Search Report dated Jul. 7, 2016", 7 pgs.

"International Application Serial No. PCT/US2016/022907, Written Opinion dated Jul. 7, 2016", 13 pgs.

"International Application Serial No. PCT/US2016/052173, International Preliminary Report on Patentability dated Apr 12, 2018", 8 pgs.

"International Application Serial No. PCT/US2016/052173, International Search Report dated Jan. 10, 2017", 6 pgs.

"International Application Serial No. PCT/US2016/052173, Written Opinion dated Jan. 10, 2017", 7 pgs.

"Japanese Application Serial No. 2008-545981, Examiners Decision of Final Refusal dated Oct. 16, 2012", (W/ English Translation), 3 pgs.

"Japanese Application Serial No. 2008-545981, Office Action dated Apr. 17, 2012", (W/ English Translation), 5 pgs.

"Japanese Application Serial No. 2008-545981, Office Action dated Jul. 5, 2011", (W/ English Translation), 13 pgs.

"Japanese Application Serial No. 2008-545981, Response filed Oct. 5, 2011 to Office Action dated Jul. 5, 2011", (W/ English Translation), 6 pgs.

"Japanese Application Serial No. 2008-545981, Response filed Aug. 30, 2012 to Office Action dated Apr. 17, 2012", (W/ English Translation), 5 pgs.

"Japanese Application Serial No. 2011-221305, Office Action dated Feb. 26, 2013", (W/ English Translation), 13 pgs.

"Japanese Application Serial No. 2011-221305, Office Action dated Sep. 17, 2013", (W/ English Translation), 5 pgs.

(56) References Cited

OTHER PUBLICATIONS

"Japanese Application Serial No. 2011-221305, Response filed Aug. 26, 2013 to Office Action dated Feb. 26, 2013", (W/ English Translation), 9 pgs.
"Japanese Application Serial No. 2011-221305, Response filed Dec. 17, 2013 to Office Action dated Sep. 17, 2013", (W/ English Translation of Claims), 8 pgs.
"Japanese Application Serial No. 2014-515819, Notice of Allowance dated Dec. 15, 2015", W/ English Translation), 13 pgs.
"Japanese Application Serial No. 2014-515819, Office Action dated Feb. 3, 2015", (W/ English Translation), 15 pgs.
"Japanese Application Serial No. 2014-515819, Response filed Jul. 29, 2015 to Office Action dated Feb. 3, 2015", (W/ English translation of claims), 11 pgs.
"Japanese Application Serial No. 2014-515820, Office Action dated Dec. 2, 2014", (W/ English Translation), 8 pgs.
"Japanese Application Serial No. 2014-515821, Request for Examination Amendment filed Apr. 8, 2014", (W/ English Translation), 18 pgs.
"Japanese Application Serial No. 2014-515831, Office Action dated Dec. 16, 2014", (W/ English Translation), 12 pgs.
"Japanese Application Serial No. 2015-124808, Amendment filed Jul. 16, 2015", (W/ English Translation), 8 pgs.
"Japanese Application Serial No. 2015-124808, Office Action dated Jun. 7, 2016", (W/ English Translation), 5 pgs.
"LPS-Flex Fixed Bearing Knee: Surgical Technique", Zimmer, Inc., (2004, 2007, 2008), 16 pgs.
"Natural-Knee® Modular Cemented Baseplate", [Online] retrieved from the Internet: URL: http://www.zimmer.com/content/dam/zimmer-web/documents/en-US/pdf/medical-professionals/knee/natural-knee-modular-cemented-baseplate-brochure.pdf, (2004), 4 pgs.
"Nexgen Complete Knee Solution", Extramedullary/Intramedullary Tibial Resector: Surgical Technique, Zimmer, Inc. 97-5997-02 Rev 1, (2000), 26 pgs.
"NexGen Implant Options Surgeon-Specific", Zimmer Inc., (2000), 16 pgs.
"NexGen LPS Fixed Knee: Surgical Technique", Zimmer Inc., (2002, 2008), 44 pgs.
"NexGen LPS-Flex Mobile and LPS-Mobile Bearing Knees", Zimmer, Inc., (2007, 2008), 4 pgs.
"Surgical Technique for the CR-Flex Fixed Bearing Knee", NexGen Complete Knee Solution, Zimmer, Inc., (2003), 22 pgs.
"Unicompartmental High Flex Knee: Intramedullary, Spacer Block Option and Extramedullary Minimally Invasive Surgical Techniques", Zimmer, Inc., (2004, 2009, 2010), 62 pgs.
Hitt, Kirby, et al., "Anthropometric Measurements of the Human Knee: Correlation to the Sizing of Current Knee Arthroplasty Systems", The Journal of Bone & Joint Surgery, (2003), 114-122.
Mensch, Joseph S, et al., "Knee Morphology as a Guide to Knee Replacement", Clinical Orthopaedics and Related Research No. 112, (Oct. 1975), 231-241.
Poilvache, Pascal L, et al., "Rotational Landmarks and Sizing of the Distal Femur in Total Knee Arthroplasty", Clinical Orthopaedics and Related Research, No. 331, (1996), 35-46.
Seedhom, B B, et al., "Dimensions of the Knee—Radiographic and Autopsy Study of Sizes Required for a Knee Prosthesis", Annals of the Rheumatic Diseases, (1972), 54-58.
Yoshioka, Yuki, et al., "The Anatomy and Functional Axes of the Femur", The Journal of Bone and Joint Surgery, vol. 69A, No. 6, (Jul. 1987), 873-880.
"U.S. Appl. No. 15/073,167, Advisory Action dated May 17, 2019", 4 pgs,.
"U.S. Appl. No. 15/073,167, Advisory Action dated Jun. 4, 2019", 3 pgs.
"U.S. Appl. No. 15/073,167, Final Office Action dated Mar. 14, 2019", 18 pgs.
"U.S. Appl. No. 15/073,167, Notice of Allowability dated Jan. 13, 2010", 3 pgs.
"U.S. Appl. No. 15/073,167, Notice of Allowance dated Oct. 30, 2019", 6 pgs.
"U.S. Appl. No. 15/073,167, Response filed Jun. 14, 2019 to Advisory Action dated Jun. 4, 2019", 16 pgs.
"U.S. Appl. No. 15/073,167, Response filed May 13, 2019 to Final Office Action dated Mar. 14, 2019", 14 pgs.
"U.S. Appl. No. 16/162,530, Non Final Office Action dated Sep. 16, 2019", 8 pgs.
"U.S. Appl. No. 16/162,530, Notice of Allowance dated Dec. 27, 2019", 7 pgs.
"U.S. Appl. No. 16/162,530, Response filed Dec. 12, 2019 to Non Final Office Action dated Sep. 16, 2019", 10 pgs.
"U.S. Appl. No. 16/829,831, Preliminary Amendment filed May 28, 2020", 6 pgs.
"European Application Serial No. 16781218.9, Communication Pursuant to Article 94(3) EPC dated Feb. 6, 2020", 3 pgs.
"European Application Serial No. 16781218.9, Communication Pursuant to Article 94(3) EPC dated May 9, 2019", 4 pgs.
"European Application Serial No. 16781218.9, Response filed Sep. 19, 2019 to Communication Pursuant to Article 94(3) EPC dated May 9, 2019", 16 pgs.
U.S. Appl. No. 16/162,530, filed Oct. 17, 2018, Tibial Prosthesis for Tibia With Varus Resection.
U.S. Appl. No. 16/829,831, filed Mar. 25, 2020, Tibial Prosthesis for Tibia With Varus Resection.
U.S. Appl. No. 14/809,810, filed Jul. 27, 2015, Instruments and Methods in Performing Kinematically-Aligned Total Knee Arthroplasty.
U.S. Appl. No. 15/073,167, filed Mar. 17, 2016, Disposable Multi-Purpose Tool for Total Knee Arthroplasty.
U.S. Appl. No. 15/267,826, filed Sep. 16, 2016, Tibial Prosthesis for Tibia With Varus Resection.

\* cited by examiner

INSTRUMENTS AND METHODS IN PERFORMING KINEMATICALLY-ALIGNED TOTAL KNEE ARTHROPLASTY

CLAIM OF PRIORITY

This application is a continuation of U.S. patent application Ser. No. 14/809,810, filed Jul. 27, 2015, which claims the benefit of U.S. Provisional Patent Application Ser. No. 62/031,572, filed on Jul. 31, 2014, the benefit of priority of each of which is claimed hereby, and which are incorporated by reference herein in its entirety.

TECHNICAL FIELD

The present patent application relates to orthopedic prostheses, and, more particularly, to systems and methods for use in performing a total knee arthroplasty.

BACKGROUND

Orthopedic prostheses are commonly utilized to repair and/or replace damaged bone and tissue in the human body. For example, a knee prosthesis may be used to restore natural knee function by repairing damaged or diseased articular surfaces of the femur and/or tibia. Knee prostheses may include a femoral component implanted on the distal end of the femur, which articulates with a tibial component implanted on the proximal end of a tibia to replicate the function of a healthy natural knee.

Osteoarthritis, a degenerative joint disease initiated through the loss of articular cartilage, may necessitate a knee replacement. A number of causes, including hereditary, lifestyle, mechanical deficits, and others, may lead to osteoarthritis. The conventional assumption was to restore a patient's leg during the arthroplasty procedure to achieve a neutral mechanical alignment, even if the individual's original or constitutional state was set in varus or valgus.

OVERVIEW

The present inventors recognize, among other things, an opportunity for improved patient satisfaction following a total knee arthroplasty (TKA) through the use of a kinematically aligned TKA and surgical instruments to aid in the procedure.

To further illustrate the systems and methods disclosed herein, the following non-limiting examples are provided:

In Example 1, a system for performing a total knee arthroplasty can comprise a reference block and a plurality of shims. The reference block can be configured for attachment to a distal surface of the femur and connection with a distal femoral cut guide configured to resect the distal medial and lateral condyles. The reference block can set a position of the resections on the distal medial and lateral condyles when attached to the femur. Each shim of the plurality of shims can be attachable to or integral with the reference block. Each shim can be configured for contact with one or both of the distal surfaces of the medial and lateral condyles of the femur. A particular shim can be selected for use from the plurality of shims based on matching at least one of the medial and lateral thicknesses of the selected shim with a determined wear of cartilage on at least one of the distal medial and lateral condyles.

In Example 2, the system of Example 1 can optionally be configured such that the plurality of shims can comprise both medial side shims and lateral side shims, and wherein the medial side shims and lateral side shims can comprise separate components from one another and each of the medial side shims and each of the lateral side shims can be configured for attachment to one of a medial side or a lateral side of the reference block.

In Example 3, the system of Example 1 can optionally be configured such that least one of the plurality of shims can have a medial thickness different from a lateral thickness for that particular shim.

In Example 4, the system of Example 3 can optionally be configured such that the reference block includes four reference blocks, the plurality of shims includes four shims, and each of the shims and a corresponding one of the four reference blocks are monolithic to form four one-piece shim block assemblies.

In Example 5, the system of any one or any combination of Examples 3 to 4 can optionally be configured such that the plurality of shims comprises a first shim having a first medial thickness equal to a first lateral thickness and configured for use on a femur having little to no wear on the distal medial and lateral condyles, a second shim having a second medial thickness equal to a second lateral thickness and greater than the first medial thickness of the first shim, the second shim configured for use on a femur having cartilage wear on both the distal medial and lateral condyles, a third shim having a third medial thickness less than a third lateral thickness and generally equal to the first medial thickness of the first shim, the third shim configured for use on a femur having cartilage wear on a distal lateral condyle, and a fourth shim having a fourth medial thickness greater than a fourth lateral thickness and greater than the first medial thickness of the first shim, the fourth shim configured for use on a femur having cartilage wear on a distal medial condyle.

In Example 6, the system of Example 5 can optionally be configured such that the second medial and lateral thicknesses of the second shim are about 2 mm greater than the first medial and lateral thicknesses of the first shim.

In Example 7, the system of any one or any combination of Examples 5 to 6 can optionally be configured such that the third lateral thickness of the third shim is about 2 mm greater than the third medial thickness of the third shim, and the fourth medial thickness of the fourth shim is about 2 mm greater than the fourth lateral thickness of the fourth shim.

In Example 8, the system of any one or any combination of Examples 1 to 7 can optionally be configured such that the plurality of shims includes at least three shims and each shim is removably attachable to the reference block.

In Example 9, the system of Example 8 can optionally be configured such that the plurality of shims comprises a first shim having a first medial thickness equal to a first lateral thickness and configured for use on a femur having little to no wear on one or both of the distal medial and lateral condyles, a second shim having a second medial thickness equal to a second lateral thickness and greater than the first medial thickness of the first shim, the second shim configured for use on a femur having cartilage wear on one or both the distal and medial lateral condyles, and a third shim having a third medial thickness less than a third lateral thickness and generally equal to the first medial thickness of the first shim, the third shim configured for use on a femur having cartilage wear on a distal lateral condyle.

In Example 10, the system of Example 9 can optionally be configured such that the third shim is configured for use on a femur having cartilage wear on a distal medial condyle by rotating the shim 180 degrees such that the medial portion of the shim is configured for placement on the lateral condyle of the distal femur and the lateral portion of the shim is configured for placement on the medial condyle of the distal femur.

In Example 11, the system of any one or any combination of Examples 9 to 10 can optionally be configured such that the second medial and lateral thicknesses of the second shim are about 2 mm greater than the first medial and lateral thicknesses of the first shim, and the third medial thickness of the third shim is about 2 mm less than the third lateral shim.

In Example 12, the system of any one or any combination of Examples 1-11 can optionally further comprise one or more spacers insertable on a bone contacting side of a cut block configured to resect a posterior portion of the distal femur after resecting the distal medial and lateral condyles.

In Example 13, the system of Example 12 can optionally be configured such that the one or more spacers comprises a first spacer having a thickness of about 1 mm and a second spacer having a thickness of about 2 mm.

In Example 14, a system for performing a total knee arthroplasty can comprise a plurality of shim blocks configured for attachment to a distal surface of the femur and for use with a distal femoral cut guide. Each of the shim blocks can be configured to set a location of bone resections on the distal medial and lateral condyles made using the distal femoral cut guide when the shim block is attached to the femur. Each of the shim blocks can comprise a bone contacting side, an opposing non-bone contacting side, a medial portion, a lateral portion, and at least one opening extending from the bone contacting side to the non-bone contacting side and configured to receive an intramedullary rod. At least one of the plurality of shim blocks can have a medial thickness on the medial portion different from a lateral thickness on the lateral portion for that particular shim block, and a particular shim block can be selected for use in the total knee arthroplasty based on a determined wear of cartilage on the distal medial and lateral condyles.

In Example 15, the system of Example 14 can optionally be configured such that the plurality of shim blocks comprises a first shim block having a first medial thickness equal to a first lateral thickness and configured for use on a femur having little to no wear on the distal medial and lateral condyles, a second shim block having a second medial thickness equal to a second lateral thickness and greater than the first medial thickness of the first shim block, the second shim block configured for use on a femur having cartilage wear on both the distal medial and lateral condyles, a third shim block having a third medial thickness less than a third lateral thickness and generally equal to the first medial thickness of the first shim block, the third shim block configured for use on a femur having cartilage wear on a distal lateral condyle, and a fourth shim block having a fourth medial thickness greater than a fourth lateral thickness and greater than the first medial thickness of the first shim block, the fourth shim block configured for use on a femur having cartilage wear on a distal medial condyle.

In Example 16, the system of Example 15 can optionally be configured such that the second medial and lateral thicknesses of the second shim block are about 2 mm greater than the first medial and lateral thicknesses of the first shim block, the third medial thickness of the third shim block is about 2 mm less than the third lateral thickness of the third shim block, and the fourth medial thickness of the fourth shim block is about 2 mm greater than the fourth lateral thickness of the fourth shim block.

In Example 17, the system of any one or any combination of Examples 15 to 16 can optionally be configured such that each of the shim blocks comprises two apertures formed in a top portion of the shim block and the system can optionally further comprise a guide tower configured to receive the selected shim block prior to attachment of the shim block to the distal surface of the femur.

In Example 18, the system of any one or any combination of Examples 15 to 17 can optionally further comprise one or more spacers insertable on a bone contacting side of a cut block configured to resect a posterior portion of the distal femur after resecting the distal medial and lateral condyles.

In Example 19, a method of performing a total knee arthroplasty can comprise determining cartilage wear on distal medial and lateral condyles of a distal femur, determining a target medial resection thickness and a target lateral resection thickness based on the determined cartilage wear, selecting a shim block assembly from a plurality of shim block assemblies, attaching the shim block assembly to the distal femur, connecting the distal femoral cut guide to the shim block assembly on the distal femur, and resecting the distal medial and lateral condyles. Each shim block assembly can be configured for attachment to a distal surface of the femur and for use with a distal femoral cut guide to set a location of bone resections on at least one of the distal medial and lateral condyles. Each shim block assembly can comprise a bone contacting side, and the particular shim block assembly selected can be based on the determined cartilage wear on one or both of the distal medial and lateral condyles.

In Example 20, the method of Example 19 can optionally include at least one of the shim block assemblies includes both a medial portion and a lateral portion and the at least one of the shim block assemblies can have a medial thickness on the medial portion different from a lateral thickness on the lateral portion for that particular shim block.

In Example 21, the method of any one or any combination of Examples 20 to 21, wherein the shim block assemblies can include both medial side shims and lateral side shims, and wherein the medial side shims and lateral side shims can comprise separate components from one another.

In Example 22, the method of any one or any combination of Examples 19 to 21 can optionally further comprise confirming a thickness of the distal medial resection is about equal to the target medial resection thickness, and confirming a thickness of the distal lateral resection is about equal to the target lateral resection thickness.

In Example 23, the method of any one or any combination of Examples 19 to 22 can optionally be configured such that the plurality of shim block assemblies includes a plurality of shim components and a block assembly, and each shim component can be removably attachable to the block assembly to form a multi-piece shim block assembly.

In Example 24, the method of any one or any combination of Examples 19 to 23 can optionally further comprise resecting a posterior portion of the distal femur.

In Example 25, the method of Example 24 can optionally be configured such that resecting the posterior portion of the distal femur is performed by a cut block, and if a thickness of the distal medial resection is greater than the target medial resection thickness or a thickness of the distal lateral resection is greater than the target lateral resection thickness, the method can optionally further comprise placing one or more spacers on a bone contacting side of the cut block prior to resecting the posterior portion of the distal femur. The one or more spacers can be configured to compensate for a difference between the thickness of the distal medial resection and the target medial resection thickness or a difference between the thickness of the distal lateral resection and the target lateral resection thickness.

In Example 26, the method of any one or any combination of Examples 19-25 can optionally be configured such that the plurality of shim block assemblies comprises a first shim block having a first medial thickness equal to a first lateral thickness and configured for use on a femur having little to no wear on the distal medial and lateral condyles, a second shim block having a second medial thickness equal to a second lateral thickness and greater than the first medial thickness of the first shim block, the second shim block configured for use on a femur having cartilage wear on one or both the distal medial and lateral condyles, a third shim block having a third medial thickness less than a third lateral thickness and generally equal to the first medial thickness of the first shim block, the third shim block configured for use on a femur having cartilage wear on a distal lateral condyle, and a fourth shim block having a fourth medial thickness greater than a fourth lateral thickness and greater than the first medial thickness of the first shim block, the fourth shim block configured for use on a femur having cartilage wear on a distal medial condyle.

In Example 27, the method of Example 26 can optionally be configured such that the second medial and lateral thicknesses of the second shim block are about 2 mm greater than the first medial and lateral thicknesses of the first shim block, the third medial thickness of the third shim block is about 2 mm less than the third lateral thickness of the third shim block, and the fourth medial thickness of the fourth shim block is about 2 mm greater than the fourth lateral thickness of the fourth shim block.

In Example 28, the systems or methods of any one or any combination of Examples 1-27 can optionally be configured such that all elements or options recited are available to use or select from.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

It has been established that a kinematically aligned total knee arthroplasty (TKA) can improve the results of the TKA, including overall patient satisfaction and mobility. Primary goals of kinematically aligned TKA are (1) positioning the femoral and tibial components of a knee prosthesis such that the angles and levels of the distal and posterior femoral and tibial joint lines are restored to the patient's natural joint line, (2) restoration of the patient's natural or constitutional alignment prior to the patient having developed osteoarthritis, and (3) restoration of the patient's natural soft tissue laxity and envelope. The kinematically aligned TKA can include a determination of three kinematic axes.

Figure 1C:
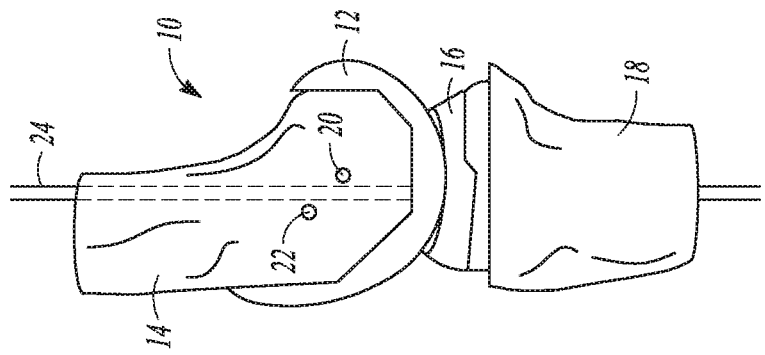
FIG. 1C is a side or sagittal plane view of the knee joint and knee prosthesis of FIGS. 1A and 1B in full extension.
Figure 1B:
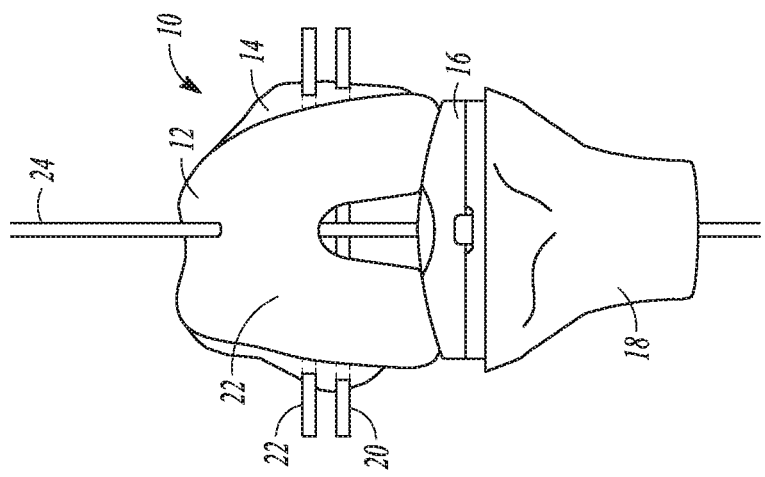
FIG. 1B is a anterior view of the knee joint and knee prosthesis of FIG. 1A in 90 degrees flexion.
Figure 1A:
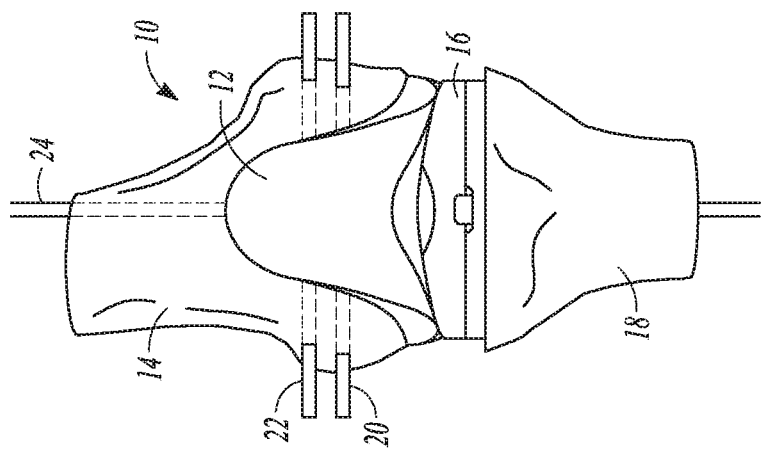
FIG. 1A is an anterior or coronal plane view of a knee joint with an implanted knee prosthesis.

FIGS. 1A-1C show various views of a knee prosthesis 10 implanted on a knee joint and illustrate the three kinematic axes of the knee joint in a kinematically aligned TKA. The knee prosthesis 10 includes a femoral component 12 implanted on a femur 14 and a tibial component 16 implanted on a tibia 18. A polyethylene surface is inserted between the femur and tibia. A first kinematic axis 20 can be a transverse axis in the femur 14 about which the tibia 18 flexes and extends. The first kinematic axis 20 can be determined by projecting the lateral and medial femoral condyles of the femur 14 onto one another and fitting circles of equal radii over each other. The first kinematic axis 20 passes through a center of the circles. A second kinematic axis 22 can be a second transverse axis, parallel to the first kinematic axis 20, about which a patella of the knee joint flexes and extends. The second kinematic axis 22 can be located anterior and proximal to the first kinematic axis 20. A third kinematic axis 24 is an axis perpendicular to the first 20 and second 22 axes about which the tibia 18 internally and externally rotates on the femur 14.

Figure 27:
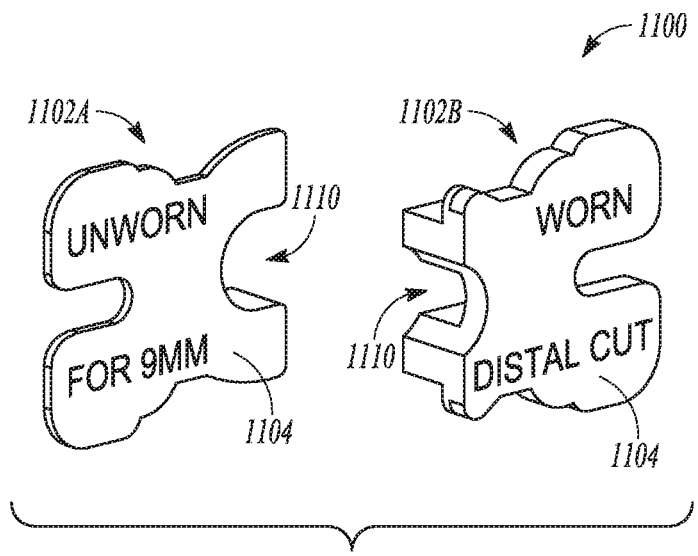
FIG. 27 is perspective view of shim components comprising separate medial and lateral components according to another example of the present application.
Figure 28:
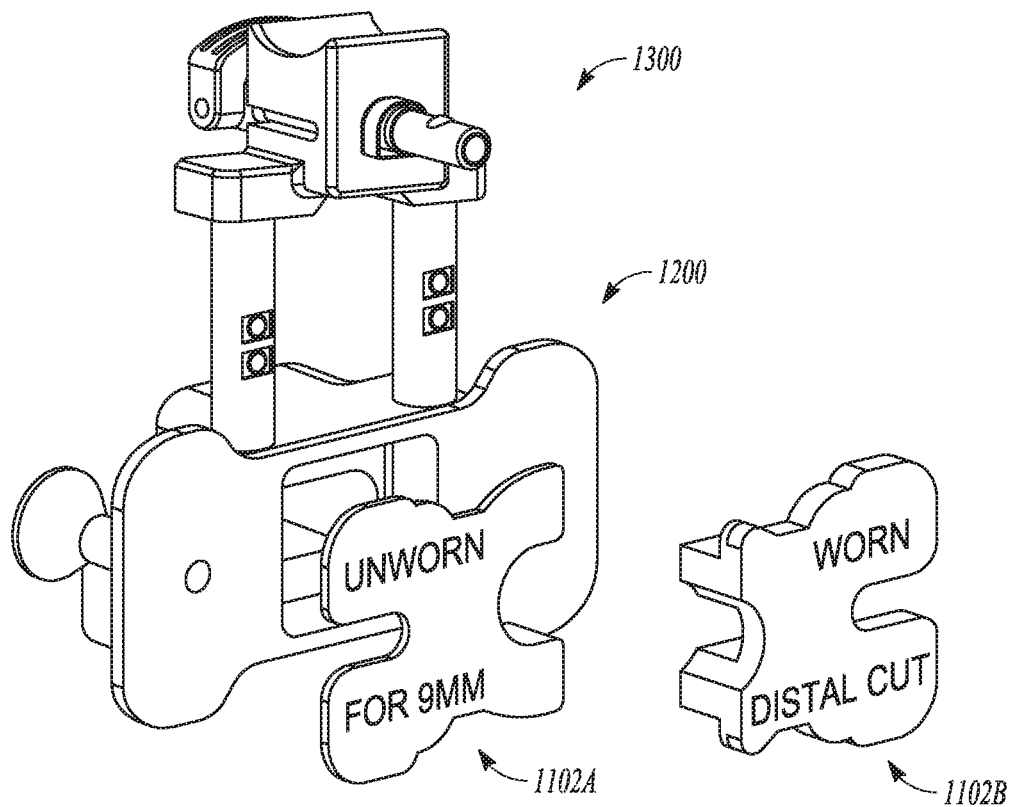
FIG. 28 is a perspective view of the shim components of FIG. 27 positioned adjacent a block assembly according to an example of the present application.

The present application includes a description of the surgical procedure for performing a kinematically aligned TKA. FIGS. 2-11 illustrate examples of surgical instruments and systems that can be used to aid and improve on the kinematically aligned TKA. FIGS. 12-26 illustrate a surgical procedure for the kinematically aligned TKA, including use of the surgical instruments to aid in performing the procedure. FIGS. 27 and 28 illustrate further examples of surgical instruments and systems that can be used to aid and improve on the kinematically aligned TKA.

Typically for an individual with osteoarthritis, the damaged knee can exhibit cartilage wear on one or both sides (medial and/or lateral) of the distal femur. In the kinematically aligned TKA, an objective is to restore the joint line to its pre-arthritic position. Thus the cartilage wear on the distal femur can be accounted for in preparing the distal femur for receiving the femoral prosthesis. The cartilage wear can commonly be on one side of the femoral condyles, medial or lateral, although wear on both sides can occur. The wear can commonly be about 2 mm, resulting in a loss of about 2 mm of cartilage. Typically the wear can be more distal than posterior. If the individual has a varus alignment, then the wear can commonly be on the medial side of the distal femur. If the individual has a valgus alignment, then the wear can commonly be on the lateral side of the distal femur.

The kinematically aligned TKA can include accounting for the cartilage wear on the distal femur. As such, a thickness of the femoral component 12 of the knee prosthesis 10 (see FIGS. 1A-1C) can be equal to the sum of a thickness of the bone resected from the distal femur, a thickness of the worn cartilage and a thickness of the saw blade used to perform the bone resection. Thus, as described below in reference to the surgical procedure, the thicknesses of the four resections to the femur (two distal and two posterior) can be different, relative to one another, depending on the wear determined for a particular patient.

Figure 2:
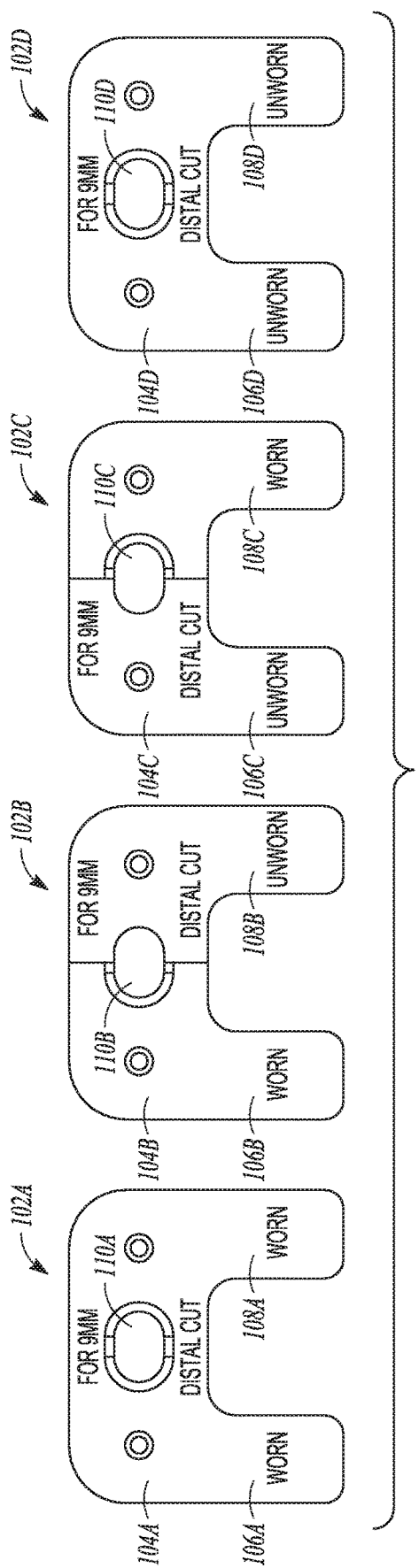
FIG. 2 is a plan view of an example of a set of shim block assemblies in accordance with the present application.

FIG. 2 illustrates an example of a set 100 of shim block assemblies 102A, 102B, 102C and 102D for use in performing the kinematically aligned TKA. The set 100 of shim block assemblies 102A-102D can be used in the surgical procedure to account for wear on the distal femur. Each shim block assembly 102 can include a bone contacting side 104 having a medial portion 106, a lateral portion 108, and an aperture 110 for receiving an intramedullary rod.

In an example, the set 100 can include four shim block assemblies 102A-102D and each of the shim block assemblies 102A-102D can correspond to a particular wear condition on the distal femur of a particular patient. Both of the condyles of the distal femur can be worn, one of the condyles can be worn, or neither of the condyles can be worn. If one or both of the condyles is worn, the corresponding medial 106 and/or lateral 108 portion of the shim block assembly 102 can be thicker, as compared to a medial or lateral portion configured for an unworn condyle, to compensate for the worn cartilage on the distal femur.

FIGS. 2A-2D further illustrate each of the shim block assemblies 102A-102D. It is recognized that the other shim block assemblies 102B, 102C and 102D include the same components described below for the shim block assembly 102A in reference to FIG. 2A. An opposing side 112A opposite to the bone contacting side 104A can include apertures 113A and 114A for receiving pins for fixation of the shim block assembly 102A to the femur. The pins can be a straight pin or a screw pin, or a similar type of fixation device. As described below, an intramedullary rod can be used to position the shim block assembly 102A on the distal femur. The pins can optionally be used with the shim block assembly 102A for further fixation. In an example, a straight pin can be used for rotational fixation. In an example, a screw pin can be used for rotation fixation and distal fixation.

The aperture 110A of the shim block assembly 102A can extend from the bone contacting side 104A through to the opposing side 112A. A top or proximal portion 116A can include two apertures 118A and 120A for placement of the shim block assembly 102A on a guide tower or a resection tower.

The shim block assembly 102A can be placed on the distal femur using the guide tower or a similar instrument. A distal femoral cut guide can be connected to the shim block assembly 102A and can be configured to receive a saw or other cutting device for resecting the distal femur. A position of the shim block assembly 102A on the distal femur can control where the resections are made on the distal femur and thus a thickness of the two distal resections (medial and lateral) of the condyles.

Differences in a thickness of the shim block assemblies 102A-102D can result in distal resections of different thicknesses depending on the particular shim block assembly selected, as described further below. Within the set 100, at least one of the shim block assemblies 102A-102D can have a medial shim thickness different from a lateral shim thickness.

Figure 2A:
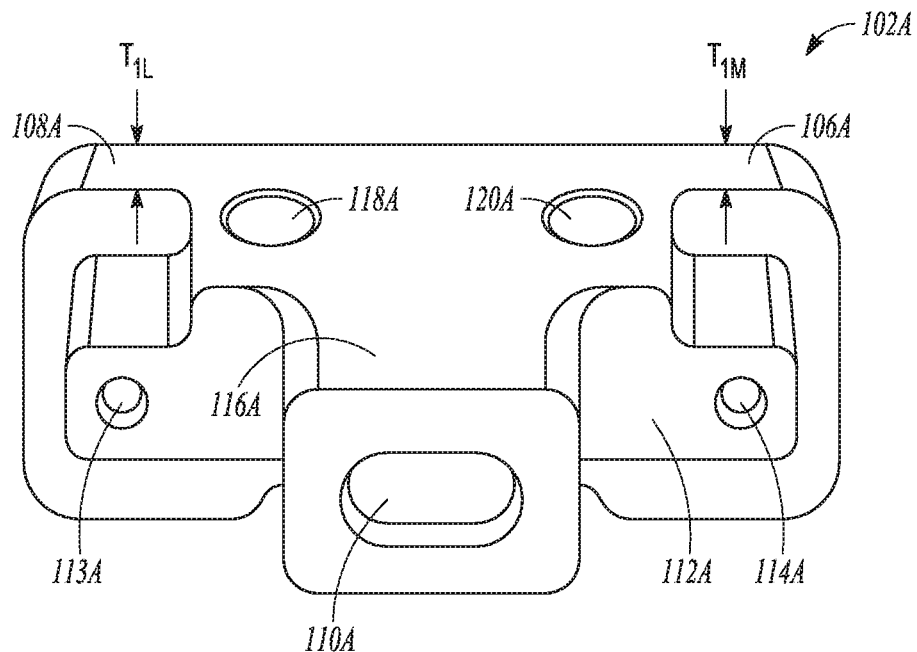
FIGS. 2A-2D are perspective views of each of the shim block assemblies from FIG. 2.
Figure 2B:
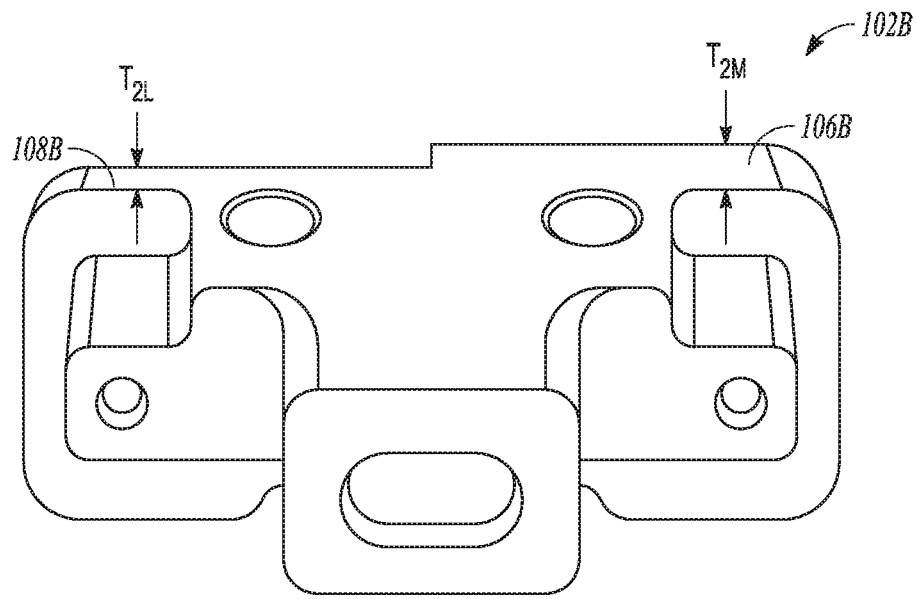
Figure 2C:
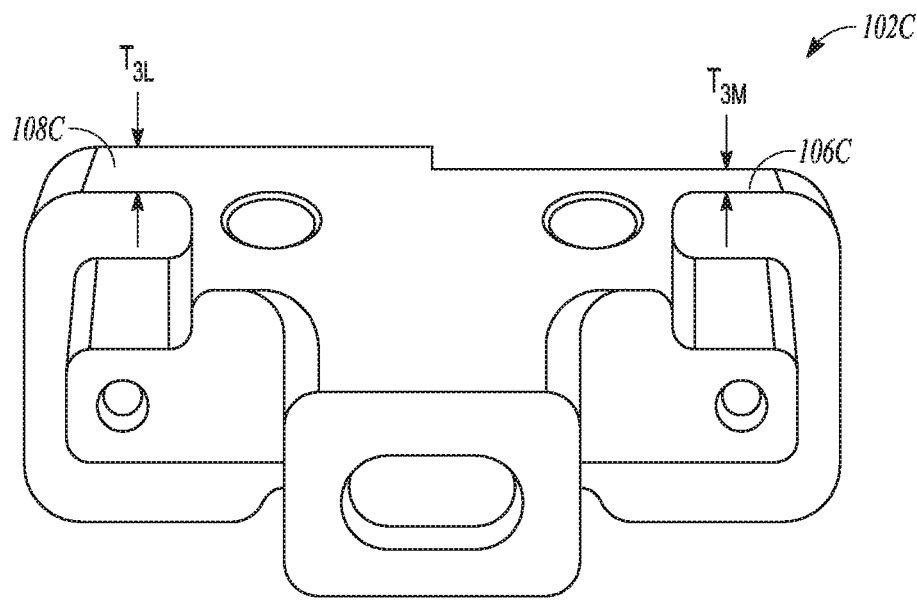
Figure 2D:
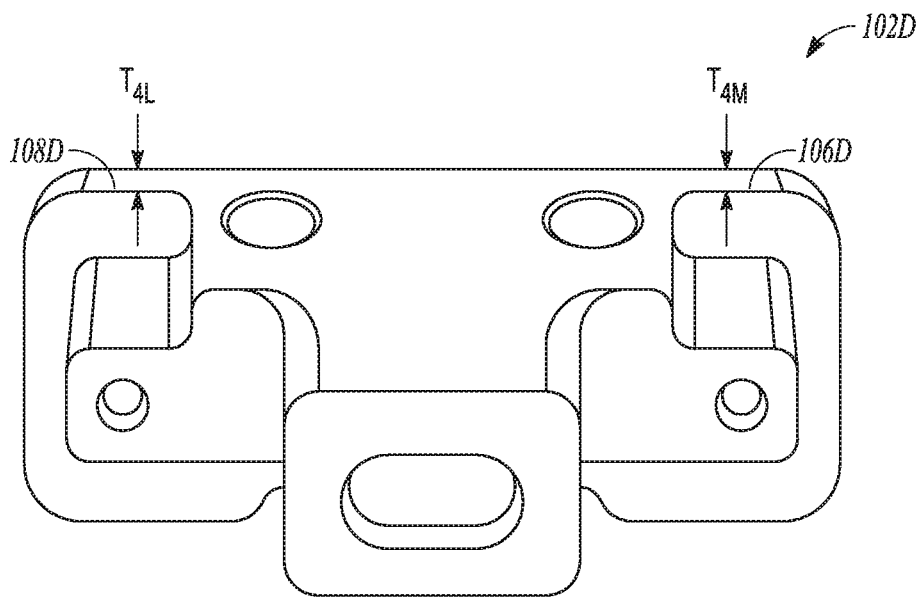

The shim block assembly 102A can include a medial shim thickness $T_{1M}$ and a lateral shim thickness $T_{1L}$. As shown in FIG. 2A, the medial shim thickness $T_{1M}$ can be equal to the lateral shim thickness $T_{1L}$. The shim block assembly 102B can include a medial shim thickness $T_{2M}$ and a lateral shim thickness $T_{2L}$. As shown in FIG. 2B, the medial shim thickness $T_{2M}$ can be greater than the lateral shim thickness $T_{2L}$. The shim block assembly 102C can include a medial shim thickness $T_{3M}$ and a lateral shim thickness $T_{3L}$. As shown in FIG. 2C, the lateral shim thickness $T_{3L}$ can be greater than the medial shim thickness $T_{3M}$. The shim block assembly 102D can include a medial shim thickness $T_{4M}$ and a lateral shim thickness $T_{4L}$. As shown in FIG. 2D, the medial shim thickness $T_{4M}$ can be equal to the lateral shim thickness $T_{4L}$.

Table 1 below shows the intended scenario for each of the shim block assemblies 102A-102D.

TABLE 1

| Shim Block Assembly | Medial Condyle | Lateral Condyle |
| --- | --- | --- |
| 102A | Worn | Worn |
| 102B | Worn | Unworn |
| 102C | Unworn | Worn |
| 102D | Unworn | Unworn |

As stated above, if the medial or lateral distal condyle is worn, the cartilage wear can commonly be about 2 mm. As such, in an example, a difference in a thickness of the shim block assembly 102 between a worn and an unworn portion of the shim block assembly can be about 2 mm. The shim block assembly 102D can be configured for use on a femur having little to no wear on either the medial or lateral condyle. The shim block assembly 102C can be configured for use on a femur having wear on a lateral condyle and little to no wear on a medial condyle. The lateral shim thickness $T_{3L}$ of the shim block assembly 102C can be about 2 mm greater than the lateral shim thickness $T_{4L}$ of the shim block assembly 102D and about 2 mm greater than the medial shim thickness $T_{3M}$ of the shim block assembly 102C. The shim block assembly 102B can be configured for use on a femur having wear on a medial condyle and little to no wear on a lateral condyle. The lateral shim thickness $T_{2L}$ of the shim block assembly 102B can be about equal to the lateral shim thickness $T_{4L}$ of the shim block assembly 102D and about 2 mm less than the medial shim thickness $T_{2M}$ of the shim block assembly 102B. The shim block assembly 102A can be configured for use on a femur having wear on both the medial and lateral condyles. The lateral shim thickness $T_{1L}$ of the shim block assembly 102A can be about 2 mm greater than the lateral shim thickness $T_{4L}$ of the shim block assembly 102D. The medial shim thickness TIM of the shim block assembly 102A can be about 2 mm greater than the medial shim thickness $T_{4M}$ of the shim block assembly 102D and about equal to the lateral shim thickness $T_{1L}$ of the shim block assembly 102A.

It is recognized that additional or alternative shim block assemblies can be included in the set 100 having thickness differentials of less than or more than 2 mm.

In an example, the distal resection of the medial and lateral condyles can be intended to be about 8 mm for a condyle having little to no wear. Thus, for a worn condyle having a typical wear of about 2 mm, the distal resection can be intended to be about 6 mm. In an example, as shown on the cut block assemblies 102A-102D of FIG. 2, the distal cut can be configured for 9 mm, which results in a bone resection of 8 mm (i.e. 9 mm less the thickness of the saw blade, which is approximately 1 mm). The distal cut of 9 mm can be based on a distal thickness of the prosthesis being about 9 mm. It is recognized that other target thicknesses of the bone resections can be selected based on a different thickness of the prosthesis or saw blade, and the distal femoral cartilage loss.

The set 100 can be used for either a right knee or a left knee. As shown above with the particular configuration of the medial 106 and lateral 108 portions of each block assembly 102, the shim block assemblies 102A-102D are configured for use on a right leg of a patient. However, the shim block assemblies 102A-102D can be used on a left leg of a patient, in which case the medial portion 106 of the bone contacting side 104 would be placed on the lateral side of a patient's left leg and the lateral portion 108 would be placed on the medial side of the patient's left leg.

In the set 100 of shim block assemblies 102A-102D, the shim area of the block, having medial and lateral portions, is integral with the rest of the block assembly to form a monolithic or one-piece shim block assembly. In another example, separate shim components can be modular, such that each shim component can be removably attachable and interchangeable with a common block assembly.

Figure 3A:
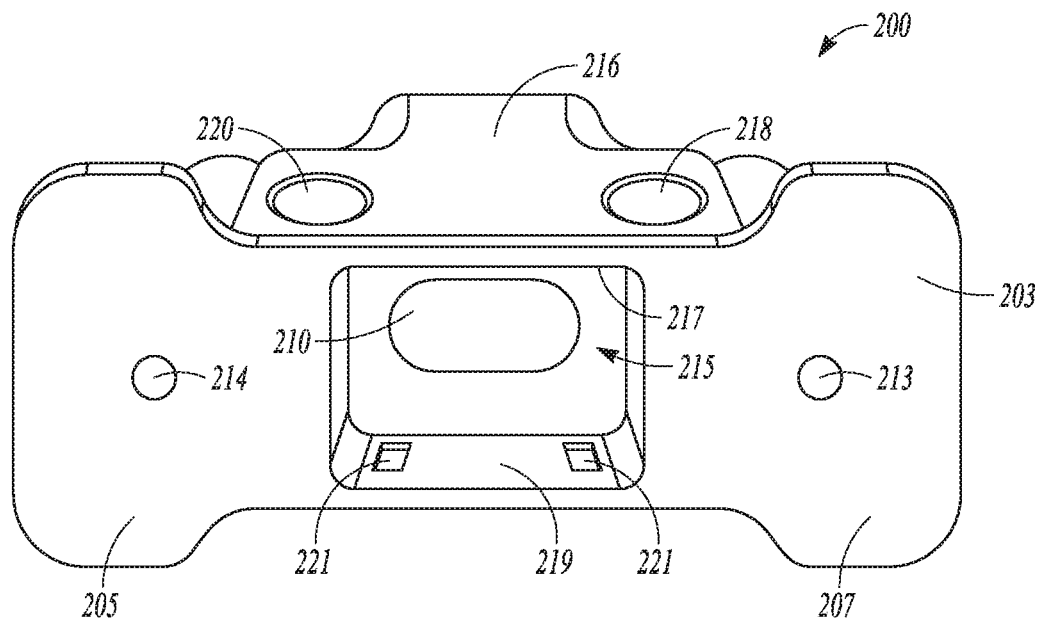
FIG. 3A is a perspective back view of an example of a block assembly in accordance with the present application.
Figure 3B:
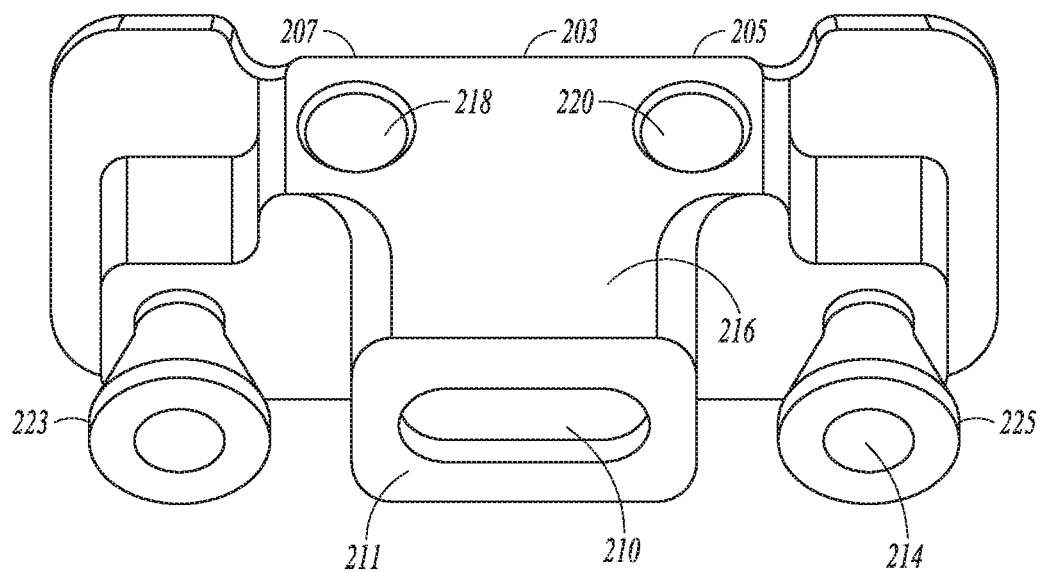
FIG. 3B is a perspective front view of the block assembly of FIG. 3A.

FIGS. 3A and 3B illustrate such an example of a block assembly 200 configured for use with multiple shim components. The block assembly 200 can have a similar shape and design to the shim block assemblies 102A-102D. A surface 203 on a bone contacting side of the block assembly 200 can include a medial portion 205 and a lateral portion 207. The surface 203 can be a level, planar surface configured to receive the shim components of FIGS. 4-4D. An aperture 210 can extend through the surface 203 to an opposite side 211 of the block assembly 200 (see FIG. 3B) and can be configured for receiving an intramedullary rod. Apertures 213 and 214 can extend through the surface 203 to the opposing side of the block assembly 200 and can function similar to the apertures 13A and 114A of the shim block assembly 102A of FIG. 2A. Apertures 213 and 214 can be configured to receive a fixation pin or other type of fixation device, as described above in reference to the shim block assembly 102A.

As shown in FIG. 3A, the block assembly 200 can have a notch 215 which is sized and shaped to receive a mating feature on each of the shim components. A top 217 and bottom 219 portion of the notch 215 can each include one or more recesses 221 that receive a protrusion or similar type feature on each of the shim components. (The recesses 221 in the top portion 217 of the notch 215 are not visible in FIG. 3A.) The block assembly 200 can include apertures 218 and 220 on a top portion 216 of the block assembly 200 for placement of the block assembly 200 on a guide tower or a resection tower.

As shown in FIG. 3B, the block assembly 200 can include extensions or collars 223 and 225. The aperture 213 shown in FIG. 3A can extend from the surface 203 through the extension 223 and the aperture 214 shown in FIG. 3A can extend from the surface 203 through the extension 225. As described above, the apertures 213 and 214 can be configured for receiving a fixation pin. A size and shape of the extensions 223 and 225 can be configured such that a surgeon or other user can easily grip the block assembly 200. Other designs can be used as an alternative to the extensions 223 and 225 as shown in FIG. 3B. It is recognized that the shim block assemblies 102A-102D of FIGS. 2-2D can include similar features to the extensions 223 and 225.

Figure 4:
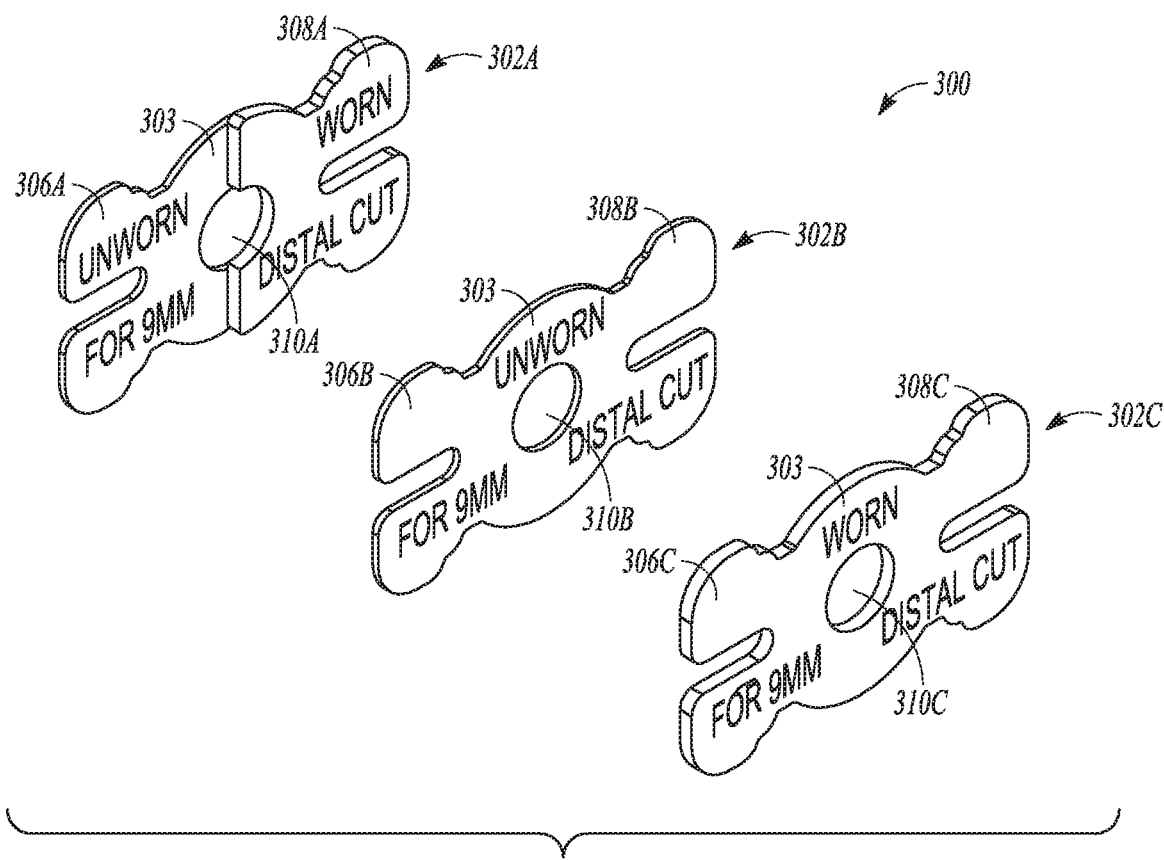
FIG. 4 is a perspective view of an example of a set of shim components in accordance with the present application.

FIG. 4 shows an example of a set 300 of shim components 302A, 302B and 302C. Each shim component 302 can include a bone contacting side 303, an opposing assembly contacting side 305 (see FIG. 4A), a medial portion 306, a lateral portion 308 and an aperture 310 configured to receive an intramedullary rod. Each shim component 302 can be modular and removably attachable or securable to the block assembly 200 of FIGS. 3A and 3B. A combination of the block assembly 200 and one of shim components 302A, 302B and 302C can function similarly to the one-piece shim block assemblies 102A-102D of FIG. 2. The assembly contacting side 305 can contact the surface 203 of the block assembly 200 and when the block assembly 200 is attached to the distal femur, the bone contacting side 303 can contact or abut the distal femur.

Figure 4A:
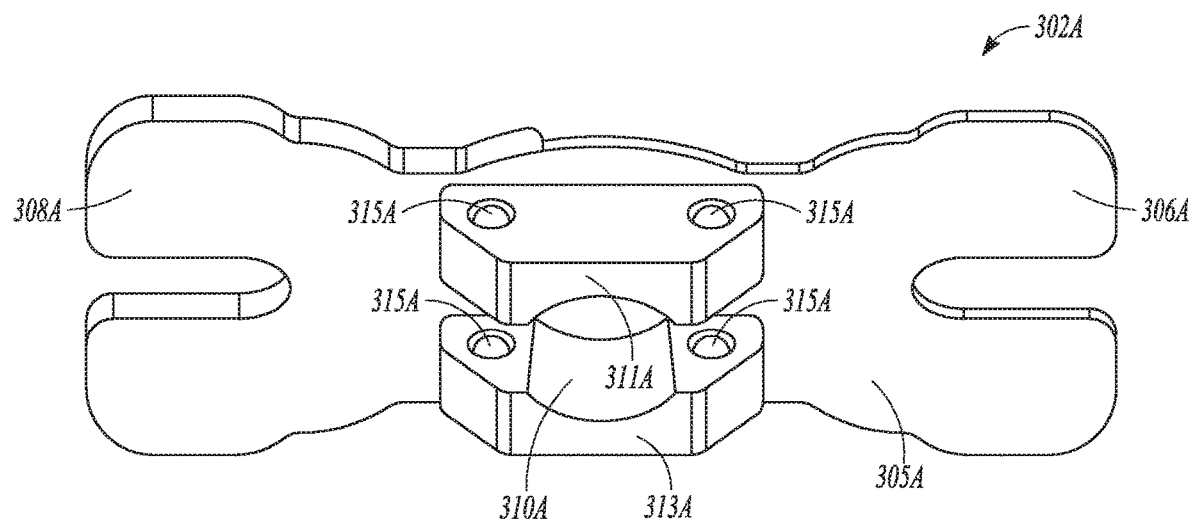
FIG. 4A is a perspective front view of one of the shim components from FIG. 4.

FIG. 4A is a front perspective view of the shim component 302A including the assembly contacting side 305A. It is recognized that the other shim components 302B and 302C include the same components described for the shim component 302A. The assembly contacting side 305A can be configured to directly contact the surface 203 of the block assembly 200 (see FIG. 3A). Top 311A and bottom 313A features extending from the assembly contacting side 305A can be sized and shaped to mate with the notch 215 formed in the block assembly 200. The protrusions 315A on the top 311A and bottom 313A features can be received in the recesses 221 in the notch 215 of the block assembly 200. The interaction between the top 311A and bottom 313A features and the notch 215 can be configured to removably secure the shim component 302A to the block assembly 200. It is recognized that other types of corresponding or mating features can be used on the block assembly 200 and the shim component 302A to facilitate a modular design and removably secure the shim component 302A to the block assembly 200.

Figure 4B:
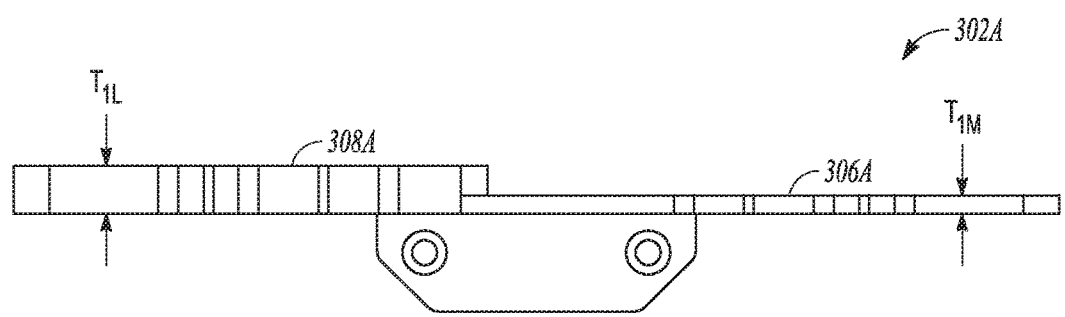
FIG. 4B is a top view of the shim component of FIG. 4A.
Figure 4C:
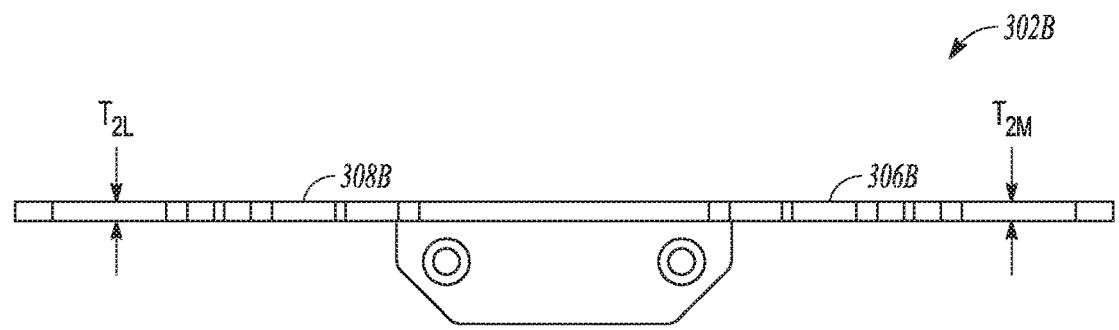
FIGS. 4C and 4D are perspective views of the other shim components from FIG. 4.
Figure 4D:
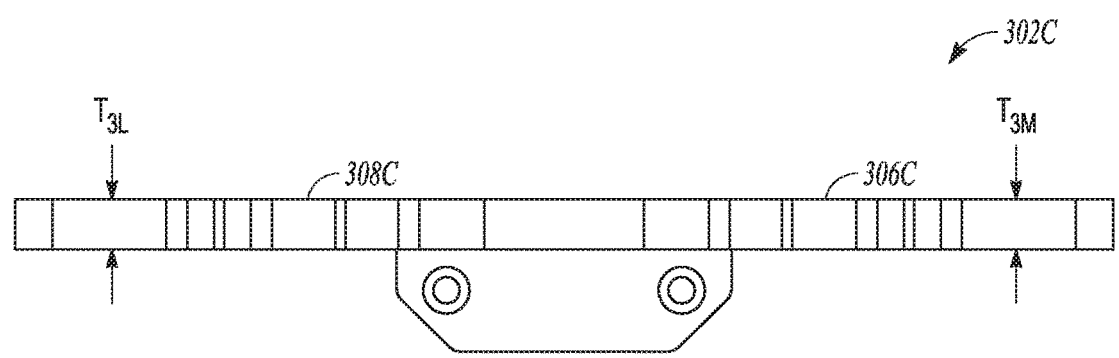

FIGS. 4B-4D illustrate a thickness profile of each of the shim components 302A, 302B and 302C. For shim component 302A, the lateral portion 308A can have a lateral thickness $T_{1L}$ greater than a medial thickness $T_{1M}$ of the medial portion 306A. As such, the shim component 302A can be configured for use on a right leg having an unworn medial condyle and a worn lateral condyle. For shim component 302B, the lateral portion 308B can have a lateral thickness $T_{2L}$ generally equal to a medial thickness $T_{2M}$ of the medial portion 306B. The thicknesses $T_{2L}$ and $T_{2M}$ of the lateral 308B and medial 306B portions, respectively, of the shim component 302B can be generally equal to the medial thickness $T_{1M}$ of the medial portion 306A of the shim component 302A, and the shim component 302B can be configured for use on a right leg having unworn medial and lateral condyles. For shim component 302C, the lateral portion 308C can have a lateral thickness $T_{3L}$ and the medial portion 306C can have a medial thickness $T_{3M}$, and the lateral $T_{3L}$ and medial $T_{3M}$ thicknesses can be generally equal to each other. The medial $T_{3M}$ and lateral $T_{3L}$ thicknesses of the shim component 302C can be greater than the medial $T_{2M}$ and lateral $T_{2L}$ thicknesses of the medial 306B and lateral 308B portions of the shim component 302B by a predetermined amount. In an example, the predetermined amount can be about 2 mm, which corresponds to the typical amount of cartilage loss on a worn condyle. The shim component 302C can be configured for use on a right leg having worn medial and lateral condyles. Table 2 below shows each of these scenarios for shim components 302A, 302B and 302C.

TABLE 2

| Shim Component | Medial Condyle | Lateral Condyle |
|---|---|---|
| 302A | Unworn | Worn |
| 302B | Unworn | Unworn |
| 302C | Worn | Worn |
| 302A (rotated 180°) | Worn | Unworn |

A fourth scenario can exist for the right leg in which the medial condyle is worn and the lateral condyle is unworn. The shim component 302A can configured for use on that leg if the shim component 302A is rotated 180 degrees such that the thicker lateral portion 306A can be oriented for placement on the worn medial condyle. Consequently, the thinner medial portion 308A is oriented for placement on the unworn lateral condyle.

As described above in regard to the set 100 of the shim block assemblies 102A-102D, the set 300 of the shim components 302A-302C are described for use on a right leg of a patient. The shim components 302A-302C can be used on a left leg of a patient, in which case the medial portion 306 can be placed on the lateral side of a patient's left leg and the lateral portion 308 can be placed on the medial side of the patient's left leg.

Additional or alternative shim components can be included in the set 300 having thickness differentials less than or more than 2 mm and configured for use with the block assembly 200 of FIGS. 3A and 3B.

Figure 5:
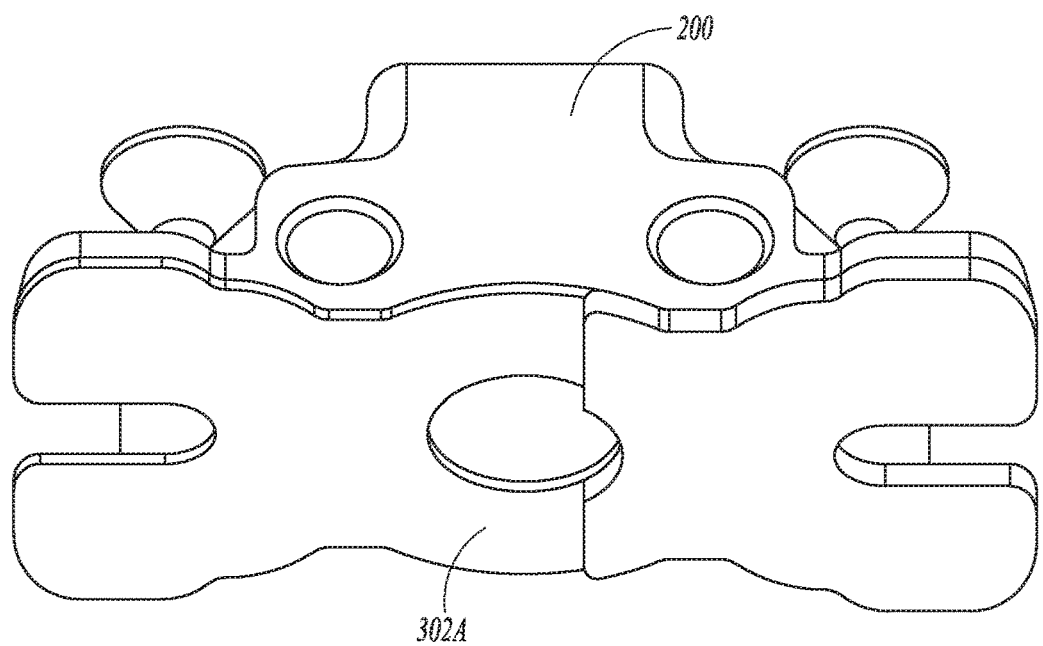
FIG. 5 is a perspective back view of the shim block assembly of FIGS. 3A and 3B with a shim component from FIG. 4 attached thereto.

FIG. 5 shows the block assembly 200 of FIGS. 3A and 3B with the shim component 302A attached to the block assembly 200. As described above, the shim component 302A can be configured for use on a right leg having an unworn medial condyle and a worn lateral condyle. Alternatively, the shim component 302C can be configured for use on a left leg having an unworn lateral condyle and a worn medial condyle.

FIGS. 2-5 illustrate examples of a shim block assembly for use in resecting the distal medial and lateral condyles in a manner that accounts for cartilage wear on the distal condyles. The shim block assembly can be unitary or monolithic (see FIGS. 2-2D) or alternatively, it can be modular (see FIGS. 3A-5). Whether a one-piece assembly or a two-piece assembly is used, the shim block assemblies described herein can provide a simple, accurate and repeatable way of accounting for wear on the distal condyles when resecting the distal condyles in preparation for receiving a femoral prosthesis. It is recognized that additional designs and modifications can be made to the shim block assemblies and associated features described herein for use in a kinematically aligned TKA.

After performing the two distal resections, the thickness of the resected bone from each condyle can be measured to confirm that the targeted amount of bone was in fact resected. In an example, the targeted amount of bone can be about 8 mm for an unworn condyle and about 6 mm for a worn condyle. As described above, a target of 8 mm can be based on a distal thickness of the prosthesis being about 9 mm, and 1 mm subtracted from 9 mm to approximate for the thickness of the saw blade or other cutting tool used to resect the distal femur. A target of 6 mm can be based on further accounting for an approximate amount of distal femoral articulating cartilage loss. It is recognized that these target values may be variable, depending on, for example, a different prosthesis thickness, saw blade thickness or cartilage loss.

If the measured value is less than the targeted amount for one or both of the resections, additional bone can be resected from the distal femur. If the measured value is more than the targeted amount for one or both of the resections, a spacer can be used as described below to compensate for the additionally resected bone.

Figure 6:
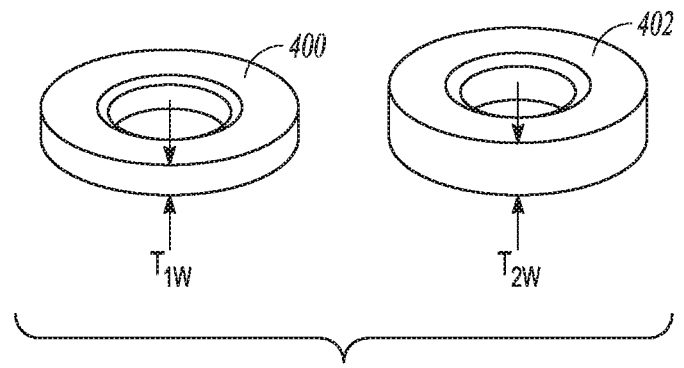
FIG. 6 is a perspective view of an example of two spacers in accordance with the present application.

FIG. 6 shows an example of a first spacer 400 and a second spacer 402 for use in the surgical technique for a kinematically aligned TKA. The first spacer 400 can have a first thickness $T_{1W}$ and the second spacer 402 can have a second thickness $T_{2W}$ greater than the first thickness $T_{1W}$. In an example, the first thickness $T_{1W}$ can be about 1 mm and the second thickness $T_{2W}$ can be about 2 mm. The first 400 and second 402 spacers can be configured for use in resecting the posterior femur, after resecting the distal condyles, if it is determined that one or both of the distal resections are thicker than intended.

As described below in reference to the surgical technique, the first 400 and second 402 spacers are configured for placement on a bone contacting side of a cut block used for performing the posterior femoral resections. In an example, if it determined that 6 mm of bone should be removed from the distal medial condyle, and the actual resection measures at 7 mm, the first spacer 400 having the thickness $T_{1W}$ equal to about 1 mm can be used with the cut block. Additional spacers having thicknesses greater than or less than the thicknesses $T_{1W}$ and $T_{2W}$ of the first 400 and second 402 spacers can also be used.

Figure 7:
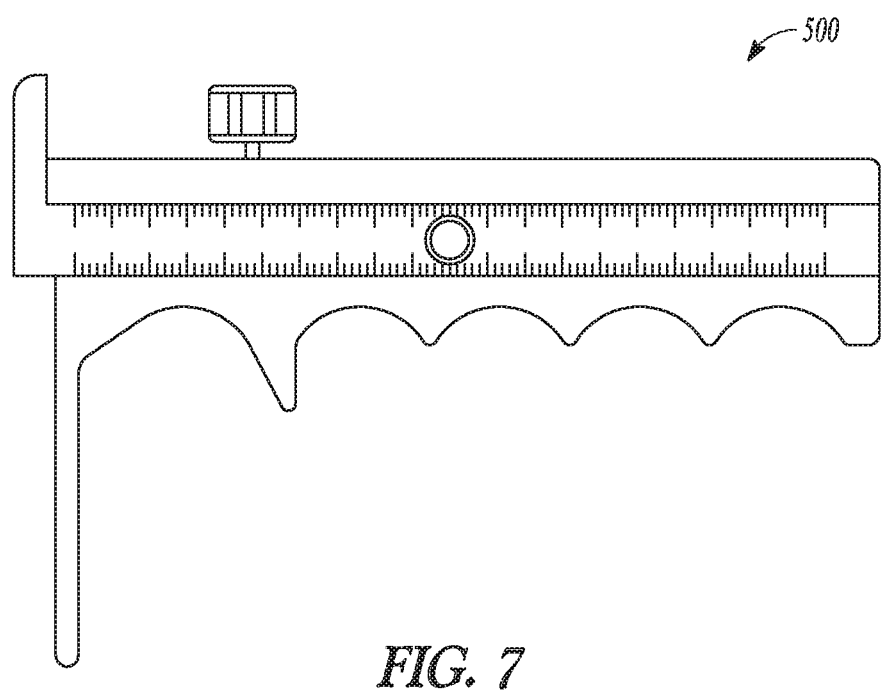
FIG. 7 is a front view of an example of a caliper in accordance with the present application.

FIG. 7 shows an example of a caliper 500 which can be used for performing various measurements throughout the surgical procedure for a kinematically aligned TKA. The caliper 500 can be used, for example, to measure each of the two resections of the distal condyles as described above.

Figure 8:
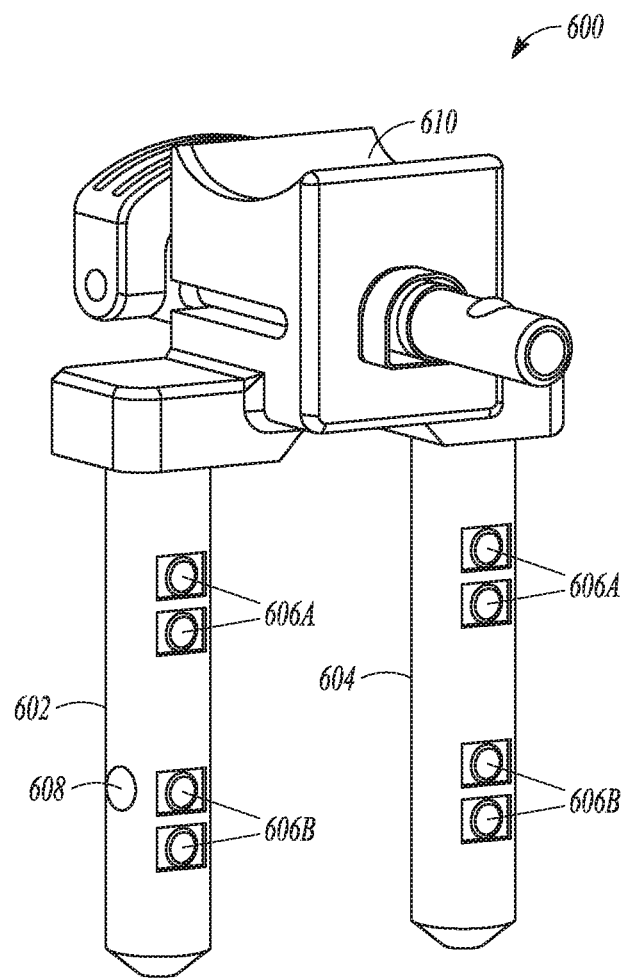
FIG. 8 is a perspective view of an example of a resection tower in accordance with the present application.

FIG. 8 shows an example of a resection tower 600 which can be used with either of the shim block assemblies described above and shown in FIGS. 2-3B and FIG. 5 for attaching the shim block assembly to the distal femur. The resection tower 600 can also be used to connect a distal femoral cut guide or cutting head to the shim block assembly in order to position the cut guide on the distal femur. The shim block assembly can determine a location of the cut guide on the distal femur, or in other words, act as a reference for the cut guide on the distal femur, and thus set or determine an amount of bone resected from the distal femur using the cut guide. FIG. 8 is a perspective view of a back side of the resection tower 600. As shown in FIG. 8, the resection tower 600 can include two legs 602 and 604 which can be configured to receive the shim block assembly (see FIG. 9).

Each of the legs 602 and 604 can include features 606, such as detents, for engaging with the block assembly 200 to removably secure the block assembly 200 on the resection tower 600. In an example, the features 606 can be spring plungers or ball detents and can be configured to maintain the shim block assembly parallel to the cutting surface that the resection tower 600 is attached to. The features 606 can create an interference fit between the resection tower 600 and the shim block assembly, and can provide stability to the shim block assembly on the resection tower 600. Two sets of features 606A and 606B (each set including two features 606 on each leg 602 and 604) can be used to secure the shim block assembly to the resection tower in two different positions on the resection tower 600.

The leg 602 can include a divet or recess 608 formed in the leg 602, which can also engage with a mating feature on the shim block assembly. In another example, the leg 604 can include a similar divet or recess in addition to or as an alternative to the divet 608 on leg 602. The resection tower 600 can include a top portion 610, which can have a concave shape for the user to place one or more fingers for gripping or moving the resection tower 600.

Other types of features in addition to or as an alternative to the detents 606 shown in FIG. 8 can be used on the resection tower 600 for engagement with the shim block assembly.

Figure 9:
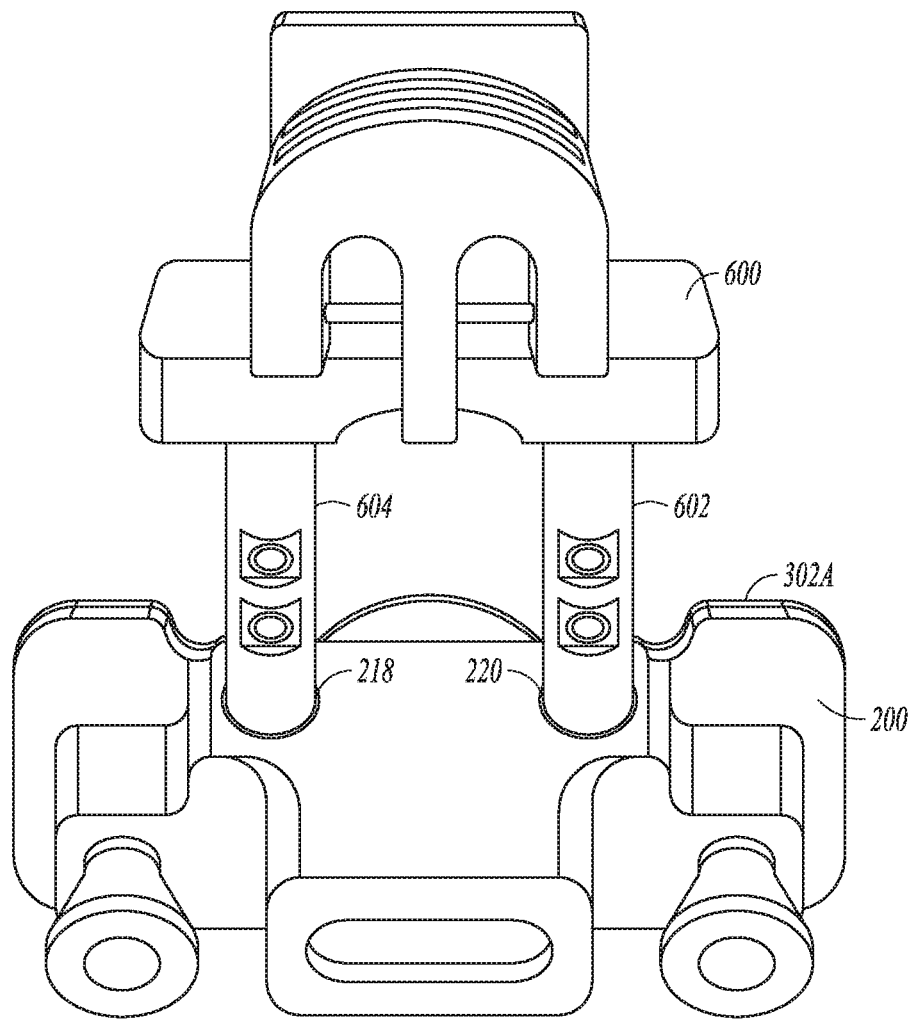
FIG. 9 is a perspective view of the resection tower of FIG. 8 with the shim block assembly and shim component of FIG. 5 attached thereto.

FIG. 9 shows a front view of the resection tower 600 with the block assembly 200 and shim component 302A of FIG. 5 in the process of being assembled on the resection tower 600. The legs 604 and 602 of the resection tower 600 can be inserted through the apertures 218 and 220 on the block assembly 200. As shown in FIG. 9, the block assembly 200 and shim component 302A can be removably secured to the resection tower 600 at a position on the legs 602 and 604 that corresponds with the second set of features 606B. As described below in reference to the surgical technique, the configuration shown in FIG. 9 can be used for initially placing the block assembly 200 and shim component 302A on the distal femur. In a subsequent step the resection tower 600 can be moved relative to the block assembly 200 and shim component 302A such that the block assembly 200 and shim component 302 can be removably secured to the resection tower 600 at a position on the legs 602 and 604 corresponding to the first set of features 606A. The resection tower 600 can also be configured to removably secure the cut guide that performs the distal resections. A resection tower similar to the resection tower 600 is shown in use with the block assembly 200 and the cut guide in FIG. 16 in reference to the surgical technique for performing a kinematically aligned TKA. It is recognized that any of the shim block assemblies 102A-102D can similarly be used with the resection tower 600.

Figure 10:
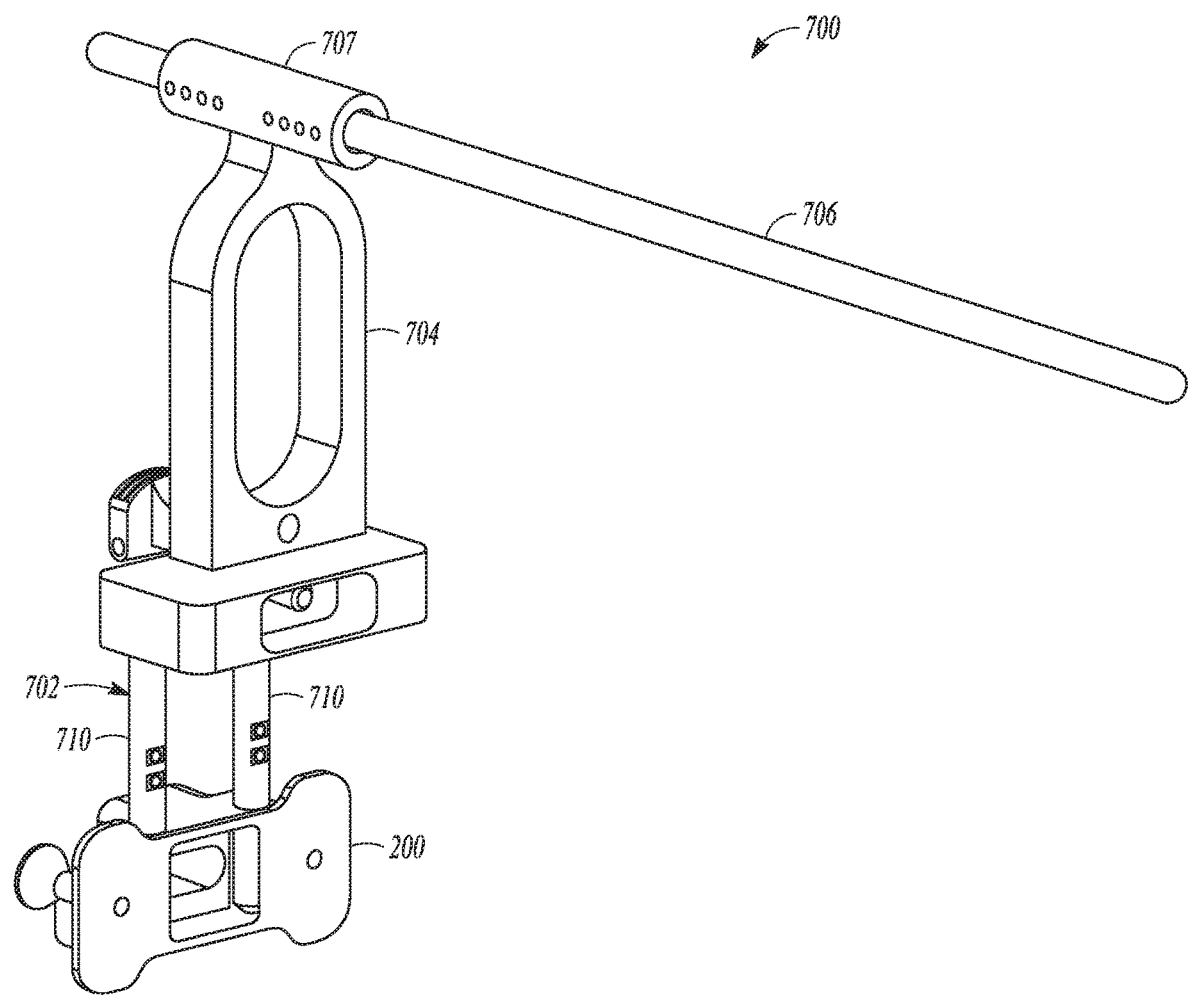
FIG. 10 is a perspective view of an example of a tower assembly in accordance with the present application.

FIG. 10 shows an example of a tower assembly 700 configured for performing an extramedullary technique, as compared to an intramedullary technique. The tower assembly 700 can include the block assembly 200 of FIGS. 3A-3B, a resection tower 702 similar to the resection tower 600 of FIG. 8, and an alignment tower assembly 704 including an alignment rod 706. As described further below with regard to the surgical technique, an extramedullary technique, using the alignment rod 706, can be used to perform the distal femoral resections. The alignment rod 706 can be used to set the flexion/extension of the femoral component. Alternatively, an intramedullary rod can be implanted in the distal femur and used to set the flexion/extension of the femoral component of the knee prosthesis.

In an example, the alignment rod 706 can be formed of a light-weight titanium. The rod 706 can be attached to the tower assembly 700 using a collet 707. In an example, the collet 707 can have spring legs at each end which can provide stability and prevent movement of the rod 706 such that the rod 706 can set flexion/extension.

In an extramedullary technique, the resection tower 702 can include legs 708 and 710 which can be longer as compared to the legs 602 and 604 of the resection tower 600. As shown in FIG. 10, the tower assembly 700 includes the block assembly 200 which can be used with any of the shim components 302A, 302B or 302C in the set 300. The tower assembly 700 can also be used with any of the shim block assemblies 102A-102D of the set 100.

Figure 11:
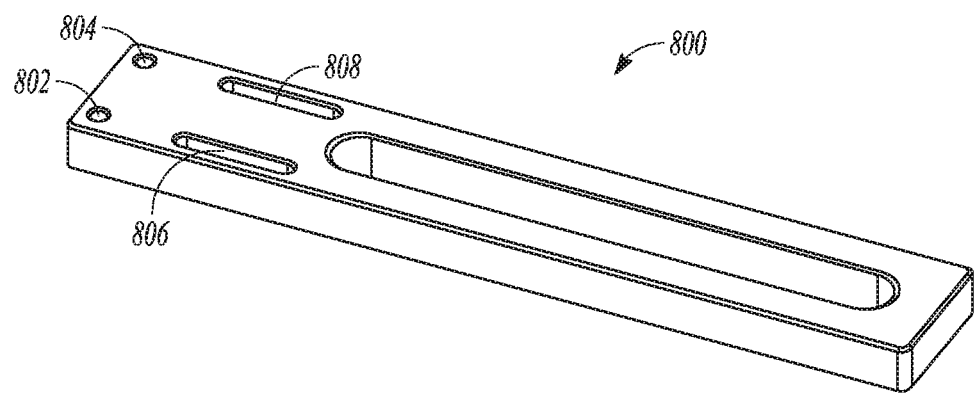
FIG. 11 is a perspective view of an example of an alignment guide in accordance with the present application.

FIG. 11 shows an example of an alignment guide 800 that can be used for setting the internal/external rotation of the tibial component of the knee prosthesis. The alignment guide 800 can include pin apertures 802 and 804 and slots 806 and 808 for alignment and pin placement. As described further below in reference to the surgical technique, the alignment guide 800 can be used to set internal/external (I/E) rotation through a visual inspection of cartilage wear and aligning an anterior/posterior (A/P) axis of the tibia.

A combination of the tools or instruments shown in FIGS. 2-11 can be used in performing the kinematically aligned TKA. An example of the surgical technique for performing the kinematically aligned TKA is described below. It is recognized that additional or alternative steps can be used.

An initial step in the surgical technique can include determining the cartilage wear on the distal medial and lateral condyles pre-operatively. This can be done, for example, using radiograph or MRI. Another pre-operative step can include confirming the patient's hip-knee-ankle (HKA) alignment.

Figure 12:
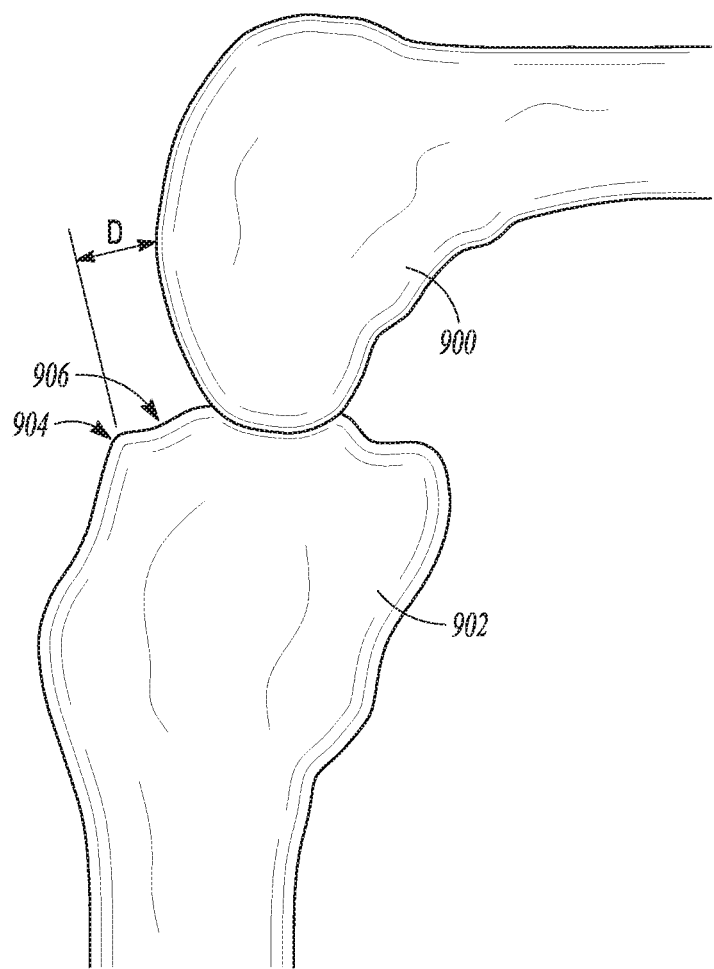
FIG. 12 is a side or sagittal plane view of a knee joint in flexion.

A next step can include exposing the knee joint of the patient by performing an incision. Once the surgeon has access to the knee joint, a natural anterior/posterior (A/P) offset of the patient's knee can be measured. To obtain this measurement, the patient's knee can be flexed to 90 degrees of flexion. FIG. 12 shows a schematic of a femur 900 and tibia 902 in flexion. A distance D can be measured from an anterior location 904 on a proximal surface 906 of the tibia 902 to the distal medial condyle 908 of the femur 900. The obtained measurement can represent the patient's natural A/P offset. A caliper, such as, for example, the caliper 500 of FIG. 7, or a comparable tool, can be used for measuring the distance D. If the cartilage is worn on the medial condyle 908, then two millimeters can be subtracted from the distance D to account for the wear. In an example, if the measured distance D is 15 mm and the medial condyle is worn, the natural offset is determined to be 13 mm. The natural offset can be recorded for later reference in the surgical technique.

Figure 12A:
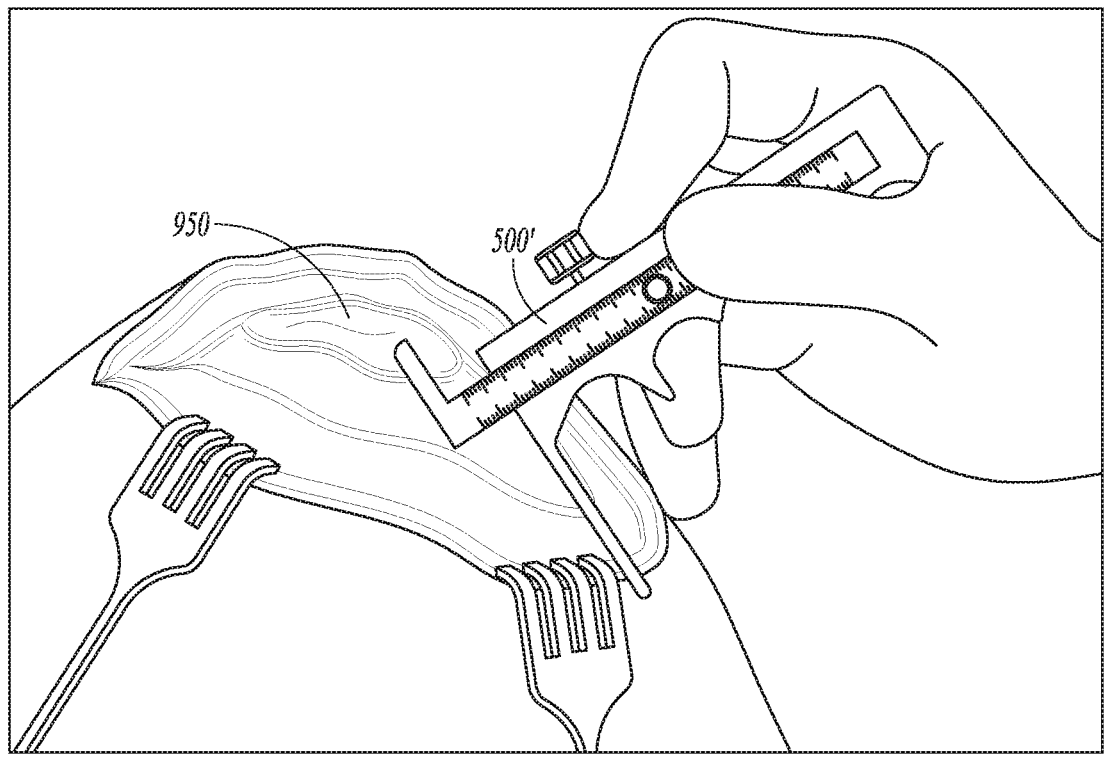
FIG. 12A is an image of a knee joint in flexion to obtain a measurement using a caliper.

FIG. 12A shows a knee joint 950 in flexion to illustrate how the measurement described above in FIG. 12 can be obtained. A caliper 500', similar to caliper 500 of FIG. 7, is shown in use in FIG. 12A for measuring the distance D as defined above and shown in FIG. 12.

FIGS. 13-26 include images of a left leg of a patient, having a varus deformity, in the various stages of a kinematically aligned TKA and are included to supplement the description of the surgical technique below.

Distal Femoral Resections

An objective of the kinematically aligned TKA is that a thickness of the femoral component of the knee prosthesis can be equal to the sum of the thickness of the bone resection, the thickness of the cartilage wear, and the thickness of a blade used to make the bony resections. As stated above, a pre-operative step can include determining a location and extent of cartilage wear. After the patient's knee is exposed, a subsequent step can include confirming the wear on the knee. As stated above, for a valgus knee, wear can commonly be observed for the distal lateral condyle, and for a varus knee, wear can commonly be observed for the distal medial condyle.

The A/P offset measurement described above in reference to FIG. 12 can be performed after the patient's knee is exposed and before the distal resections described below are performed.

Prior to performing any resections, preparation steps can include removing the fat pad, an anterior horn of each meniscus, any osteophytes and the anterior cruciate ligament (ACL). The posterior cruciate ligament (PCL) can be preserved, if possible.

Figure 13:
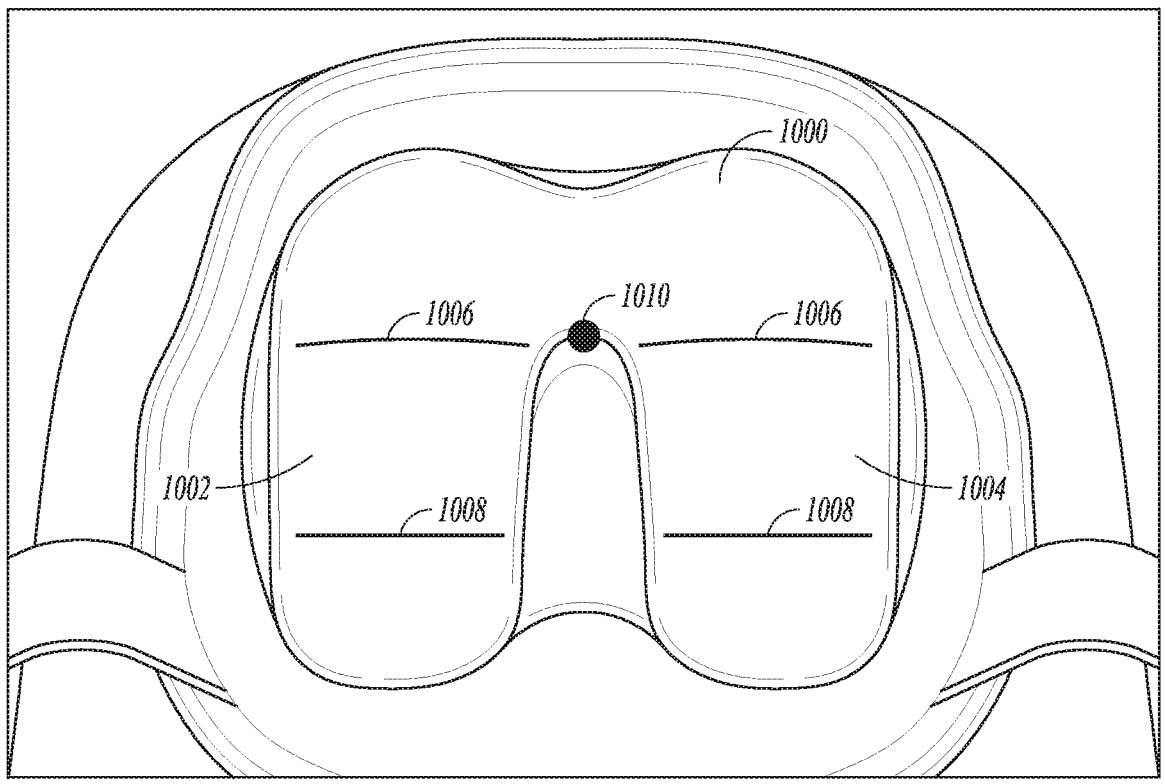
FIG. 13 is an image of a distal femur after a patient's knee joint has been exposed.

FIG. 13 shows a distal femur 1000 of the patient's left leg, including medial 1002 and lateral 1004 condyles of the distal femur 1000. Markings 1006 and 1008 can be made on the distal femur 1000 to correspond to a location for attaching a shim block assembly similar to the shim block assemblies shown in FIGS. 2-5 above. As also shown in FIG. 13, a marking 1010 can be used to indicate a placement for an intramedullary rod into a canal of the femur 1000.

Figure 14:
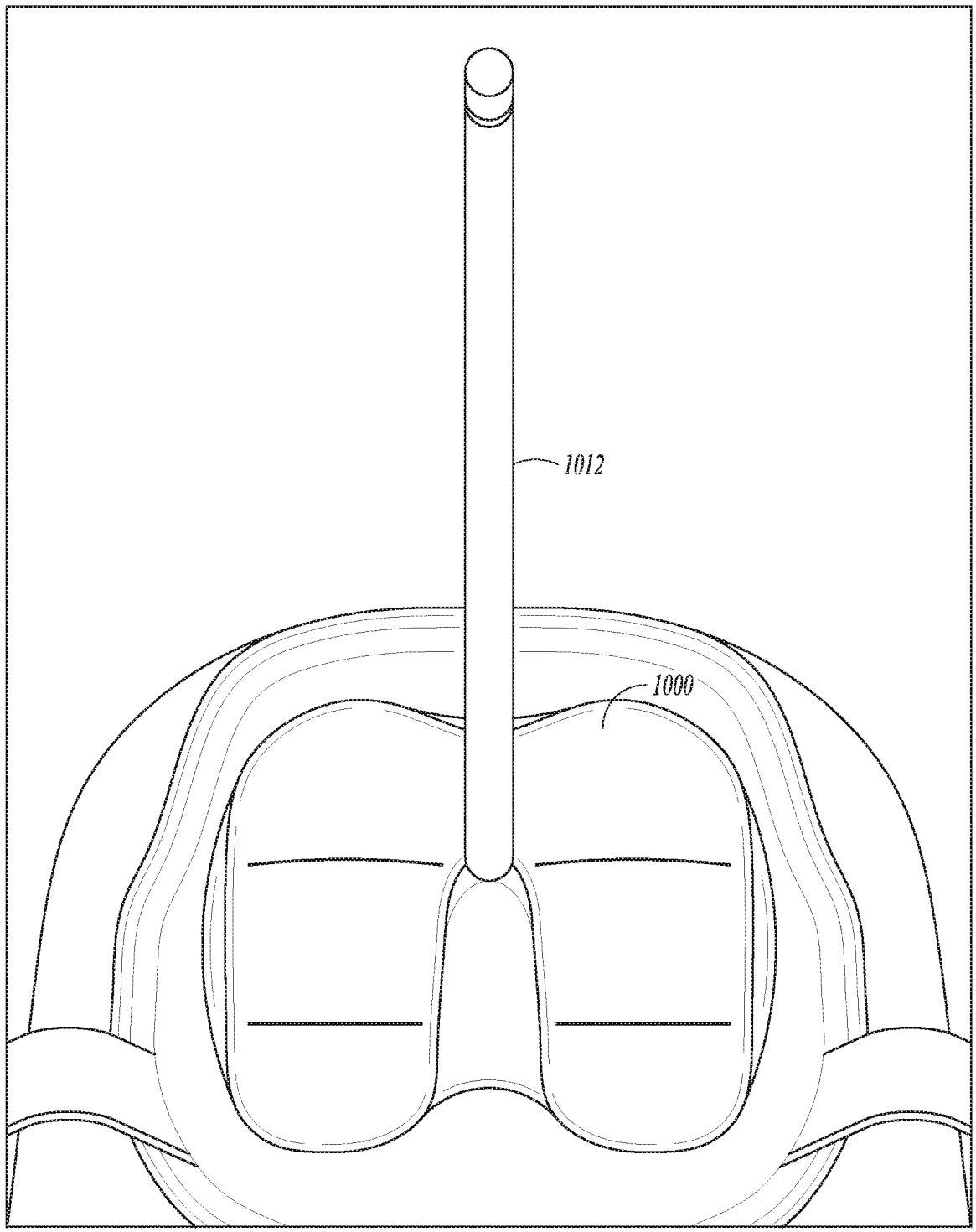
FIG. 14 is an image of the distal femur of FIG. 13 with an intramedullary rod inserted into the distal femur.

FIG. 14 shows the femur 1000 after an opening has been drilled into the femur 1000 and an intramedullary rod 1012 has been implanted. The intramedullary rod 1012 can set the flexion/extension of the femoral component.

Figure 15:
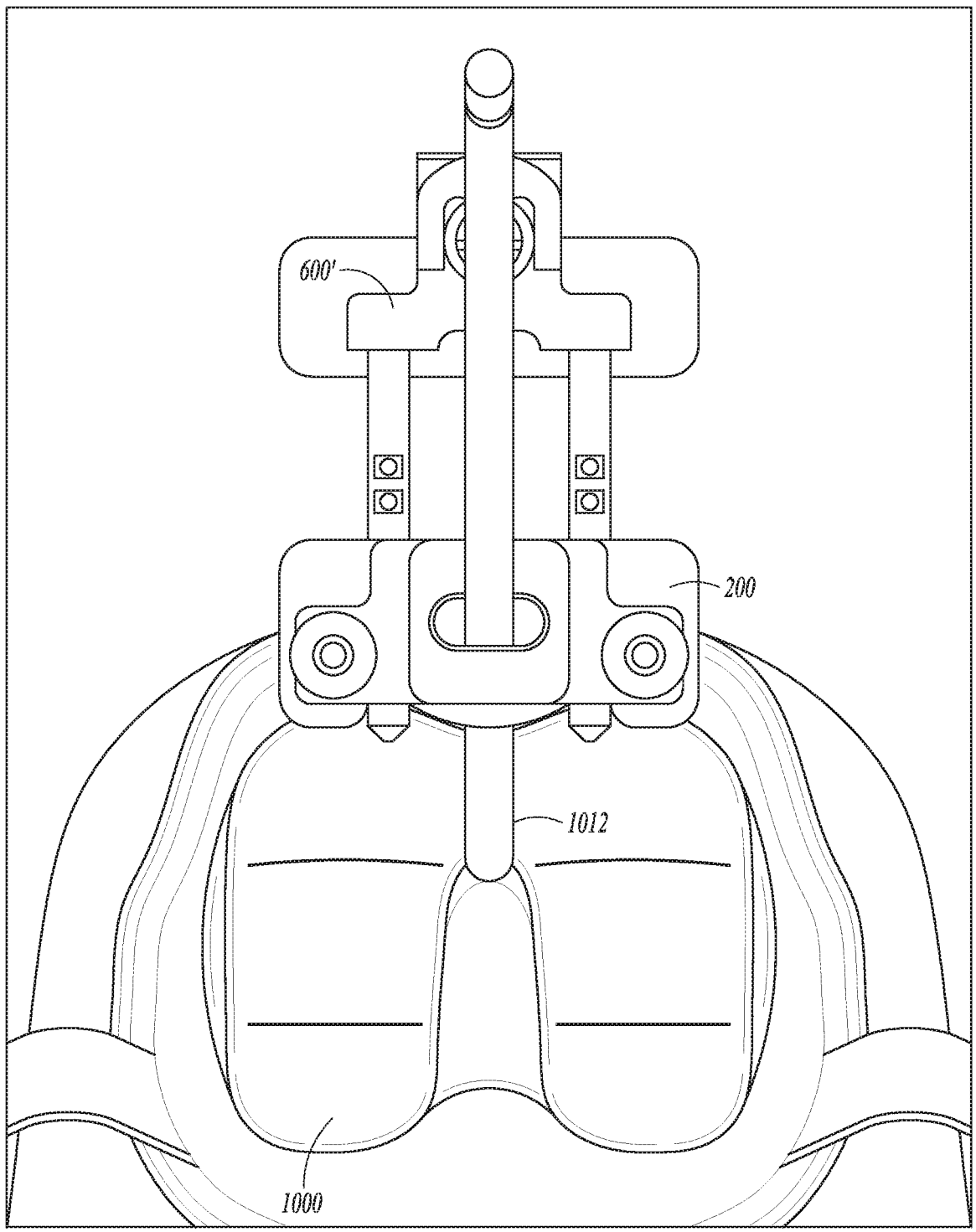
FIG. 15 is an image of the distal femur with a reference tower and shim block assembly being attached to the distal femur.

A shim block assembly 200', which includes the appropriately selected shim based on the worn medial condyle, can next be attached to the distal femur 1000. FIG. 15 shows the shim block assembly 200' as it is being mounted on the distal femur 1000 with the implanted intramedullary rod 1012 being received through the shim block assembly 200'. The shim block assembly 200' can be attached to a guide or resection tower 600', as shown in FIG. 15. The guide or resection tower 600' can be similar to the resection tower 600 of FIG. 8. As shown in FIG. 15, the shim block assembly 200' can be removably secured to the resection tower 600' in the position shown in FIG. 9 in which the shim block assembly 200' can be engaged with the lower set of features 606B on the legs 602 and 604.

Figure 16:
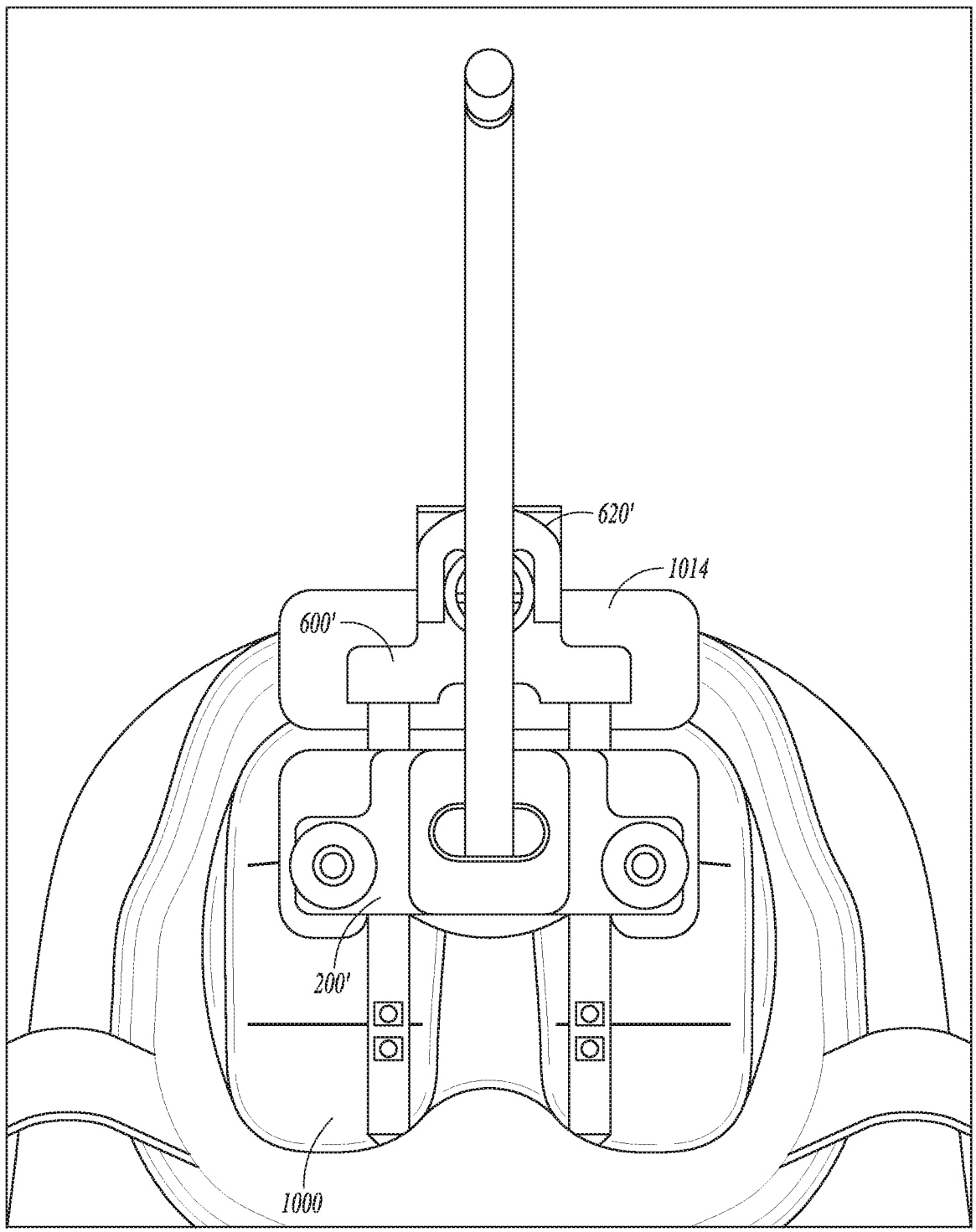
FIG. 16 is an image of the distal femur with the reference tower and the shim block assembly attached thereto, in addition to a distal femoral cut guide.

FIG. 16 shows the resection tower 600' and the shim block assembly 200' in an attached position on the distal femur 1000. Once the shim block assembly 200' is secured to the distal femur 1000, the resection tower 600' can be moved relative to the shim block assembly 200' such that the shim block assembly 200' disengages with the lower or second set of features (see features 606B in FIG. 8) on the legs and engages with the first or upper set of features (see features 606A in FIG. 8) on the legs of the resection tower 600'.

A distal femoral cut guide 1014 can also be attached to the resection tower 600'. The cut guide 1014 can be removably attached at a top portion of the resection tower 600' using a flip lever 620', or similar type of feature, which can engage and release the cut guide 1014. The resection tower 600' can include additional features to aid in removably securing the cut guide 1014 on the resection tower 600'.

As described above, the shim block assembly 200' can set a location for where the distal resections are made on the distal femur 1000 by the distal femoral cut guide 1014, and consequently, can control the thickness of the bone resections.

The shim component used for this particular patient, having a worn medial condyle, can be selected from the shim components 102A, 102B and 102C of FIGS. 4-4D and can have a thicker medial portion, as compared to a shim component used for an unworn medial condyle. The thicker medial portion of the shim component can function to artificially lift the femoral condyle of the femoral prosthesis off the worn side of the femur 1000, in an amount equal to about 2 mm, when the medial resection is made, and restore the distal joint line to the original pre-arthritic condition.

Figure 17:
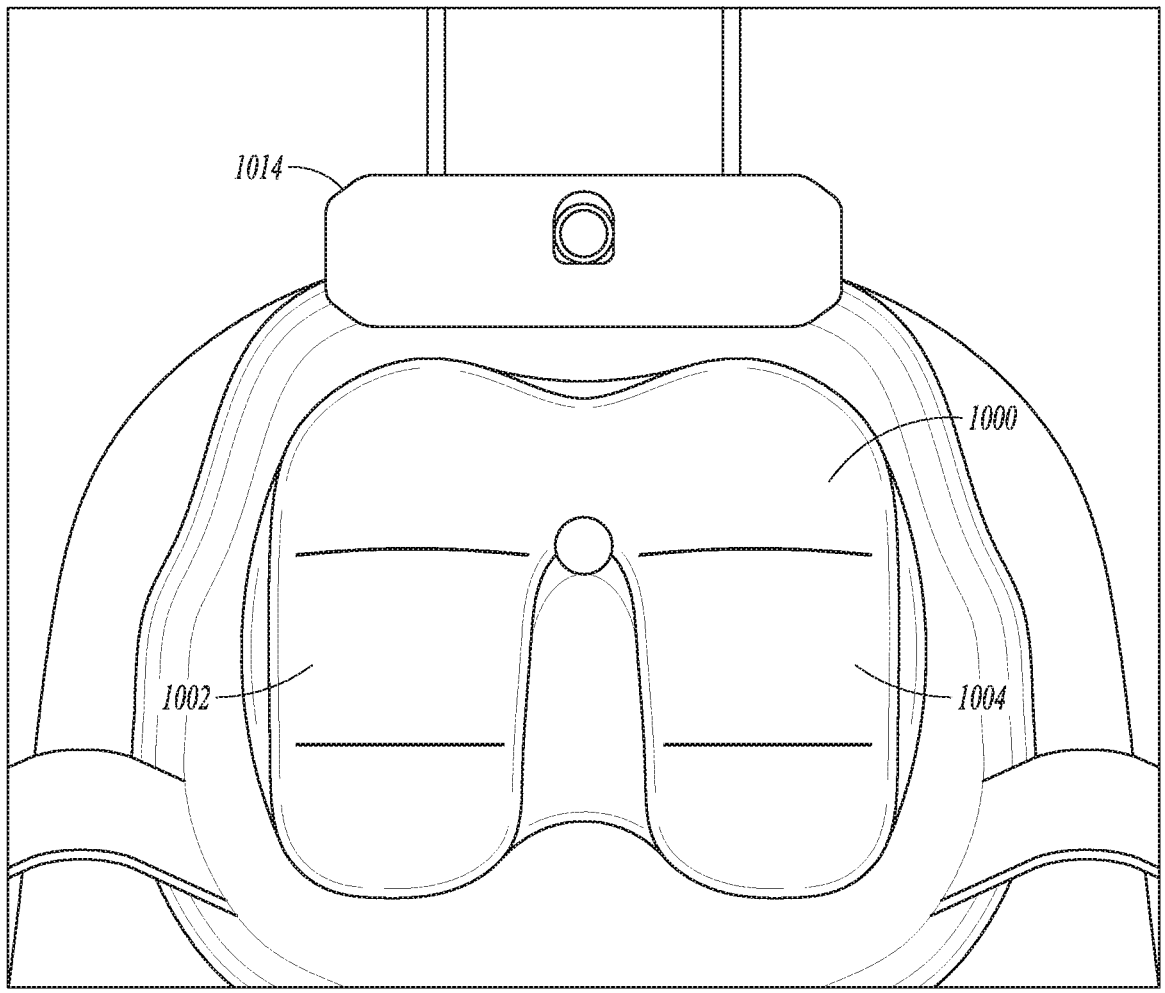
FIG. 17 is an image of the distal femur after the reference tower, the intramedullary rod and the shim block assembly are removed and the cut guide remains.
Figure 18:
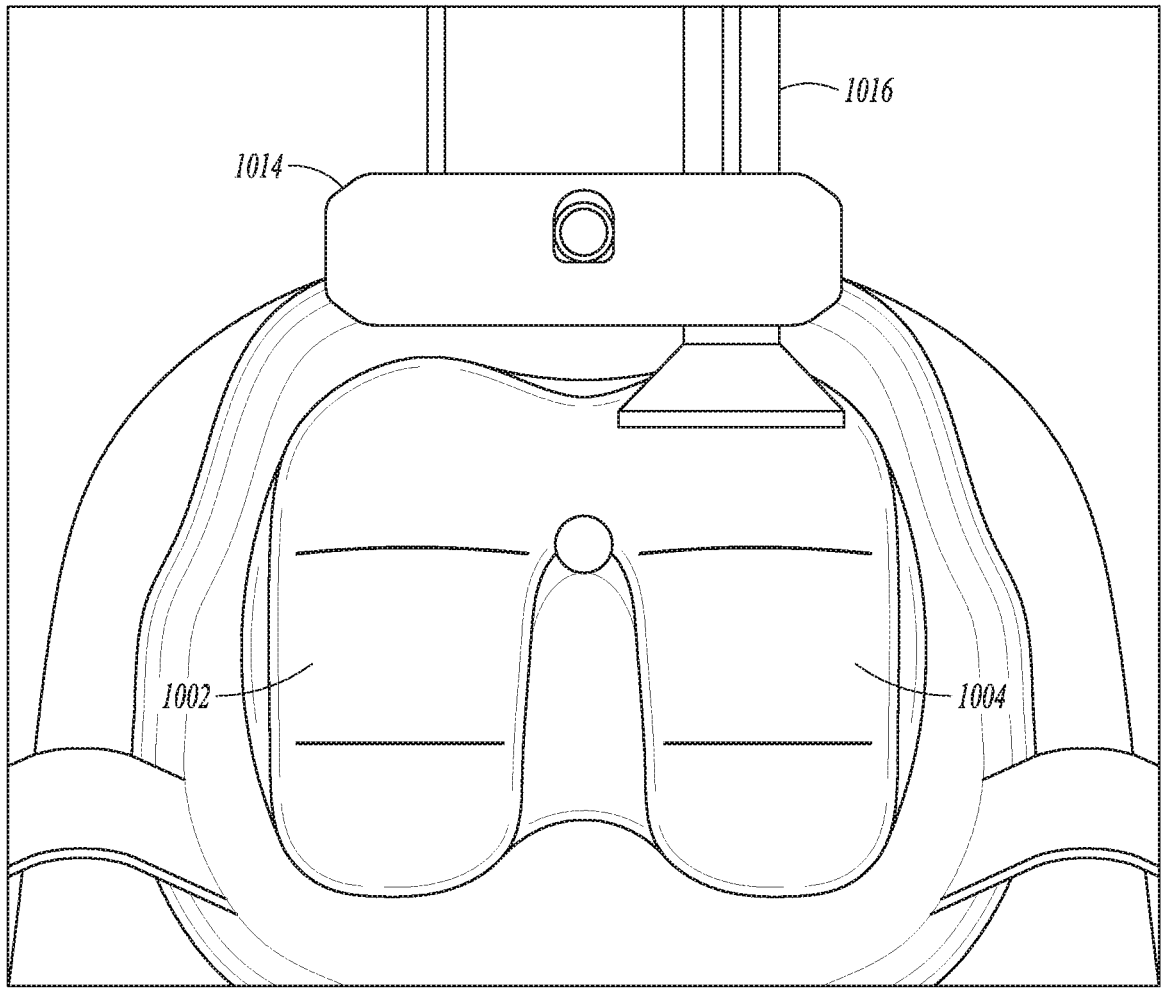
FIG. 18 is an image of the distal femur as the lateral condyle is being resected using a cutting tool and the cut guide.

To perform the distal resections, the resection tower 600' and the shim block assembly 200' can be removed from the knee and the cut guide 1014 can remain, as shown in FIG. 17. A saw blade or other cutting tool 1016 can then be inserted through a slot in the cut guide 1014 to perform the distal resections of the medial 1002 and lateral 1004 condyles. FIG. 18 illustrates a resection of the lateral condyle 1004 using the cutting tool 1016.

Figure 19:
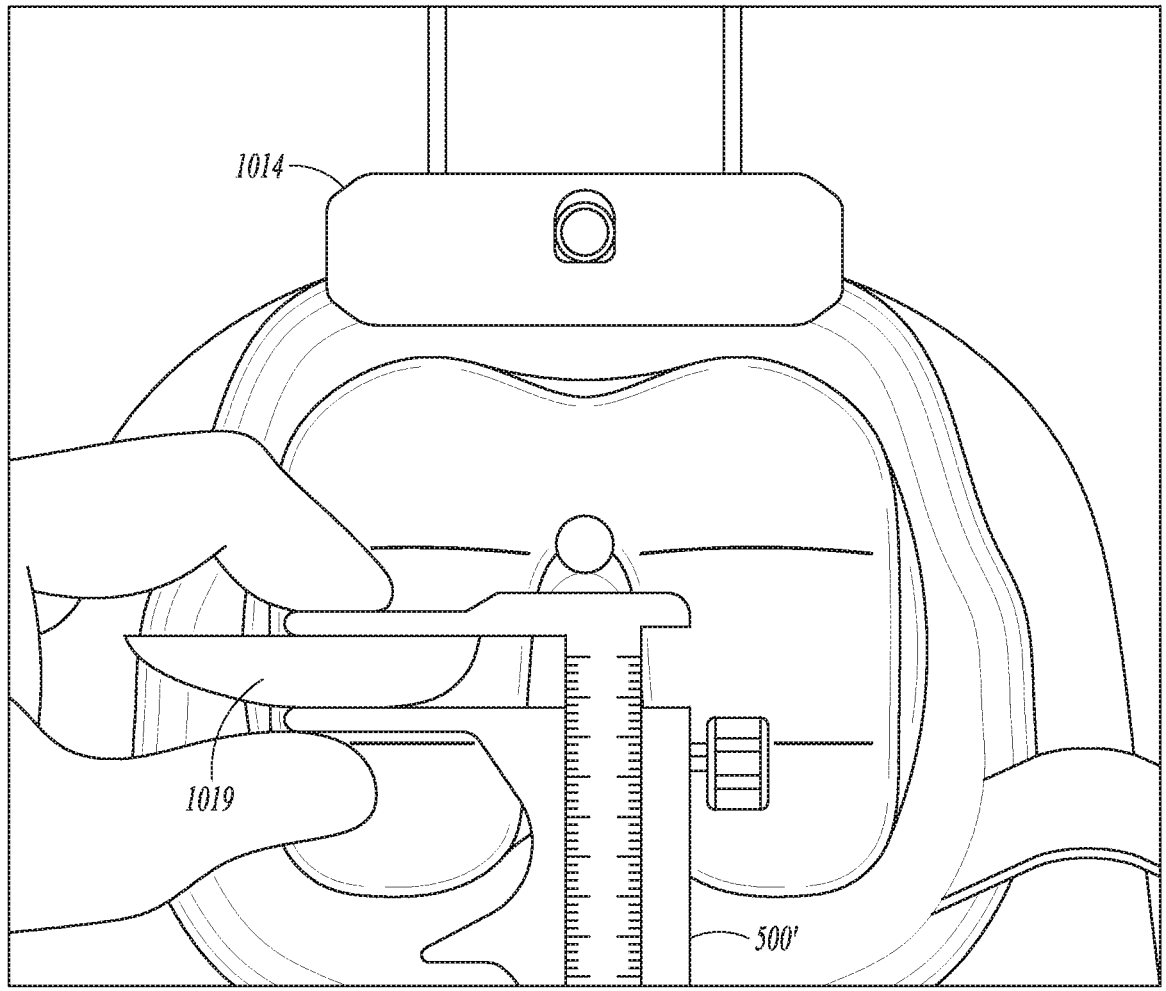
FIG. 19 is an image showing measurement of the bone resection from the distal femur.

After each of the distal medial 1002 and lateral 1004 condyles are resected, a thickness of each of the two resected bones can be measured to confirm that the target medial and lateral resection thicknesses were obtained. (Alternatively, the first resection can be performed and measured; and then the second resection can be performed and measured.) FIG. 19 illustrates such a measurement of a bone resection 1019 using the caliper 500', similar to the caliper 500 of FIG. 7. It is recognized that similar types of measurement tools can be used.

In the exemplary surgery used for the description herein, the patient had a medial condyle that was worn due to a varus deformity. As such, in this example, the target medial resection thickness can be 6 mm and the target lateral resection thickness can be 8 mm. If either of the measurements of the resected bone thickness is less than the target thickness, then additional bone can be resected from the distal femur 1000. If either of the measurements is more than the target thickness, one or more spacers, similar to the spacers 400 and 402 of FIG. 6, can be placed on a cut block used for performing the posterior, posterior chamfer, anterior and anterior chamfer femoral resections, which is described further below. Once the distal resections are complete, the cut guide 1014 can be removed from the distal femur 1000.

The distal resections are described above as being performed with use of the intramedullary rod 1012 shown in FIGS. 14-16. It is recognized that an extramedullary alignment technique can also be used. The tower assembly 700 of FIG. 10 can be used, for example, in such an extramedullary alignment technique. As shown in FIG. 10, the tower assembly 700 can include the block assembly 200, and use of the block assembly 200 and the shim components 302A, 302B and 302C can be the same as described above. However, instead of inserting an intramedullary rod into the distal femur (see FIG. 14), an extramedullary alignment rod similar to the alignment rod 706 of the tower assembly 700 can be used for setting flexion/extension of the femoral prosthesis. In an extramedullary technique, an overall height of the tower assembly 700 can be taller, as compared, for example, to the resection tower 600 of FIG. 8, in order for the tower assembly 700 to have clearance relative to a patient's thigh.

The distal resections are described above as being performed with use of the modular shim block assembly including the block assembly 200' and a shim component selected from the set 300 of shim components 302A, 302B or 302C. It is recognized that the distal resections can also be performed using the steps described above with a one-piece shim block assembly such as any of the shim block assemblies 102A-102D from the set 100. The one-piece shim block assembly can be used in an intramedullary or extramedullary alignment technique.

The distal resection steps described above can set three degrees of freedom of the femoral prosthesis to be implanted—(1) proximal/distal, (2) varus/valgus, and (3) flexion/extension. Using the surgical technique described herein, the varus/valgus angle of the distal joint line can be restored to its pre-arthritic position. The use of a shim block assembly, whether a one-piece, monolithic design or a modular, multi-component design, can provide a simple, accurate and repeatable method for setting the location of the resections on the distal medial and lateral condyles. The spacers can be used in combination with the shim block assembly to compensate for a difference in a thickness of the bone resection from the targeted thickness.

Posterior Femoral Resections

Figure 20:
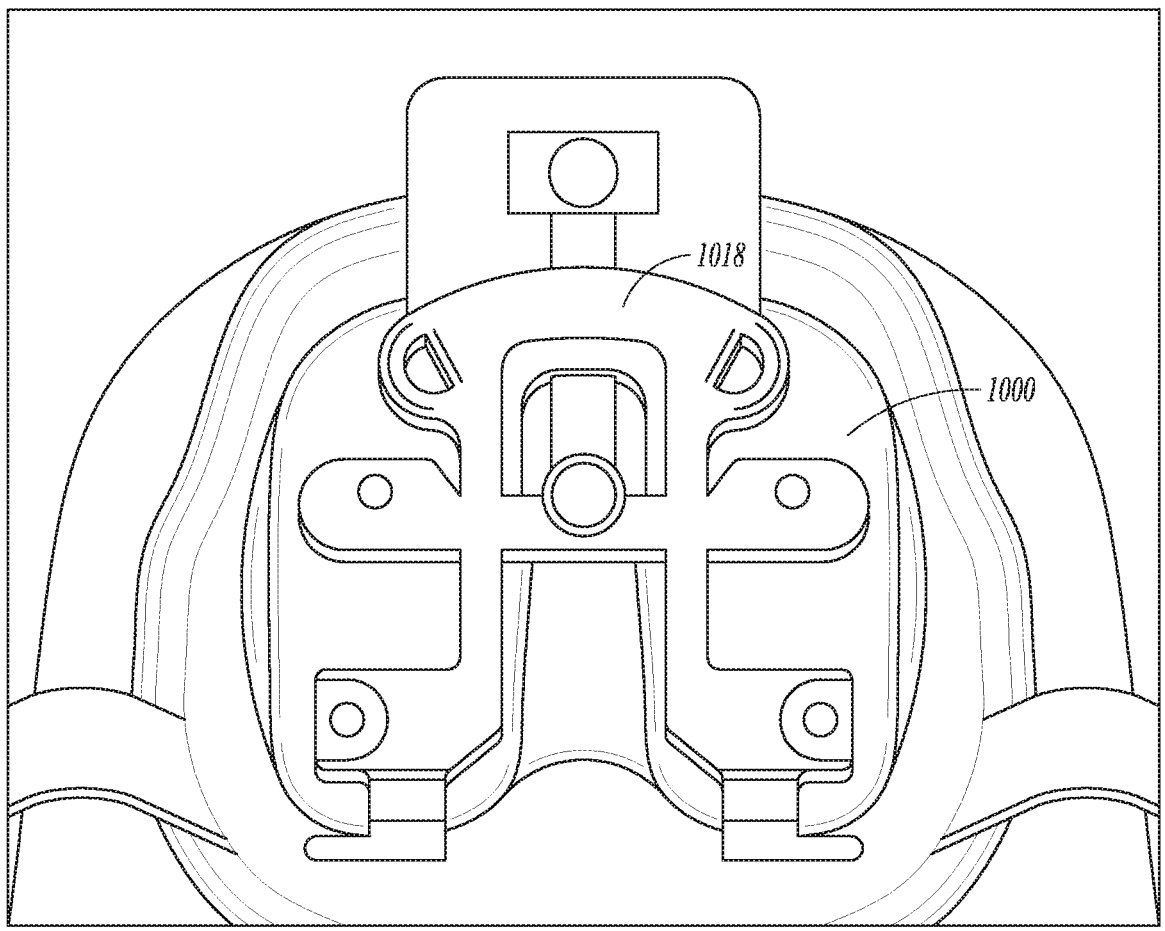
FIG. 20 is an image of a femoral sizer positioned on the distal femur.

A posterior reference A/P femoral sizer 1018, or a similar type of standard mechanical axis guide, can be placed on the distal femur 1000 to size the femur 1000, as shown in FIG. 20. The femoral sizer 1018 can be set at zero degrees of external rotation. A size of the femoral prosthesis can be determined based on a reading obtained on the sizer 1018.

Figure 21:
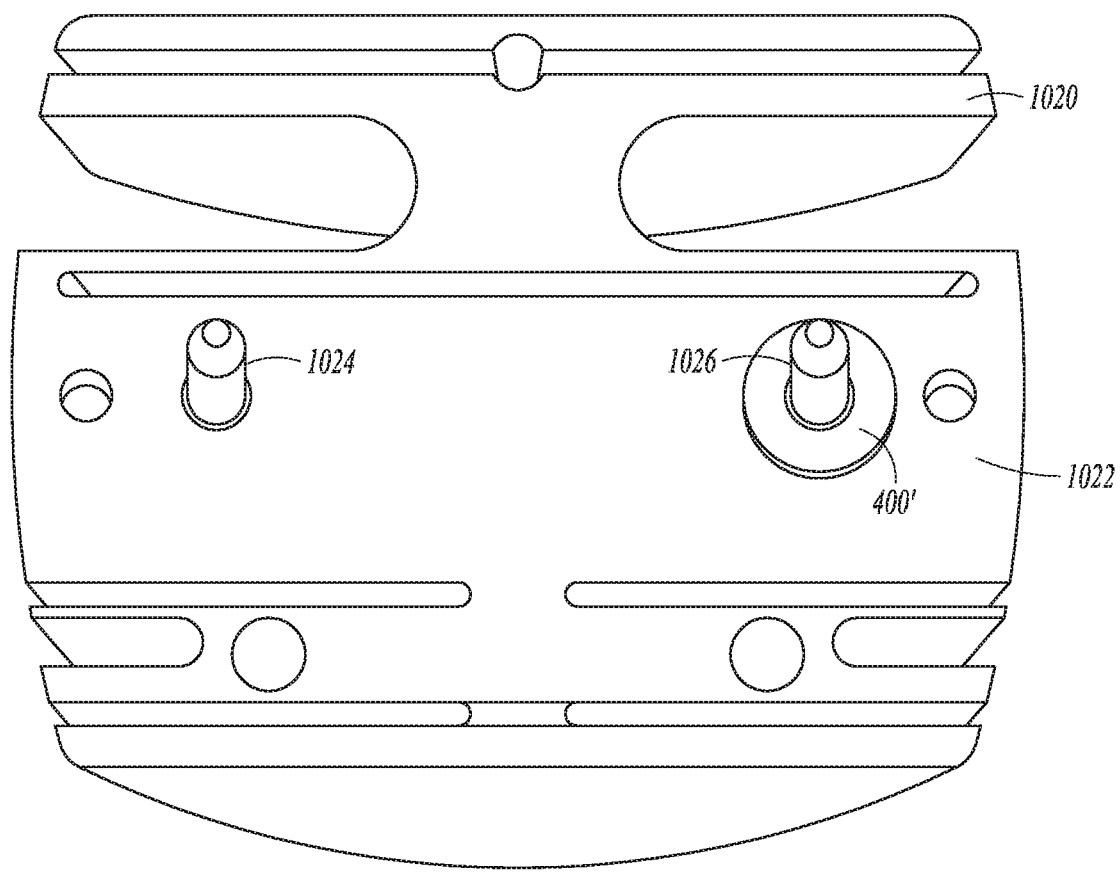
FIG. 21 is an image of a bone contacting side of a posterior cut block.

Next, two holes can be drilled in the distal femur 1000 to set two additional degrees of freedom—(1) anterior/posterior and (2) internal/external rotation. A posterior cut block, such as a Persona 4-in-1 cut block 1020 shown in FIG. 21, or a comparable type of device, can be inserted into the drilled holes. A size of the cut block 1020 can be selected to match the size of the femur 1000 determined above. FIG. 21 shows a bone contacting side 1022 of the cut block 1020, which includes two pins 1024 and 1026 configured for placement in the two holes drilled in the distal femur 1000.

As described above, if it is determined that one or both of the distal resections resulted in the resection of too much bone, then one or more spacers can be placed over one or both of the pins 1024 and 1026 on the bone contacting side 1022 of the cut block 1020. In an example, if the target distal medial resection thickness was 6 mm and the measurement above determined that 7 mm of bone was resected from the medial condyle, a spacer 400' having a thickness of 1 mm can be placed on the pin 1026, as shown in FIG. 21. The use of one or more spacers on the posterior cut block 1020 can result in accurate posterior and chamfer bone resections, facilitating proper prosthesis placement to the patient's natural or constitutional state. When the femoral prosthesis is implanted, bone cement can be used to fill in any gaps to account for the excess bone resected from the distal medial or lateral condyle.

Figure 22:
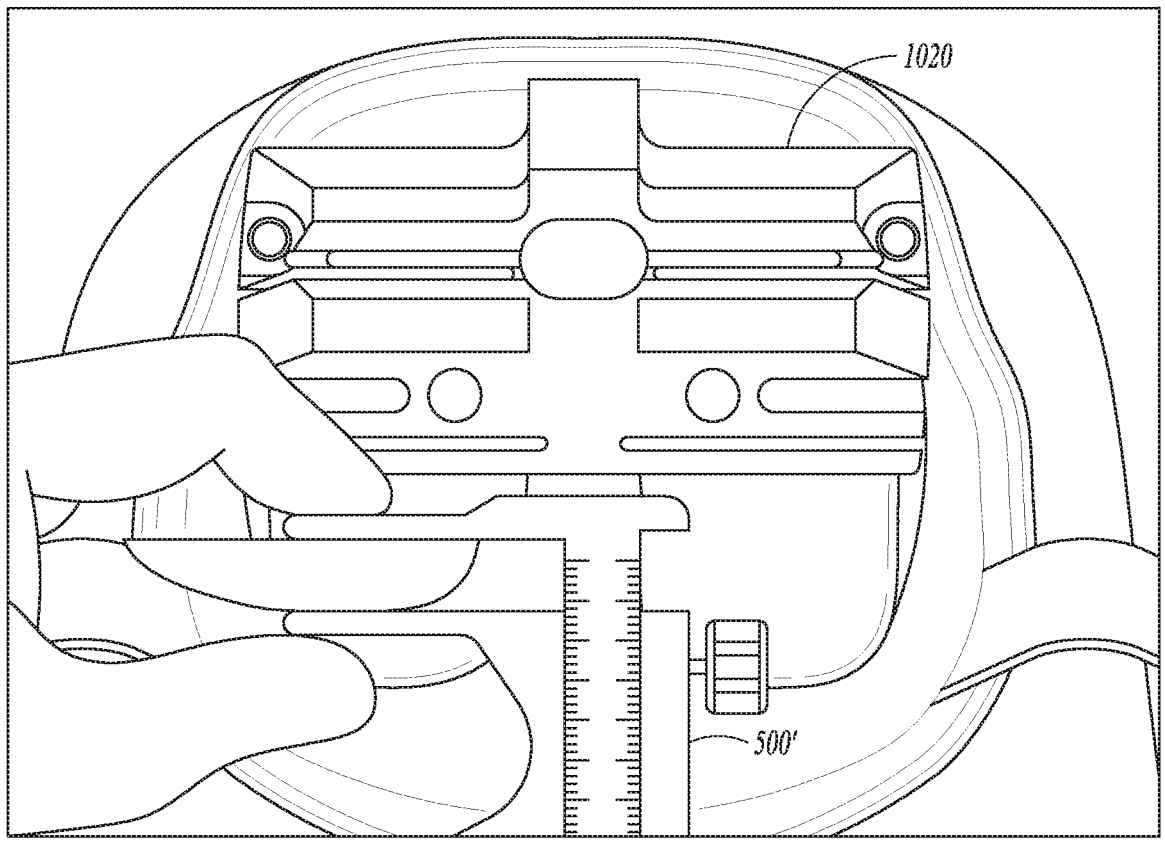
FIG. 22 is an image of the posterior cut block of FIG. 21 attached to the distal femur and a calipered measurement of the posterior medial condyle.

FIG. 22 shows the cut block 1020 of FIG. 21 attached to the femur 1000. The two posterior resections of the distal femur can next be performed. A thickness of the two posterior resections can be measured, as illustrated in FIG. 22, using caliper 500', to confirm that the target posterior resection thicknesses were obtained. In an example, the two target posterior resection thicknesses can each be about 8 mm.

As a final check, the surgeon or other participant in the surgery may wish to perform a final check of the four resections (2 distal and 2 posterior). Ensuring that the thickness of the distal and posterior resections matches with a thickness of the femoral prosthesis, after accounting for the cartilage wear, can serve as one of two checks for kinematic alignment. A second check is described further below.

Preparation of Tibia

Figure 23:
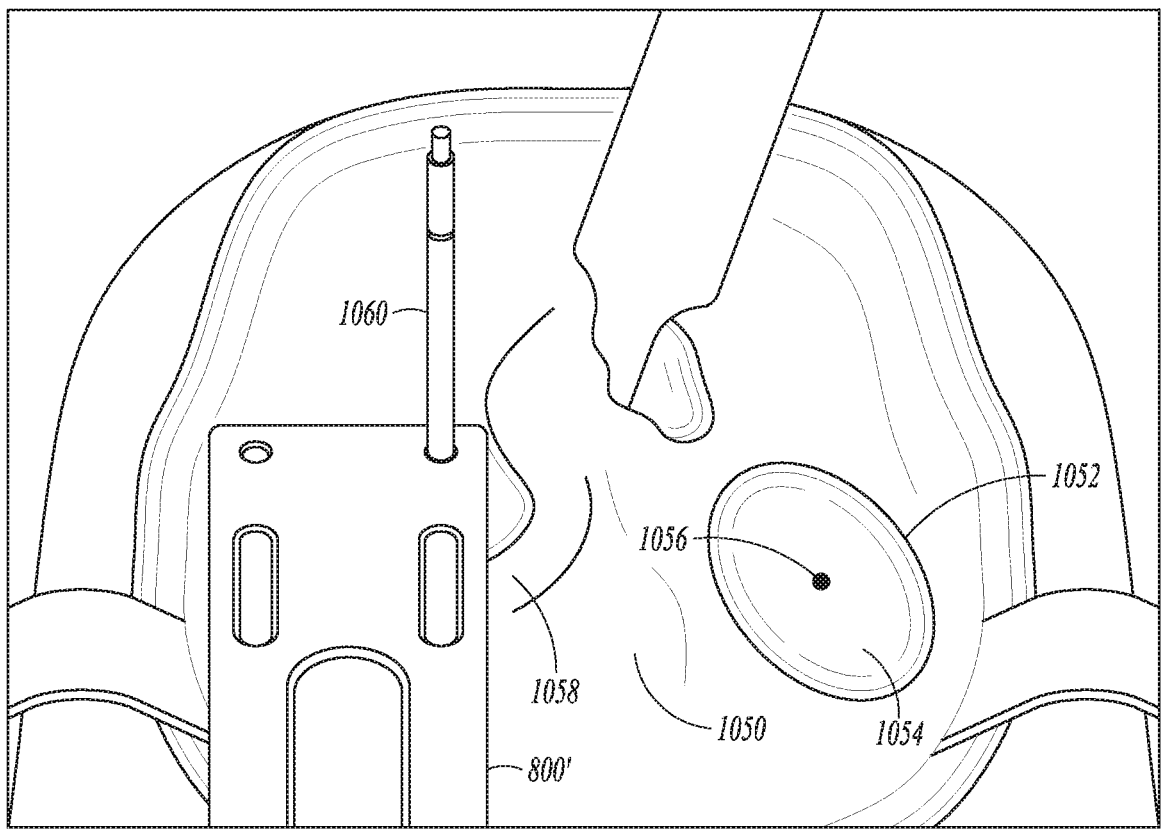
FIG. 23 is an image of a tibia of the knee joint shown in FIGS. 13-22.

The next steps in the surgical technique are used in preparation for implanting the tibial prosthesis. In a kinematically aligned TKA, an anterior/posterior (A/P) axis of the tibial prosthesis can be determined based on an arthritic wear pattern rather than on an anatomic measurement. In preparation for determining the A/P axis, the tibia 1050 can be exposed and the medial and lateral menisci can be removed, while retaining the PCL. As shown in FIG. 23, a nearly elliptical boundary 1052 of the lateral tibial plateau 1054 can be outlined with a marking pen. A major axis 1056 of the ellipse can also be marked.

An alignment guide 800', similar to the guide 800 of FIG. 11, can be placed on the medial tibial plateau 1058 and used to drill a posterior pin hole into the medial tibial plateau 1058 and a posterior pin 1060 can be inserted. The alignment guide 800' can then be rotated about the pin 1060 until the guide 800' is parallel to the major axis on the lateral plateau 1054 and then the anterior pin hole can be drilled and an anterior pin inserted. The major axis can approximate the direct anterior/posterior (A/P) cartilage wear and can allow the surgeon to set the internal/external (I/E) rotation of the tibial prosthesis.

Figure 24:
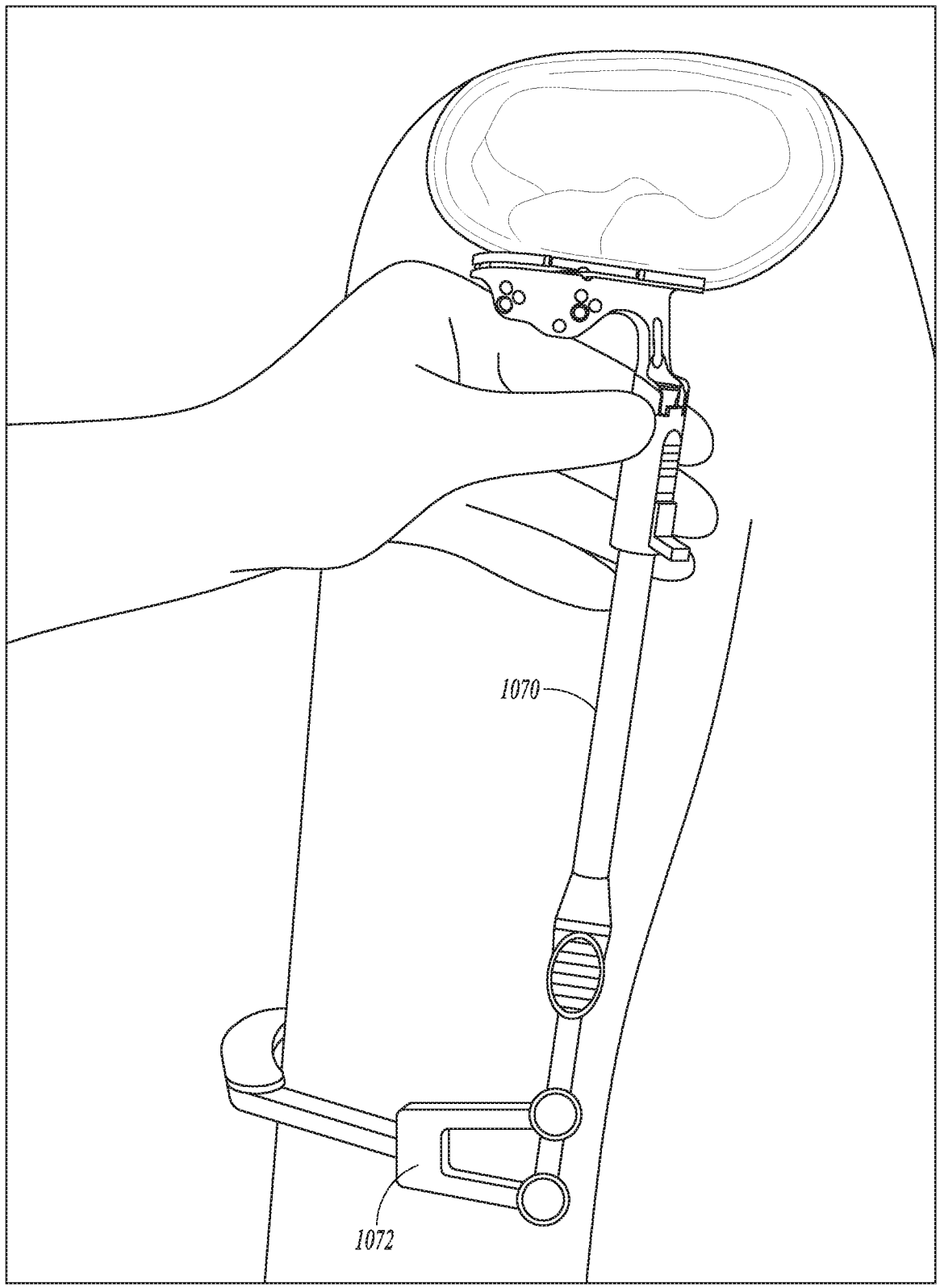
FIG. 24 is an image of a tibial resection tower attached to the leg of the patient.

The tibial resection can next be set, including a proximal/distal (P/D) level, varus/valgus (V/V) angle, and anterior/posterior slope. As shown in FIG. 24, a Persona Proximal Tibial Resection tower 1070 or similar instrument can be placed on the patient's leg. The medial/lateral (M/L) slider 1072 of the tower 1070 can be adjusted at the ankle of the leg until the varus/valgus angle of the plane of the tibial resection is parallel to the patient's proximal tibia. This allows the surgeon to approximate the anatomic varus of the patient's proximal tibia. The medial/lateral slider 1072 can commonly be placed far laterally at the ankle to achieve the parallel plane or anatomic varus of the patient's proximal tibia.

Figure 25:
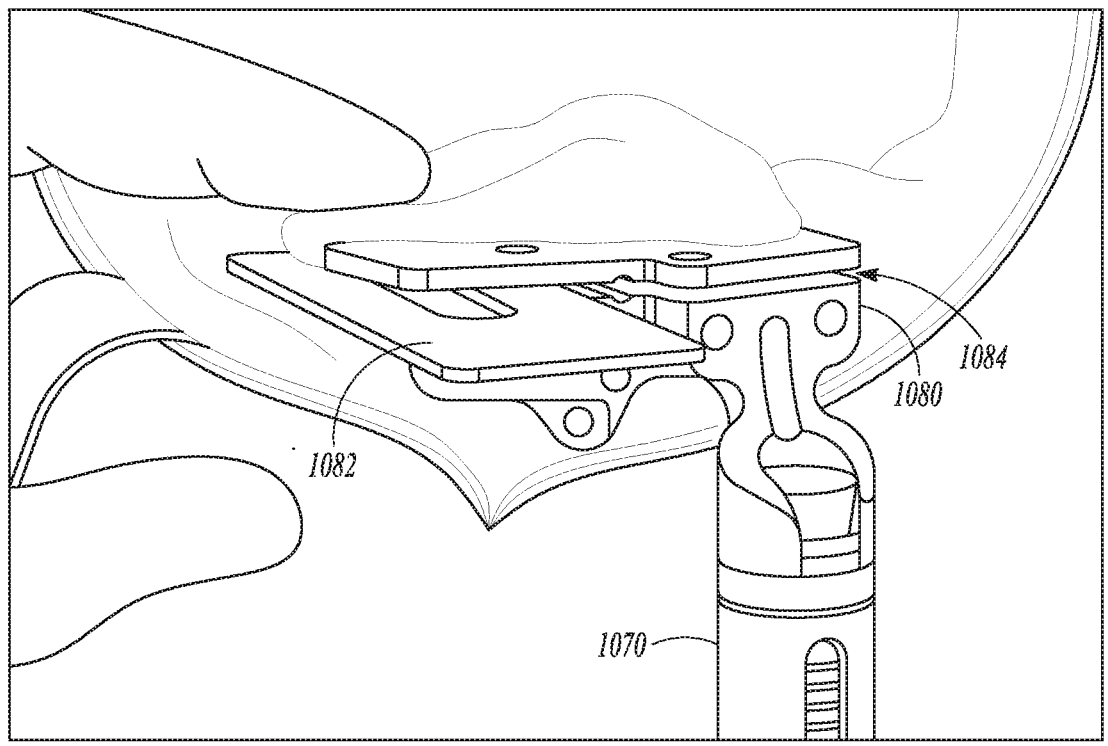
FIG. 25 is an image of a tibial cut guide of the resection tower of FIG. 24 for performing resection of the tibia.

FIG. 25 shows a tibial cut guide 1080, which can be attached to the resection tower 1070, and configured to perform the tibial resection. An angel wing 1082 can be placed in a medial portion of a cut slot 1084 of the cut guide 1080. An anterior/posterior slope of the angle wing 1082 can be adjusted to match, or be move conservative to (i.e. undercorrect), the natural anterior/posterior slope of the medial tibia by about 1-2 degrees.

The proximal/distal level of the tibial resection can be adjusted to remove 10 mm of anatomy, which can include bone and cartilage from a tibial surface. A conservative posterior slope and proximal/distal resection can help preserve the insertion of the PCL. The cut guide 1080 can then be pinned and the tibial resection can be performed.

Figure 26:
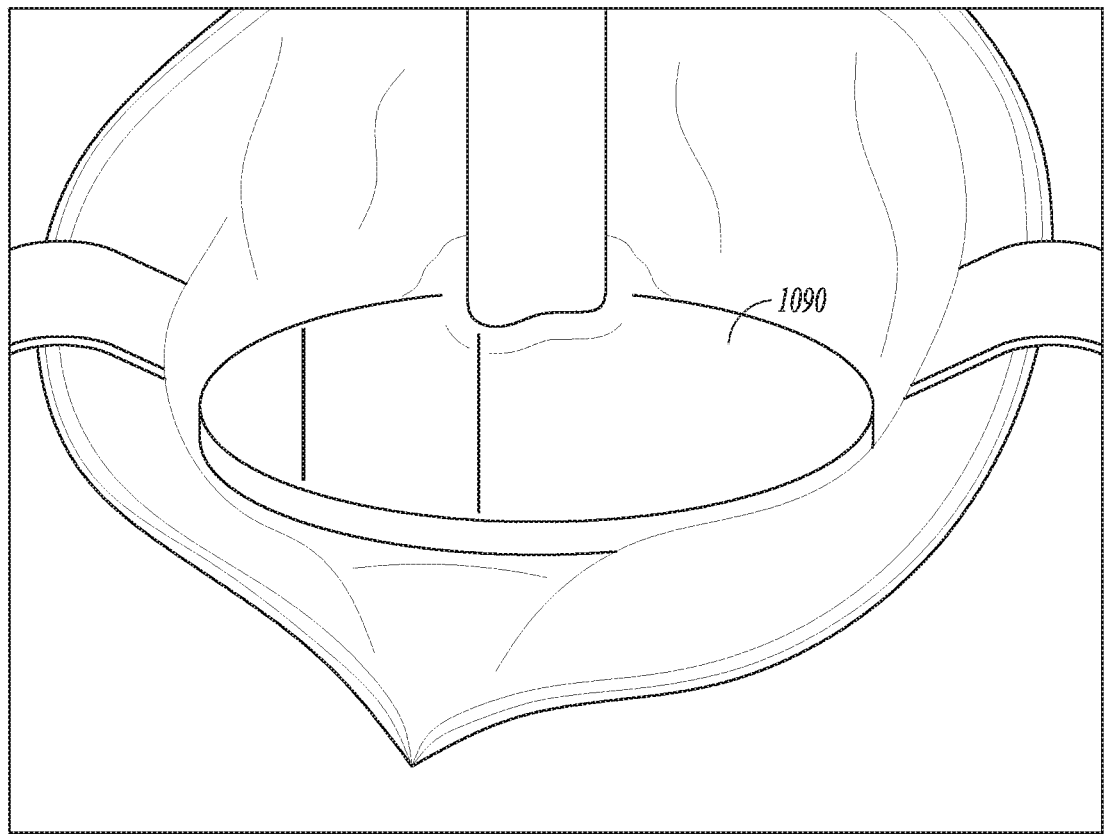
FIG. 26 is an image of the resected tibia.

FIG. 26 shows the resected tibia 1090 following the steps described above in reference to FIG. 25. Next a line can be drawn for setting rotation of the anterior/posterior axis of the tibial trial component. Assuming the major anterior/posterior of the generally elliptically shaped lateral tibial plateau was properly drawn (see FIG. 23), the line to be drawn can connect the two previously drilled holes in the proximal tibia using a marker and an osteotome as a straight edge. If the line was not centered on the anterior/posterior axis of the ellipse, then the rotation of the line from the two drilled holes can be adjusted to correct for any error. The anterior/posterior axis of the tibial trial component can then be aligned to this line. As described above in reference to FIG. 23, the I/E rotation of the tibial component can be based on the A/P axis of the tibia, accounting for the A/P cartilage wear pattern.

The posterior flexion space can then be cleared and the flexion contracture can be corrected. This can include inserting a lamina spreader in the lateral compartment with the patient's knee in 90 degrees of flexion and removing the medial meniscus, Baker's cyst, posterior femoral and medial tibial osteophytes, and, when there is a flexion contracture, releasing the posterior capsule off the femur with a curved osteotome. Any bone on the lateral edge of the medial femur encroaching on the PCL can be removed. The lamina spreader can then be placed in the medial compartment and the same steps can be performed to clear the posterior space on the lateral side.

Inserting Trial Components and Confirming/Adjusting Kinematic Alignment

The second check for kinematic alignment of the knee joint can be restoration of the natural A/P offset, as measured above in reference to FIG. 12, once the trial or provisional components are in position on the knee joint.

The trial or provisional components, which can include a provisional femoral component, a provisional tibial baseplate, and a provisional bearing component, can be positioned in the knee joint. In an example, the provisional bearing component, which can act as the articulating component, can be formed of a plastic such as polyethylene.

The knee can be extended to 0 degrees of extension and the varus/valgus laxity can be checked. If the lateral compartment is loose, the tibia can be recut 2 degrees more varus and the original provisional bearing component can be replaced with a provisional bearing component that is 2 mm thicker. If the knee excessively hyperextends, a thicker bearing component can be inserted. Next, conformation of the correction of the preoperative deformity of the lower extremity to the natural alignment of the patient can be performed and compared to the other lower extremity. If the knee had a fixed valgus deformity and the limb is more valgus than the natural alignment, then the thickened arcuate complex can be released and the tibia can be recut 2 degrees more varus. Additionally a bearing component that is 2 mm thicker can be inserted.

In a next step, the knee can be flexed to 90 degrees and the A/P offset can be measured as described above under FIG. 12—from the anterior tibia to the distal medial femoral condyle. If the measurement is equal to the natural anterior/posterior (A/P) offset measurement taken at the beginning of the surgical procedure, then the knee is kinematically aligned. If the measurement is greater than the earlier measurement, then increase the posterior slope 1 degree for about every 1.5 mm the offset has to be reduced (or 2 degrees per about 3 mm of offset). This can result in posterior movement of the tibia relative to the femur. If the measurement is less than the earlier measurement, check the competency of the PCL. If the PCL is detached, use the narrow version of the posterior stabilized femoral component in the next size up. The anterior flange of the femoral component can be placed on the anterior cortex, the holes can be drilled, and the 2 mm posterior gap can be filled with cement. If the PCL is intact, a thicker bearing component can be inserted and the varus/valgus laxity can be rechecked in 0 degrees of extension to confirm the knee is not too tight. If the knee is too tight, then decrease the posterior slope and use a thicker bearing component.

FIG. 27 illustrates an example of a set 1100 of shim blocks 1102A and 1102B for use in performing the kinematically aligned TKA. The set 1100 of shim block assemblies 1102A and 1102B can be used in the surgical procedure to account for wear on the distal femur as was previously described. Each shim block assembly 1102A and/or 1102B can be constructed in a manner similar to the example of FIGS. 2-5 and can include a bone contacting side 1104 and a recess 1110 for receiving a portion of the intramedullary rod. However, unlike the examples of FIGS. 2-5, the shim blocks 1102A and 1102B do not each include a lateral portion and a medial portion. Instead the shim blocks 1102A and 1102B are particularized to one of the medial or lateral condyles. Thus, shim blocks 1102A and 1102B comprise separate components from one another that are not joined as with prior examples.

FIG. 28 shows each of the medial side shims (e.g., shim block 1102A) and each of the lateral side shims (e.g., shim block 1102B) can be configured for attachment to one of a medial side 1202A or a lateral side 1202B of a block assembly 1200 (also called a reference block). FIG. 28 also shows a front view of a resection tower 1300 with the block assembly 1200 and shims 1102A and 1102B in the process of being assembled on the resection tower 1300. The construction and components of the resection tower and the block assembly have previously been described (e.g., in reference to FIGS. 9 and 16), and therefore, will not be discussed in great detail. As shown in FIG. 28, the block assembly 1200 and shims 1102A and 1102B can be removeably secured to the resection tower 1300. As described above in reference to the surgical technique, the configuration shown in FIG. 28 can be used for initially placing the block assembly 1200 and shims 1102A and 1102B on the distal femur. The resection tower 1300 can also be configured to removeably secure the cut guide that performs the distal resections.

As described above, the process of inserting trial components can include replacing the provisional bearing component with another bearing component of a different thickness. It is recognized that other types of trialing or provisional systems can alternatively be used during this process. For example, a provisional system that includes a bearing component and a base component can be configured to receive a shim component between the bearing component and the base component. Multiple shim components can be available in varying thicknesses such that one bearing component can be used and the shim components can be used to increase or decrease a thickness of the tibial prosthesis. Reference is made to U.S. Pat. No. 8,603,101, titled PROVISIONAL TIBIAL PROSTHESIS SYSTEM, which includes examples of tibial provisional systems using the shim components described above.

Once the A/P offset has been restored using the steps provided above, the arthroplasty procedure can be finished using standard surgical techniques.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A system for performing a total knee arthroplasty, the system comprising:
a distal femoral cut guide configured to resect a distal medial condyle and a distal lateral condyle of a femur;
a reference block having a medial portion with a surface configured to abut the distal medial condyle of the femur and a lateral portion with a surface configured to abut the distal lateral condyle of the femur, wherein the medial portion has a first thickness and the lateral portion has a second thickness that differs from the first thickness of the medial portion, wherein the reference block is configured for connection with the distal femoral cut guide and is configured to set a position of the distal femoral cut guide relative to the femur.

2. The system of claim 1, further comprising a plurality of shims, wherein the first thickness of the medial portion and the second thickness of the lateral portion is set by one or more of the plurality of shims which have a medial shim thickness that differs from a lateral shim thickness, and wherein the one or more of the plurality of shims is attachable to or integral with the reference block.

3. The system of claim 2, wherein each of the plurality of shims is configured for contact with at least one or both of the distal medial condyle or the distal lateral condyle of the femur.

4. The system of claim 2, wherein the one or more of the plurality of shims is selected for use from the plurality of shims based on matching at least one of the medial and lateral thicknesses of the one or more of the plurality of shims with a determined wear of cartilage on at least one of the distal medial condyle and the distal lateral condyle.

5. The system of claim 2, wherein the plurality of shims comprise both medial side shims and lateral side shims, and wherein the medial side shims and lateral side shims comprise separate components from one another, and wherein each of the medial side shims and each of the lateral side shims are configured for attachment to a respective one of the medial portion or the lateral portion of the reference block.

6. The system of claim 1, wherein at least one of the first thickness of the medial portion or the second thickness of the lateral portion are selected based on matching to a determined wear of cartilage on at least one of the distal medial condyle or the distal lateral condyle.

7. The system of claim 1, wherein the reference block includes a slot configured to receive an intermedullary rod, wherein the slot is configured to allow for medial-lateral adjustment of a position of the reference block relative to the intermedullary rod and femur.

8. The system of claim 1, wherein the reference block further includes a second aperture in the medial portion and a third aperture in the lateral portion, and wherein the second and third apertures are each configured to receive a fixation device to attach the reference block to the femur.

9. A system for performing a total knee arthroplasty, the system comprising:
a distal femoral cut guide configured to resect a distal medial condyle and a distal lateral condyle of a femur;
a reference block having a slot configured to receive an intermedullary rod, wherein the reference block has a medial portion with a surface configured to abut the distal medial condyle of the femur and a lateral portion with a surface configured to abut the distal lateral condyle of the femur, wherein the medial portion has a first thickness and the lateral portion has a second thickness that differs from the first thickness of the medial portion, wherein the reference block is configured for connection with the distal femoral cut guide and is configured to set a position of the distal femoral cut guide for resection of the distal medial and lateral condyles when the reference block abuts the femur.

10. The system of claim 9, further comprising a plurality of shims, wherein the first thickness of the medial portion and the second thickness of the lateral portion is set by one or more of the plurality of shims which have a medial shim thickness that differs from a lateral shim thickness, and wherein the one or more of the plurality of shims is attachable to or integral with the reference block.

11. The system of claim 10, wherein each of the plurality of shims is configured for contact with at least one or both of the distal medial condyle or the distal lateral condyle of the femur.

12. The system of claim 10, wherein the one or more of the plurality of shims is selected for use from the plurality of shims based on matching at least one of the medial and lateral thicknesses of the one or more of the plurality of shims with a determined wear of cartilage on at least one of the distal medial condyle and the distal lateral condyle.

13. The system of claim 10, wherein the plurality of shims comprise both medial side shims and lateral side shims, and wherein the medial side shims and lateral side shims comprise separate components from one another, and wherein each of the medial side shims and each of the lateral side shims are configured for attachment to a respective one of the medial portion or the lateral portion of the reference block.

14. The system of claim 9, wherein at least one of the first thickness of the medial portion or the second thickness of the lateral portion are selected based on matching to a determined wear of cartilage on at least one of the distal medial condyle or the distal lateral condyle.

15. The system of claim 9, wherein the reference block further includes a second aperture in the medial portion and a third aperture in the lateral portion, and wherein the second and third apertures are each configured to receive a fixation device to attach the reference block to the femur.

16. An assembly for performing a total knee arthroplasty, the assembly comprising:

a distal femoral cut guide configured to resect a distal medial condyle and a distal lateral condyle of a femur;

a reference block coupled to the distal femoral cut guide and configured to abut the distal medial condyle and the distal lateral condyle to set a position of the distal femoral cut guide relative to the femur to resect the distal medial condyle and the distal lateral condyle, wherein when the reference block is mounted to the femur, the reference block has a medial portion with a surface that abuts the distal medial condyle and a lateral portion with a surface that abuts the distal lateral condyle, and wherein the medial portion has a first thickness and the lateral portion has a second thickness that differs from the first thickness of the medial portion.

17. The assembly of claim 16, wherein the reference block includes a slot configured to receive an intermedullary rod, wherein the slot is configured to allow for medial-lateral adjustment of a position of the reference block relative to the intermedullary rod and femur.

18. The assembly of claim 16, wherein the reference block mounts to the femur via a second aperture in the medial portion and a third aperture in the lateral portion, and wherein the second and third apertures each receive a fixation device to attach the reference block to the femur.

19. The assembly of claim 16, further comprising a plurality of shims, wherein the first thickness of the medial portion and the second thickness of the lateral portion is set by one or more of the plurality of shims which have a medial shim thickness that differs from a lateral shim thickness, and wherein the one or more of the plurality of shims is attachable to or integral with the reference block.

20. The assembly of claim 19, wherein the one or more of the plurality of shims is selected for use from the plurality of shims based on matching at least one of the medial and lateral thicknesses of the one or more of the plurality of shims with a determined wear of cartilage on at least one of the distal medial condyle and the distal lateral condyle.

21. The assembly of claim 16, wherein at least one of the first thickness of the medial portion or the second thickness of the lateral portion are selected based on matching to a determined wear of cartilage on at least one of the distal medial condyle or the distal lateral condyle.

* * * * *